US012605037B2

(12) United States Patent
Hazelton et al.

(10) Patent No.: US 12,605,037 B2
(45) Date of Patent: Apr. 21, 2026

(54) SYSTEMS AND METHODS FOR ORIENTATION DETECTION AND TOOL INSTALLATION

(71) Applicant: INTUITIVE SURGICAL OPERATIONS, INC., Sunnyvale, CA (US)

(72) Inventors: Andrew J. Hazelton, San Carlos, CA (US); Teresa G. Gadda, Palo Alto, CA (US); Changmeng Liu, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/882,529

(22) Filed: Sep. 11, 2024

(65) Prior Publication Data

US 2025/0040786 A1     Feb. 6, 2025

Related U.S. Application Data

(63) Continuation of application No. 17/258,705, filed as application No. PCT/US2019/041218 on Jul. 10, 2019, now Pat. No. 12,161,286.

(Continued)

(51) Int. Cl.
*A61B 1/00*         (2006.01)
*A61B 17/00*        (2006.01)
(Continued)

(52) U.S. Cl.
CPC .. *A61B 1/000094* (2022.02); *A61B 1/000095* (2022.02); *A61B 17/00234* (2013.01);
(Continued)

(58) Field of Classification Search
CPC .......................... A61B 1/000095; A61B 34/20
See application file for complete search history.

(56) References Cited

U.S. PATENT DOCUMENTS

| | | | |
|---|---|---|---|
| 6,162,179 A | 12/2000 | Moore | |
| 6,306,097 B1 * | 10/2001 | Park | A61B 8/12 |
| | | | 600/468 |

(Continued)

FOREIGN PATENT DOCUMENTS

| | | |
|---|---|---|
| CN | 101516266 A | 8/2009 |
| CN | 106901719 A | 6/2017 |

(Continued)

OTHER PUBLICATIONS

International Preliminary Report on Patentability for Application No. PCT/2019/041218, mailed on Jan. 21, 2021, 09 pages.

(Continued)

*Primary Examiner* — Rochelle D Turchen
(74) *Attorney, Agent, or Firm* — Haynes & Boone, LLP.

(57)     ABSTRACT

An apparatus comprises a processor and a memory having computer readable instructions stored thereon. The computer readable instructions, when executed by the processor, cause the apparatus to capture, via an image sensor of a tool installed at least partially within a catheter, a first image within a lumen of the catheter. The first image comprises a plurality of pixels. The instructions further cause the apparatus to identify a first subset of the pixels comprising a viewable feature, and a second subset of the pixels comprising a background color. The instructions further cause the apparatus to adjust the second subset to a neutral color, create a modified image by filtering the pixels to remove the second subset, determine an angular orientation of the viewable feature in the modified image, and determine a (Continued)

rotational offset of the tool relative to the catheter based on the angular orientation of the viewable feature.

20 Claims, 34 Drawing Sheets

Related U.S. Application Data

(60) Provisional application No. 62/696,178, filed on Jul. 10, 2018.

(51) Int. Cl.
*A61B 34/20* (2016.01)
*A61B 34/00* (2016.01)

(52) U.S. Cl.
CPC .... *A61B 34/20* (2016.02); *A61B 2017/00292* (2013.01); *A61B 2034/2051* (2016.02); *A61B 2034/2055* (2016.02); *A61B 2034/2061* (2016.02); *A61B 34/25* (2016.02)

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 2008/0306379 A1 | 12/2008 | Ikuma et al. | |
| 2013/0083999 A1 | 4/2013 | Bhardwaj et al. | |
| 2015/0087899 A1 | 3/2015 | Kung et al. | |
| 2021/0267695 A1 | 9/2021 | Hazelton et al. | |

FOREIGN PATENT DOCUMENTS

| | | | |
|---|---|---|---|
| EP | 0466327 A2 | 1/1992 | |
| EP | 2000087 A2 | 12/2008 | |
| EP | 3184036 A1 | 6/2017 | |

OTHER PUBLICATIONS

International Search Report and Written Opinion for Application No. PCT/US2019/041218, mailed on Oct. 18, 2019, 16 pages (ISRG11400/PCT).

Office Action for Chinese Application No. 201980055906.4. mailed Sep. 1, 2023, 12 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ORIENTATION DETECTION AND TOOL INSTALLATION

CROSS-REFERENCE TO RELATED APPLICATIONS

This application is a continuation of U.S. patent application Ser. No. 17/258,705, filed Jan. 7, 2021, which is the U.S. national phase of International Application No. PCT/US2019/041218, filed Jul. 10, 2019, which designated the U.S. and claims priority to and the benefit of U.S. Provisional Application No. 62/696,178, filed Jul. 10, 2018, all of which are incorporated by reference herein in their entireties.

TECHNICAL FIELD

The present disclosure is directed to systems and methods for detecting and recognizing an orientation of a tool in a catheter and in various embodiments may include determining proper installation of the tool in the catheter.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device.

Accordingly, it would be advantageous to develop improved systems and methods for use during minimally invasive medical techniques.

SUMMARY

Some embodiments of the invention are best summarized by the claims that follow the description.

Consistent with some embodiments, a method for determining an orientation of a tool installed at least partially within a catheter is provided. The method may include capturing, via an image sensor of the tool, a first image within a lumen of the catheter, the first image comprising a plurality of pixels. The method may further include identifying a first subset of the plurality of pixels comprising a viewable feature and a second subset of the plurality of pixels comprising a background color. The method may further include adjusting the second subset of the plurality of pixels to a neutral color. The method may further include creating a modified image by filtering the plurality of pixels to remove the second subset. The method may further include determining an angular orientation of the viewable feature in the modified image. The method may further include determining a rotational offset of the tool relative to the catheter based on the angular orientation of the viewable feature.

Consistent with some embodiments, a system for determining an orientation of a tool in a catheter is provided. The system may include the tool shaped to be positioned in a lumen of the catheter. The system may further include an imaging sensor positioned in the tool. The system may further include a viewable feature positioned in the catheter within a field of view of the imaging sensor, and the imaging sensor may be configured to capture images of the field of view including a first image that includes the viewable feature. A position of the viewable feature in the first image may indicate a rotational offset the tool has rotated within the catheter.

Consistent with some embodiments, a method for determining an orientation of a tool installed at least partially within a catheter is provided. The method may include capturing, via an image sensor of the tool, a first image within a lumen of the catheter, the first image comprising a plurality of pixels. The method may further include identifying a first subset of the plurality of pixels comprising a first viewable feature, a second subset of pixels comprising a second viewable feature, and a third subset of the plurality of pixels comprising a background color. The method may further include adjusting the third subset to a neutral color. The method may further include creating a modified image by filtering the plurality of pixels to remove the third subset. The method may further include determining an angular orientation of each of the first and second viewable features in the modified image. The method may further include determining a rotational offset of the tool relative to the catheter based on the angular orientations of the first and second viewable features.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
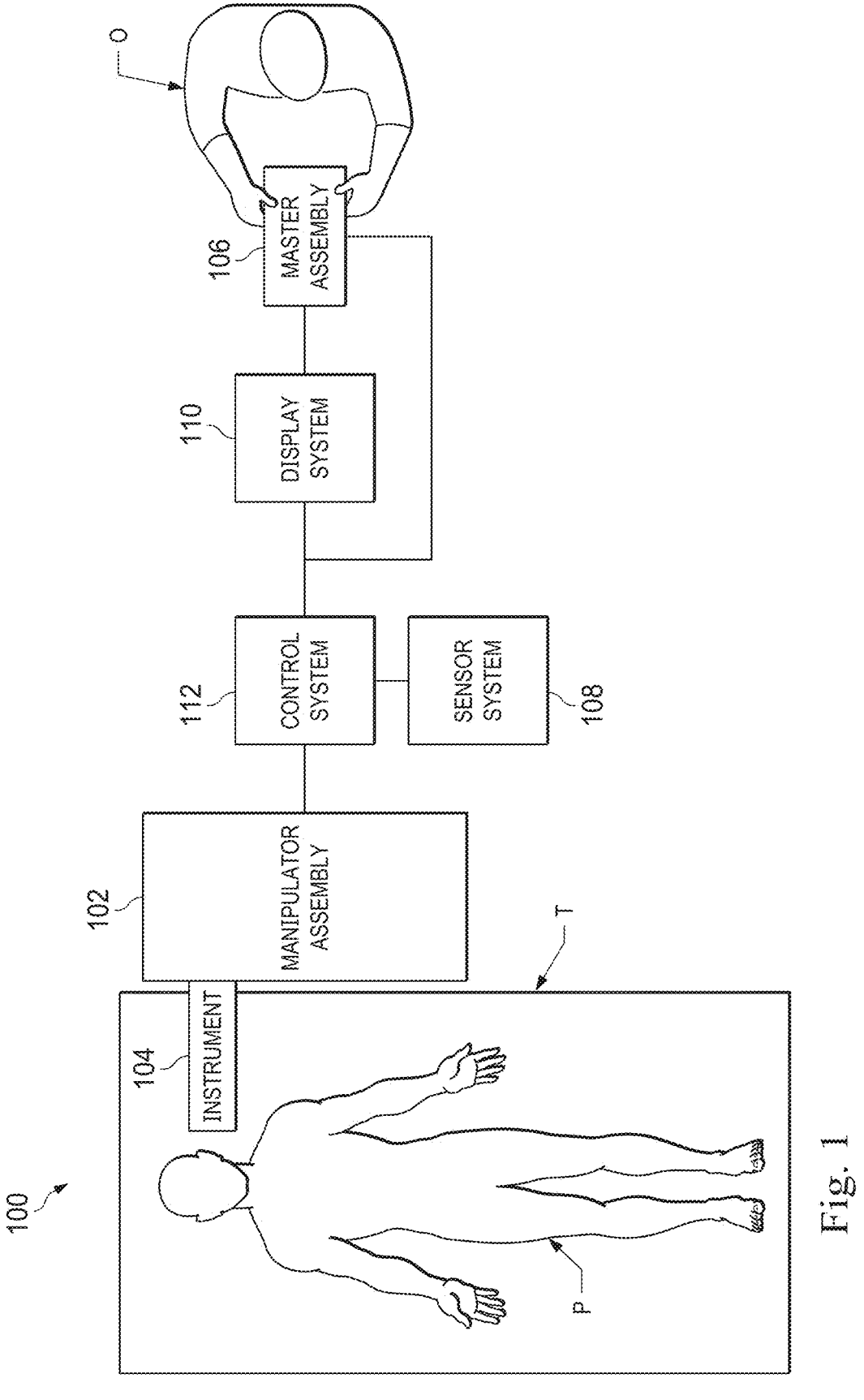
FIG. 1 is a simplified schematic diagram of a teleoperated medical system according to some embodiments.

Embodiments of the present disclosure and their advantages are best understood by referring to the detailed description that follows. It should be appreciated that like reference numerals are used to identify like elements illus-
trated in one or more of the figures, wherein showings
therein are for purposes of illustrating embodiments of the
present disclosure and not for purposes of limiting the same.

DETAILED DESCRIPTION

In the following description, specific details are set forth
describing some embodiments consistent with the present
disclosure. Numerous specific details are set forth in order to
provide a thorough understanding of the embodiments. It
will be apparent, however, to one skilled in the art that some
embodiments may be practiced without some or all of these
specific details. The specific embodiments disclosed herein
are meant to be illustrative but not limiting. One skilled in
the art may realize other elements that, although not spe-
cifically described here, are within the scope and the spirit
of this disclosure. In addition, to avoid unnecessary repeti-
tion, one or more features shown and described in associa-
tion with one embodiment may be incorporated into other
embodiments unless specifically described otherwise or if
the one or more features would make an embodiment
non-functional.

In some instances well known methods, procedures, com-
ponents, and circuits have not been described in detail so as
not to unnecessarily obscure aspects of the embodiments.

This disclosure describes various instruments and por-
tions of instruments in terms of their state in three-dimen-
sional space. As used herein, the term "position" refers to the
location of an object or a portion of an object in a three-
dimensional space (e.g., three degrees of translational free-
dom along Cartesian x-, y-, and z-coordinates). As used
herein, the term "orientation" refers to the rotational place-
ment of an object or a portion of an object (three degrees of
rotational freedom—e.g., roll, pitch, and yaw). As used
herein, the term "pose" refers to the position of an object or
a portion of an object in at least one degree of translational
freedom and to the orientation of that object or portion of the
object in at least one degree of rotational freedom (up to six
total degrees of freedom). As used herein, the term "shape"
refers to a set of poses, positions, or orientations measured
along an object.

FIG. 1 is a simplified diagram of a teleoperated medical
system 100 according to some embodiments. In some
embodiments, teleoperated medical system 100 may be
suitable for use in, for example, surgical, diagnostic, thera-
peutic, or biopsy procedures. While some embodiments are
provided herein with respect to such procedures, any refer-
ence to medical or surgical instruments and medical or
surgical methods is non-limiting. The systems, instruments,
and methods described herein may be used for animals,
human cadavers, animal cadavers, portions of human or
animal anatomy, non-surgical diagnosis, as well as for
industrial systems and general robotic or teleoperated medi-
cal systems.

As shown in FIG. 1, medical system 100 generally
includes a manipulator assembly 102 for operating a medical
instrument 104 in performing various procedures on a
patient P. The manipulator assembly 102 may be teleoper-
ated, non-teleoperated, or a hybrid teleoperated and non-
teleoperated assembly with select degrees of freedom of
motion that may be motorized and/or teleoperated and select
degrees of freedom of motion that may be non-motorized
and/or non-teleoperated. Manipulator assembly 102 is
mounted to or near an operating table T. A master assembly
106 allows an operator O (e.g., a surgeon, a clinician, or a physician as illustrated in FIG. 1) to view the interventional
site and to control manipulator assembly 102.

Master assembly 106 may be located at an operator
console which is usually located in the same room as
operating table T, such as at the side of a surgical table on
which patient P is located. However, it should be understood
that the operator O can be located in a different room or a
completely different building from patient P. Master assem-
bly 106 generally includes one or more control devices for
controlling manipulator assembly 102. The control devices
may include any number of a variety of input devices, such
as joysticks, trackballs, data gloves, trigger-guns, hand-
operated controllers, voice recognition devices, body motion
or presence sensors, and/or the like. To provide the operator
O a strong sense of directly controlling instruments 104 the
control devices may be provided with the same degrees of
freedom as the associated medical instrument 104. In this
manner, the control devices provide operator O with telep-
resence or the perception that the control devices are integral
with medical instruments 104.

In some embodiments, the control devices may have more
or fewer degrees of freedom than the associated medical
instrument 104 and still provide operator O with telepres-
ence. In some embodiments, the control devices may option-
ally be manual input devices which move with six degrees
of freedom, and which may also include an actuatable
handle for actuating instruments (for example, for closing
grasping jaws, applying an electrical potential to an elec-
trode, delivering a medicinal treatment, and/or the like).

Manipulator assembly 102 supports medical instrument
104 and may include a kinematic structure of one or more
non-servo controlled links (e.g., one or more links that may
be manually positioned and locked in place, generally
referred to as a set-up structure), and/or one or more servo
controlled links (e.g. one more links that may be controlled
in response to commands from the control system), and a
manipulator. Manipulator assembly 102 may optionally
include a plurality of actuators or motors that drive inputs on
medical instrument 104 in response to commands from the
control system (e.g., a control system 112). The actuators
may optionally include drive systems that when coupled to
medical instrument 104 may advance medical instrument
104 into a naturally or surgically created anatomic orifice.
Other drive systems may move the distal end of medical
instrument 104 in multiple degrees of freedom, which may
include three degrees of linear motion (e.g., linear motion
along the X, Y, Z Cartesian axes) and in three degrees of
rotational motion (e.g., rotation about the X, Y, Z Cartesian
axes). Additionally, the actuators can be used to actuate an
articulable portion of medical instrument 104 for grasping
tissue in the jaws of a biopsy device and/or the like. Actuator
position sensors such as resolvers, encoders, potentiometers,
and other mechanisms may provide sensor data to medical
system 100 describing the rotation and orientation of the
motor shafts. This position sensor data may be used to
determine motion of the objects manipulated by the actua-
tors.

Teleoperated medical system 100 may include a sensor
system 108 with one or more sub-systems for receiving
information about the instruments of manipulator assembly
102. Such sub-systems may include a position/location
sensor system (e.g., an electromagnetic (EM) sensor sys-
tem); a shape sensor system for determining the position,
orientation, speed, velocity, pose, and/or shape of a distal
end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of image-guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory (not shown) and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the control system 112 may include two or more data processing circuits distributed throughout the teleoperated medical system 100 to perform distributed data processing. For example, one portion of the data processing performed by the distributed control system 112 can optionally be performed on or adjacent to manipulator assembly 102, another portion of the data processing can optionally be performed at master assembly 106, and other portions of the data processing can optionally be performed at other data processing circuits. The at least one computer processor or the two or more data processing circuits of control system 112 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperated medical systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via one or more openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The sensor system 108 may implement one or more electromagnetic (EM) sensor, fiber optic sensors, and/or other sensors to register and display a medical instrument together with preoperatively recorded surgical images. For example, U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such sensor system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The total number of teleoperational manipulator assemblies included in the teleoperated medical system will depend on a number of factors including the surgical procedure and the space constraints within the operating room. When implemented as multiple units, master assembly 106 may be collocated or positioned in separate locations. Multiple master assemblies allow more than one operator to control one or more teleoperational manipulator assemblies in various combinations.

Figures 2A, 2B:
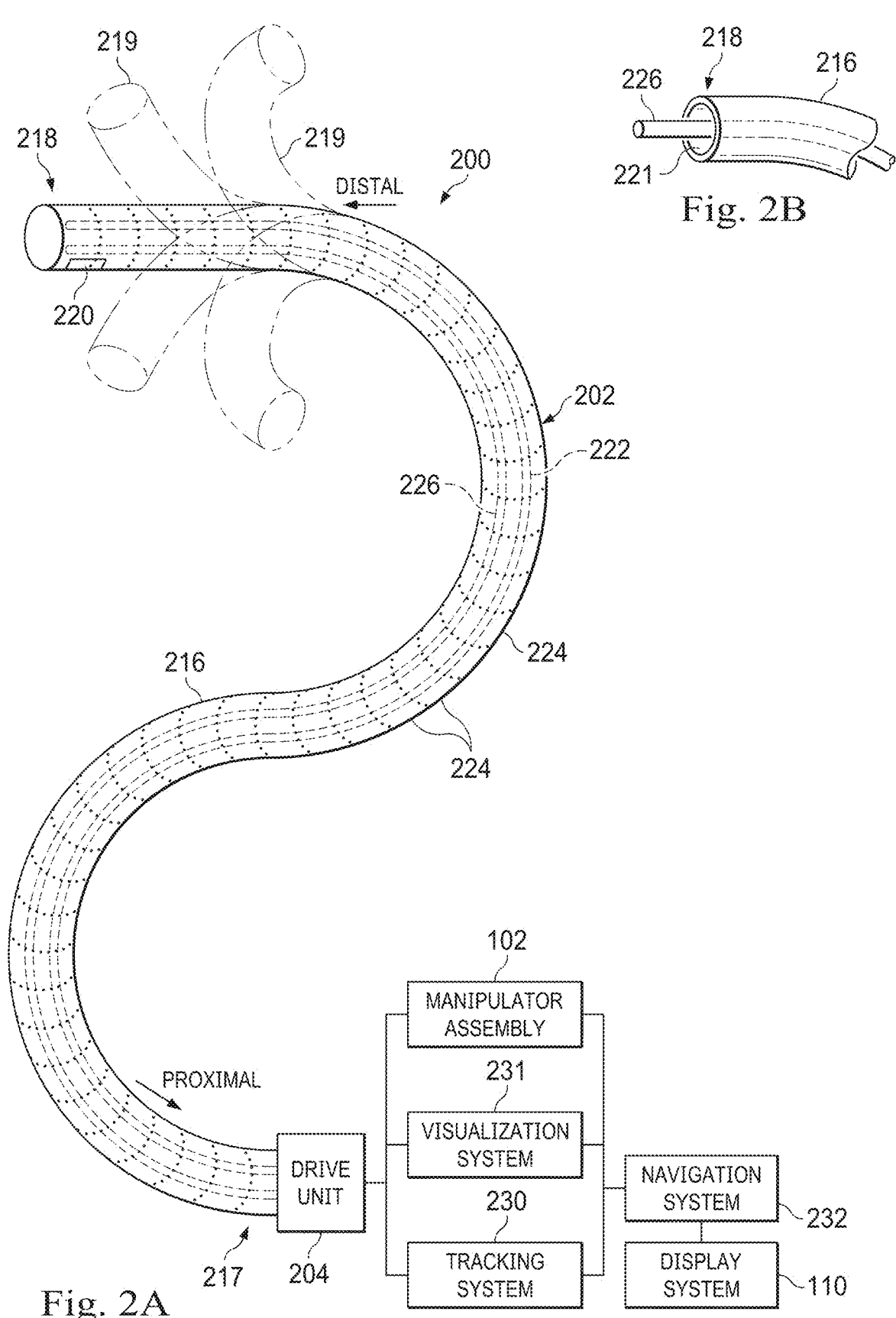
FIG. 2A is a simplified partial-schematic diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end 218 (which may be a tip portion in some embodiments). In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the at least one processor or the two or more data processing circuits of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions of the optical fiber may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties.

Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over a given interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical tool 226. FIG. 2B is a simplified diagram of flexible body 216 with medical tool 226 extended according to some embodiments. In some embodiments, medical tool 226 may be used for procedures such as surgery, biopsy, ablation, illumination, irrigation, or suction. Medical tool 226 can be deployed through channel 221 of flexible body 216 and used at a target location within the anatomy. Medical tool 226 may include, for example, image capture probes, biopsy instruments, laser ablation fibers, and/or other surgical, diagnostic, or therapeutic tools. Medical tools may include a single working member such as a scalpel, a blunt blade, an optical fiber, an electrode, and/or the like. Other medical tools may include, for example, forceps, graspers, scissors, clip appliers, and/or the like. Other medical tools may further include electrically activated tools such as electrosurgical electrodes, transducers, sensors, and/or the like. In various embodiments, medical tool 226 is a biopsy instrument, which may be used to remove sample tissue or a sampling of cells from a target anatomic location.

Medical tool 226 may be used with an image capture probe also within flexible body 216. In various embodiments, medical tool 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical tool 226 may itself be the image capture probe. Medical tool 226 may be advanced from the opening of channel 221 to perform the procedure and then retracted back into the channel when the procedure is complete. Medical tool 226 may be removed from proximal end 217 of flexible body 216 or from another optional instrument port (not shown) along flexible body 216.

Medical tool 226 may additionally house cables, linkages, or other actuation controls (not shown) that extend between its proximal and distal ends to controllably the bend distal end of medical tool 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286, 644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown in different positions 219, for example, by broken dashed line depictions of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system

200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
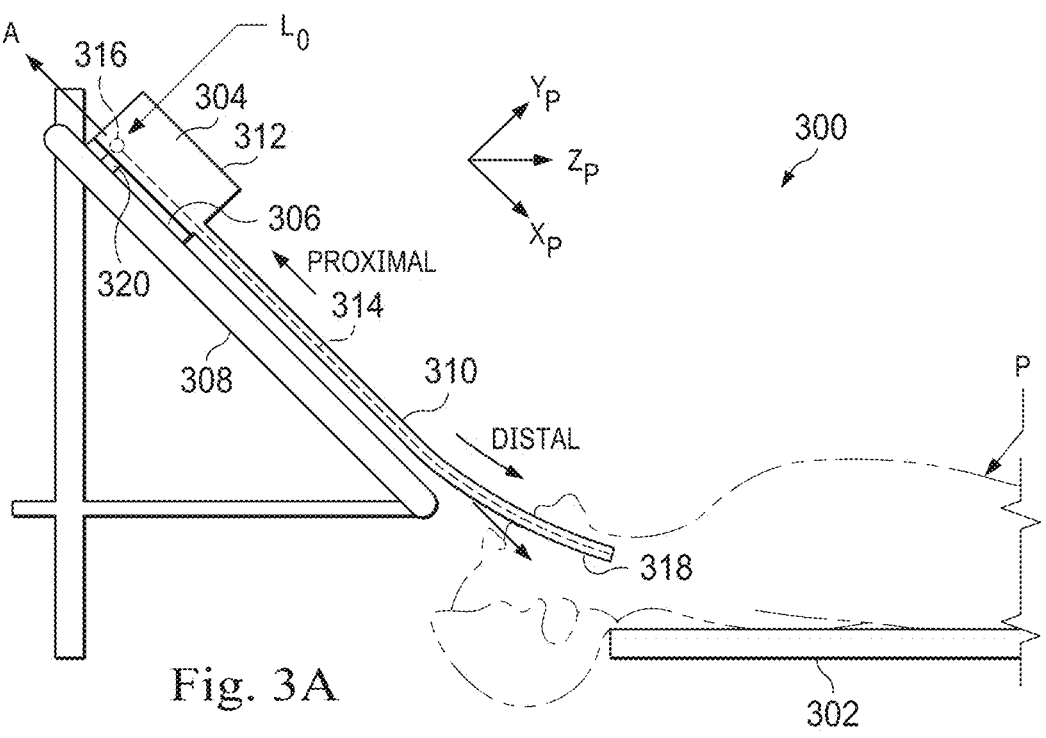
FIGS. 3A and 3B are simplified diagrammatic side views of a patient coordinate space including a medical instrument mounted on an insertion assembly according to some embodiments.
Figure 3B:
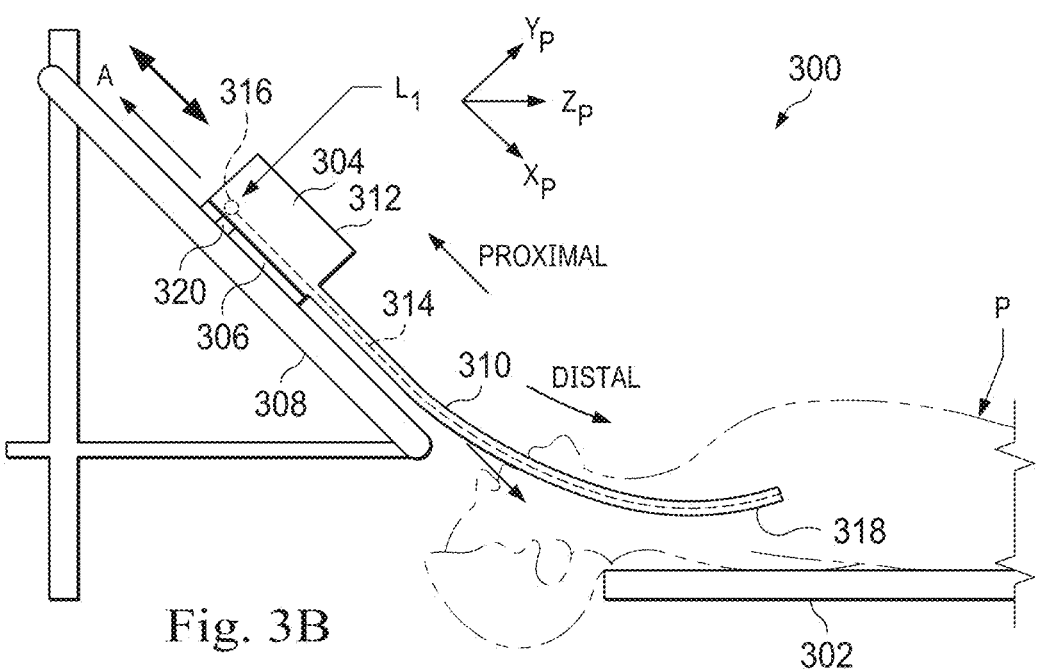

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 (e.g. a medical instrument) can be coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Optical fiber shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308, a component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position $L_0$. In some examples, position Lx may further be used as an indicator of the distance or insertion depth to which distal end 318 of elongate device 310 is inserted into the passageways of the anatomy of patient P.

To safely and effectively operate a medical instrument system, medical tools may need to be properly installed, positioned, identified, authenticated and/or otherwise received and recognized when mounted to a system, such as manipulator assembly 102, or inserted into a receiving member, such as medical instrument system 200. As disclosed herein, a tool recognition assembly at the receiving member may be used to detect the presence or absence of targets on the tool to detect and develop insertion signatures for each inserted tool. Based on of the detected and developed insertion signatures, various options for operating the tool or medical instrument system may be enabled or disabled. Although many of the embodiments described herein describe the receiving member as a catheter, the tool recognition systems and methods described are suitable for use with any type of tool and receiving member. In one example described in detail below, the tool recognition assembly may be used to determine a mode of operation based on whether or not a medical tool is fully inserted into a catheter assembly. If, for example the tool is a camera probe, the tool recognition assembly may be used to determine whether the probe is properly seated in a delivery catheter before the catheter may be operated in a driving mode and advanced into the patient. Allowing the catheter to advance blindly without ensuring that the camera probe is properly positioned may cause injury to the patient which can be prevented by use of the tool recognition assembly. Once at a destination, the camera probe may be withdrawn from the catheter to make room for a different medical tool. Withdrawal of the camera probe may leave the physician unable to view the internal body structures to be treated or assessed. Consistent with the teachings of the present disclosure, the tool recognition assembly may detect that the camera has been removed and may enter a safe mode in response. While in the safe mode, one or more functionalities of a control system (e.g., control system 112 in FIG. 1) may be limited or disabled. For example, catheter flexibility and/or the speed at which adjustments to catheter position may be made can be limited. Such limitations are expected to reduce the likelihood of patient injury resulting from blind adjustments to instruments remaining inserted in the patient after withdrawal of the camera. Accordingly, implementation of the teachings of the present disclosure is expected to improve the safety of minimally invasive procedures. A tool recognition assembly may also be used to recognize counterfeit or otherwise unauthorized devices (such as a device manufactured by an unauthorized manufacturer). A tool recognition assembly may also be used to identify tool types (e.g. needles, ablation tools, cutter, graspers, etc.), and based on the recognition of tool type, control mode alternations or tool behavior modifications may be implemented.

In some embodiments, a tool may be installed in a catheter, and the tool can include an imaging sensor for collecting images, for example, during a procedure. If the tool, inserted through the catheter lumen, is not rigidly coupled to the catheter, the tool can rotate relative to the catheter. To prevent this rotation, a physical key system can be provided on the catheter and tool in combination. For example, an inner wall of the catheter may be provided with a longitudinally extending physical groove formed with a rectangular cross section. A physical key, with a similar but slightly smaller cross-section than the groove, can protrude from an outside of the distal portion of the tool. To install the tool in the catheter, the physical key must be aligned with the groove. Therefore, when the physical key is aligned with the groove, the tool is oriented with the catheter, such that the tool rotates with the catheter during installation of the catheter in a patient's anatomy. This physical key system can help prevent the tool from rotating relative to the catheter but may also have some disadvantages.

Since the key on the tool is only aligned with the catheter at one orientation, the tool must be positioned so as to properly align the physical key with the matching groove. This can be challenging at times, and is at least a nuisance. Additionally, since the catheter may have some amount of flexibility and some degree of imperfect fit for the physical key system (e.g. due to manufacturing tolerances), the tool may be able to overcome the restraint of the physical key system to rotate or flip within the catheter when a sufficient torque differential occurs between the tool and the catheter. The rotation of the tool within the catheter can result in the physical key becoming jammed in the catheter, possibly rendering the system unusable. Furthermore, providing the physical key on the tool and the groove in the catheter can add cost to the product.

Eliminating the protruding physical key from the tool and the groove from the inside of the catheter can eliminate the insertion alignment, jamming, and cost issues described above. Instead of a protruding physical key, a real-time control system based on vision feedback can be used to measure a rotational offset of the tool relative to the catheter. Images captured during a procedure can be adjusted to remove the rotational offset so the resulting adjusted images create the appearance that the tool is rotationally aligned with the catheter.

Figure 4:
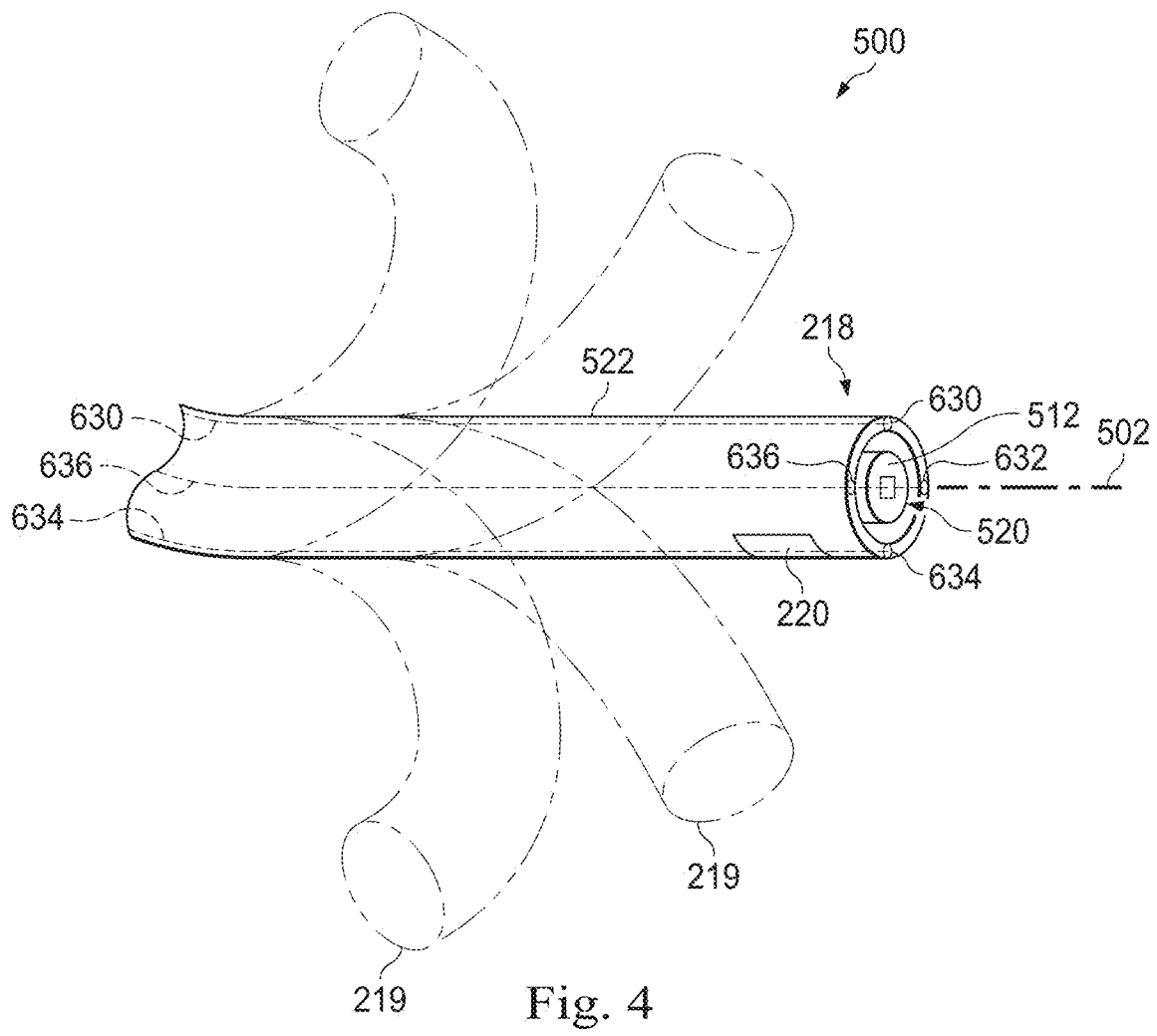
FIG. 4 is a simplified partial-schematic diagram of a distal portion of a catheter assembly according to some embodiments.

Referring now to FIG. 4, a simplified partial-schematic diagram of a distal portion of a catheter assembly 500 is shown. The catheter assembly 500 may be similar to medical instrument system 200, as previously described. A tool 520 is installed in a catheter 522, with the distal end 516 of the catheter 522 aligned with a distal end 512 of the tool 520.

The catheter 522 can be a steerable catheter. Tension can be selectively applied to control cables (also known as pull cables) 630, 632, 634, 636 to provide articulation of the distal end 218 with 2-degrees of freedom (i.e. forward-backward, right-left). The four control cables can provide a cable pair 630/634, and a cable pair 632/636, with each cable of a pair being oppositely arranged (i.e. approximately 180 degrees) from each other around the circumference of the catheter. Each pair can be circumferentially separated by 90 degrees. Therefore, the four control cables 630, 632, 634, 636 are spaced circumferentially around the catheter at substantially a 90 degree spacing from adjacent control cables (e.g. cable 630 can have a 90 degree spacing between it and the two adjacent cables 632, 636, and a 180 degree spacing from the cable 634).

The cable pairs 630/634, 632/636 can bend the distal end 516 of the catheter 522 forward-backwards and right-left (e.g. some articulated positions 219 of the distal end 516 are shown). Combinations of right-left and forward-backward bends can result in a rotation of the catheter relative to the tool 520 about a central axis 502. Rotation of the catheter 522 relative to the tool 520 can cause an imaging sensor in the tool 520 to capture images that are not aligned with orientation of the catheter 522 and its cable pairs. If the orientation of the images becomes decoupled from the orientation of the catheter and cable pairs, the images may become ineffective as an aid to the user in steering the catheter via the cables. The images, rotationally offset from the catheter control cables, may be misinterpreted, causing incorrect manipulations of the control cables and undesired articulations of the catheter's distal end 516. The current disclosure eliminates (or at least minimizes) these issues by providing images to the user that have been adjusted to remove the rotational offset.

An algorithm, as described below, may determine a rotational offset of the tool 520 relative to the catheter 522. Once the rotational offset is known, the control system 112 may rotate the image for display on the user screen to properly present visual feedback to the user, and the control system 112 may map user commands to the pull cables to correct the movement of the catheter 522 to correlate with the displayed images. The amount of tension in the pull cables can be controlled by the control system 112. The tension on the pull cables can be determined by keeping a minimum tension in all pull cables at all times and then adjusting the tension to react to an input from an input device commanding the catheter in a particular direction.

Figure 5:
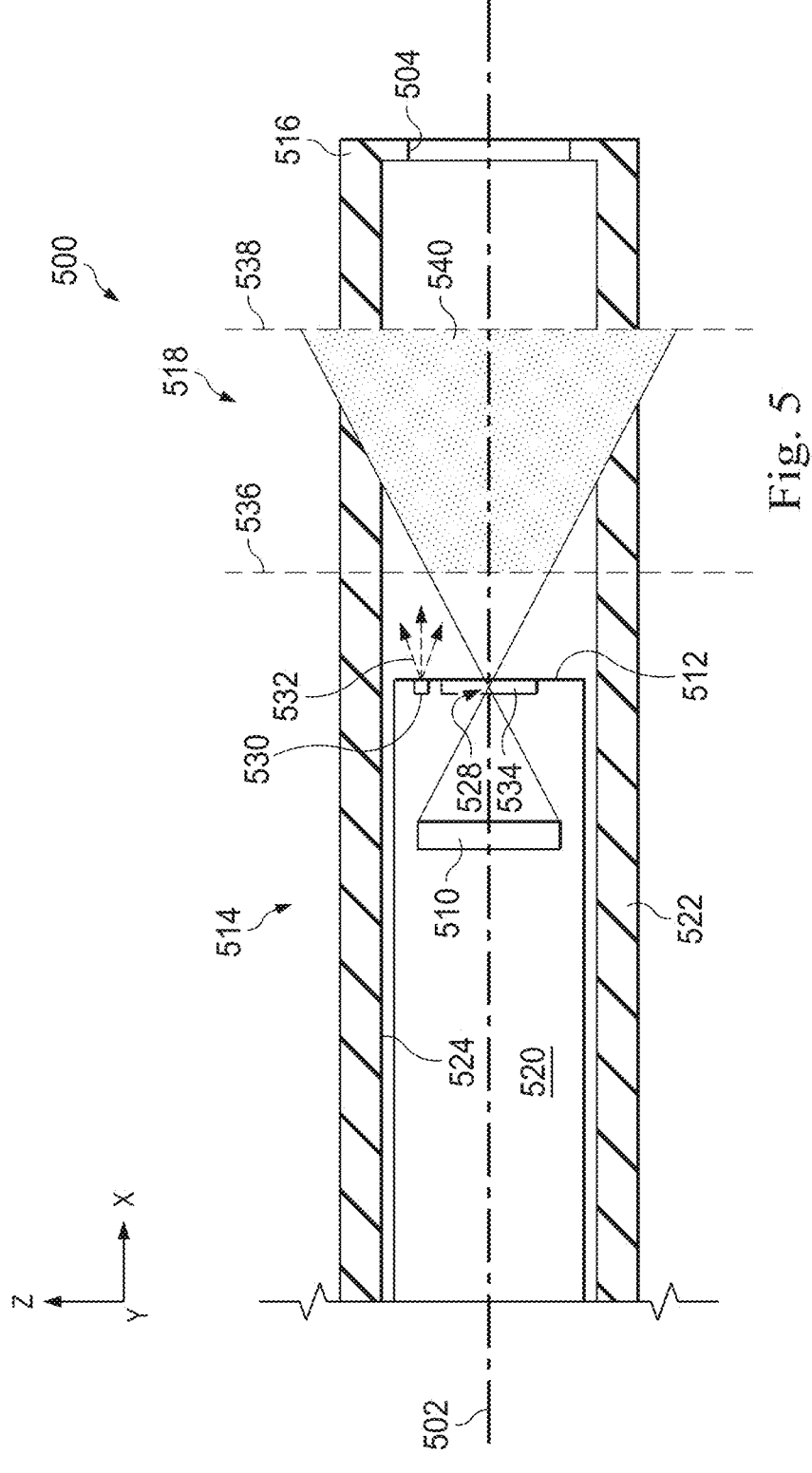
FIG. 5 is a simplified partial cross-sectional view of a distal portion of a catheter assembly according to some embodiments.

Referring to FIG. 5, a simplified partial cross-sectional view of a distal portion 518 of a catheter assembly 500 is provided. An X-Y-Z coordinate reference is given for purposes of discussion and does not limit the disclosure. Generally, the X-axis can be parallel to the central axis 502, with the Y- and Z-axes being perpendicular to the central axis 502. A tool 520 is partially installed in a lumen 524 and spaced away from the distal end 516 of the catheter 522. An imaging sensor 510 can be positioned in the distal portion 514 of the tool 520 and has a viewable region 540 that extends from the distal end 512. However, it should be understood that the imaging sensor 510 can be positioned at other locations in the tool 520. For example, the imaging sensor 510 can be positioned at a proximal portion of the tool 520 with an optical transmission system (e.g. an optical waveguide) that transmits light from the distal end 516 to the imaging sensor 510. A lens 534 can be positioned at the distal end 512 and have an optical center of the lens 528. The lens 534 can provide a viewable region 540 in front of the imaging sensor 510, where the near point 536 and the far point 538 are extreme ends of the viewable region 540. It should be understood that the viewable region 540 is not necessarily to scale and that the far point 538 of the region 540 can extend farther away or closer than indicated in FIG. 5. Also, the near point 536 can be closer or farther away than in FIG. 5. The imaging sensor 510 may capture both high frequency light (such as light within a human visual spectrum) and low frequency light (such as infrared light). An optical source 530 can be disposed at the distal end 512 of the tool 520 and/or disposed at the distal end 516 of the catheter 522. The optical source 530 can generate emitted light (or illumination light) 532 to illuminate the lumen 524 as the tool 520 is being inserted into the catheter 522, and illuminate objects outside of the lumen 524 when the tool 520 is fully inserted (i.e. inserted to a position in the catheter 522 that allows full functionality of the tool 520). In some embodiments, the illumination light 532 may be red, blue, green, yellow, or any other suitable color of light.

Figure 6:
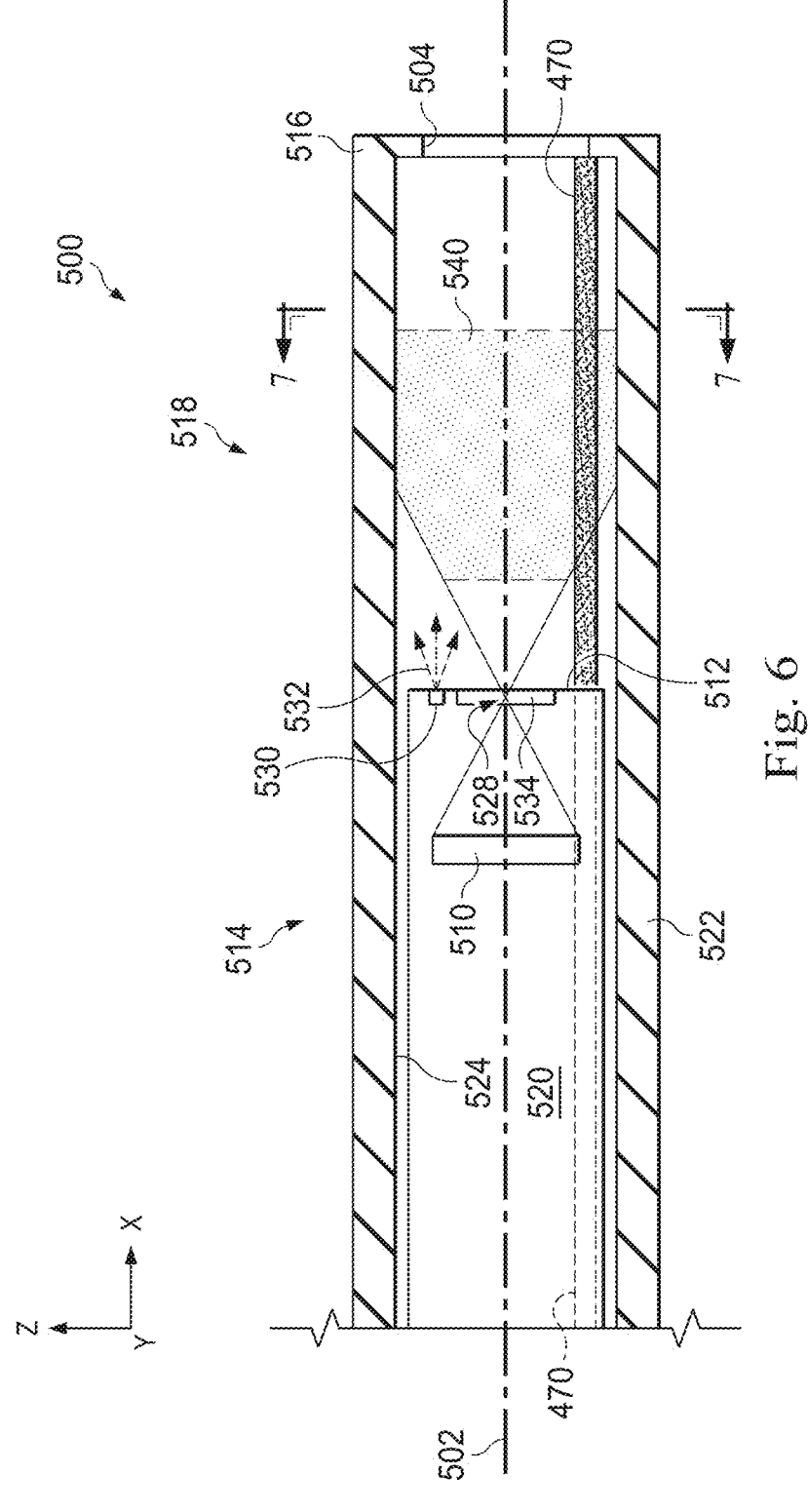
FIG. 6 is a simplified partial cross-sectional view of a distal portion of a catheter assembly with a longitudinal marking according to some embodiments.

Referring now to FIG. 6, a simplified partial cross-sectional view of a distal portion 518 of the catheter assembly 500 is shown. In this embodiment, a viewable feature 470 in the form of a longitudinal marking extending parallel to the central axis 502, is formed on an interior surface of the lumen 524 and can be a contrasting feature to the rest of the interior surface of the lumen, e.g. a different color, different texture, etc. The rest of the surface can be referred to as a background layer of the lumen. The marking (or viewable feature) 470 provides sufficient contrast between the background layer (e.g. a background color) so that the marking can be seen in images captured by the imaging sensor 510 within the catheter 522. The viewable region 540 gives the imaging sensor 510 a 360 degree view of the interior surface of the lumen 524 ahead of the distal end 512 of the tool 520. The longitudinal marking 470 is formed at a pre-determined angular position in the lumen 524. Therefore, the angular relationship between the marking 470 and the catheter 522 is fixed. When the imaging sensor 510 captures an image within the lumen 524, the longitudinal marking 470 will show up in the images at an angular position in the 360 degree view of the imaging sensor 510. The longitudinal marking 470 can be any feature that is visible on the inside surface of the lumen 524 and is distinguishable from the rest of the inner surface of the lumen 524. Also, the longitudinal marking 470 can occupy a small circumferential distance of the inner surface when compared to the full circumferential distance around the inner surface. Therefore, the longitudinal marking can be referred to as a longitudinal stripe that extends along at least a portion of the lumen's interior surface.

As the tool 520 is being inserted into the catheter 522, the imaging sensor 510 can continuously capture images from within the lumen 524 to be used by the control system 112 for determining an orientation of the longitudinal marking(s) (and thus an orientation of the tool 520) within the lumen 524. At any time, an orientation of the longitudinal marking(s) can be determined by analyzing a plurality (e.g. approximately 50) of the most recent images captured. The most recently captured images include the latest orientation information of the longitudinal marking(s) and the plurality of images can be processed to provide increased confidence that the results of the tool orientation determination are accurate. When the tool 520 is fully inserted into and seated with the catheter 522, the tool 520 may no longer be able to view the longitudinal marking(s) 470 on an inside of the catheter 522. Therefore, further collection of images for orientation determination is no longer beneficial and can be stopped. The tool 520 can then be used for other tasks, such as collecting images of a patient's anatomy viewed from the distal end of the catheter 522.

Figure 7:
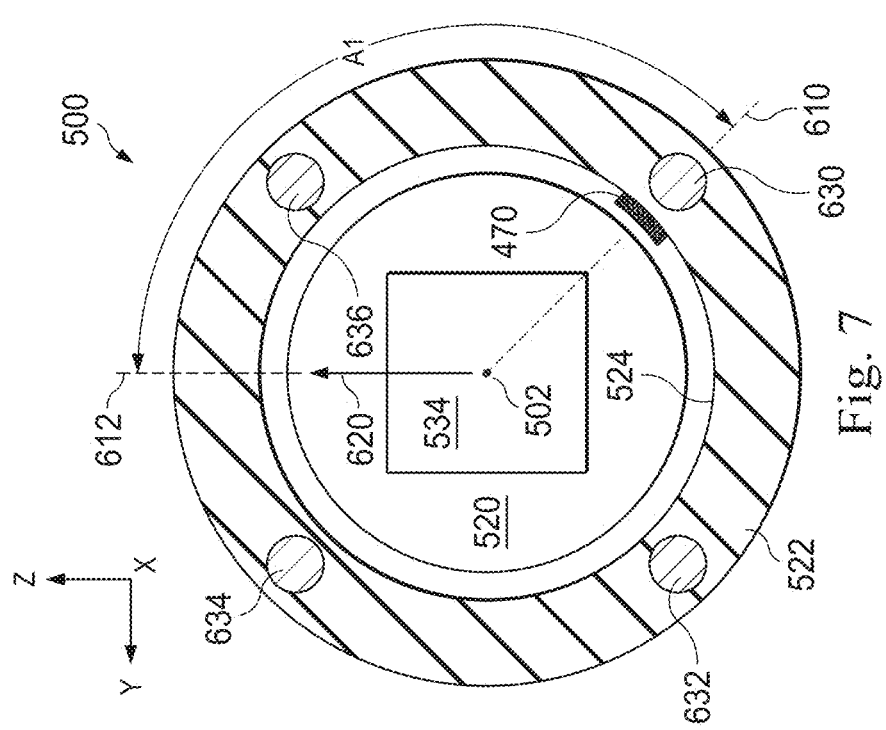
FIG. 7 is a simplified cross-sectional end view of the distal portion of the catheter assembly of FIG. 6 according to some embodiments

FIG. 7 illustrates a simplified cross-sectional end view at the distal portion 518 of the catheter assembly 500. The tool 520 may become rotated relative to the catheter 522 and the catheter cables 630-636, which, in some embodiments, may be control cables (e.g. during installation of the tool 520 and/or due to other factors, such as manufacturing tolerances). An angular position 610 indicates the 0 (zero) degree angular position of the catheter 522 relative to the catheter and the angular position 612 indicates the 0 (zero) degree angular position of the tool 520 relative to the tool. The resulting rotational offset A1 (or angular offset) can be seen in captured images from within the lumen 524 by the angular position of the longitudinal marking 470 within the 360 degree view of the imaging sensor 510. It should be understood that the rotation can be in the opposite direction (i.e. clockwise) to arrive at the angular position 612 shown in FIG. 7. The arrow 620 indicates the angular position of the top-middle of the imaging sensor, and therefore indicates the top-middle of images captured by the imaging sensor 510.

Figure 8A:
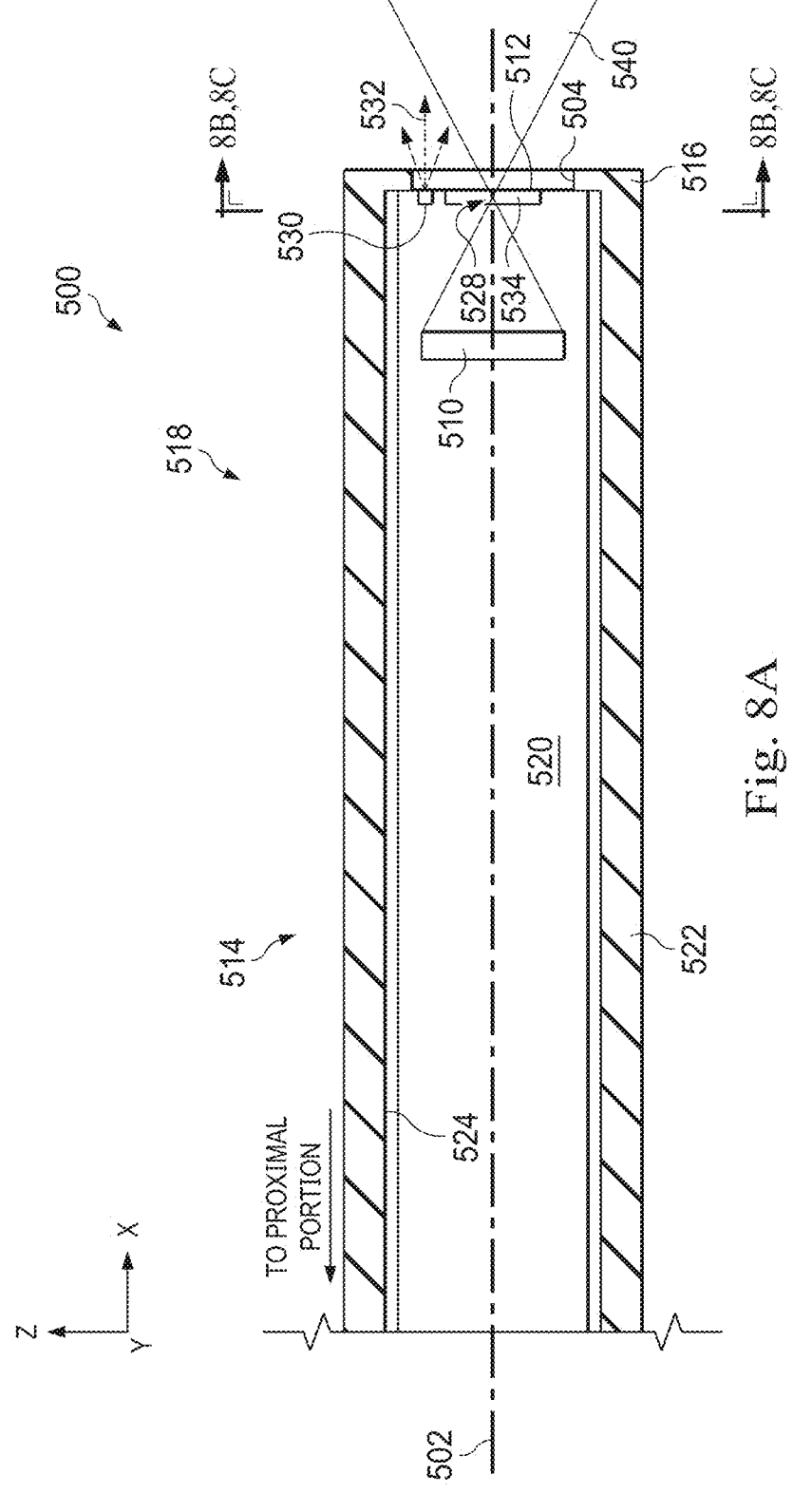
FIG. 8A is a simplified partial cross-sectional view of a distal portion of a catheter assembly according to some embodiments.

Referring now to FIG. 8A, a simplified partial cross-sectional view of a distal portion 518 of a catheter assembly 500 is shown. This catheter assembly 500 is similar to the catheter assembly in FIG. 5, except that the distal end 512 of the tool 520 engages the distal end 516 of the catheter 522. The optical source 530 provides illumination light 532 for objects viewable through the opening 504.

Figures 8B, 8C:
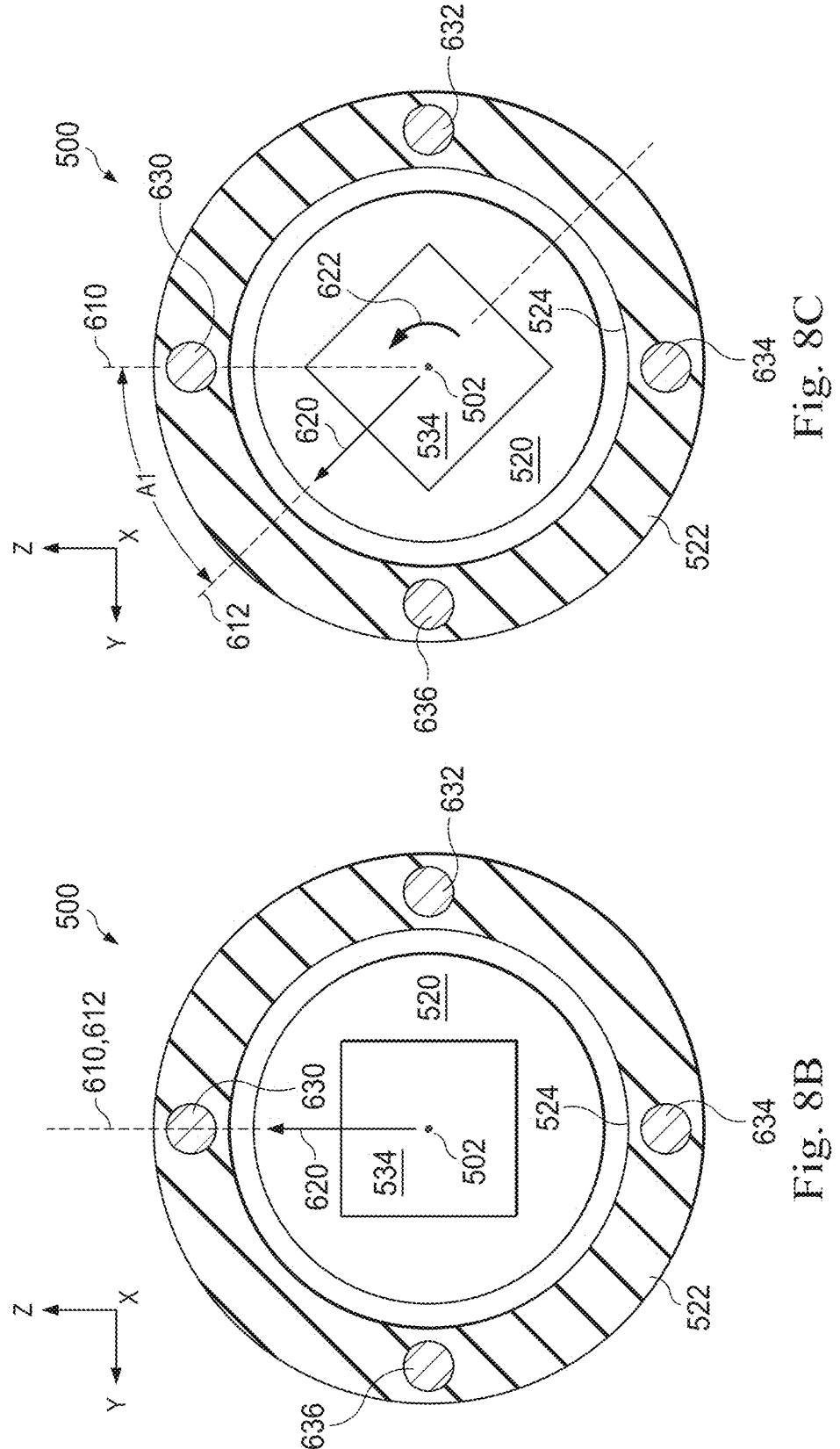
FIG. 8B is a simplified cross-sectional end view of the distal portion of the catheter assembly of FIG. 8A with a tool rotationally aligned with a catheter according to some embodiments.
FIG. 8C is a simplified cross-sectional end view of the distal portion of the catheter assembly of FIG. 8A with a tool rotationally offset from a catheter according to some embodiments.

Referring now to FIGS. 8B-8C, a simplified cross-sectional view of the distal portion 518 of the catheter assembly 500 of FIG. 8A is shown. In this example, the tool 520 and the catheter 522 have circular cross-sections as shown by the FIGS. 8B-8C. The cross-sectional views are viewed in the direction of the viewable region 540 (i.e. looking distally from a distal portion of the tool 520 toward the region 540 as shown by cross-section arrows 8B-8B, 8C-8C). FIG. 8B shows a tool 520 rotationally aligned with the catheter 522. The angular position 612 of the tool 520 is aligned with the angular position 610 of the catheter 522. The arrow 620 again indicates the top-middle position of the imaging sensor 510 relative to the central axis 502. FIG. 8C shows that the angular rotation 622 has rotated the tool 520 relative to the catheter 522 by a rotational offset A1.

Figure 9B:
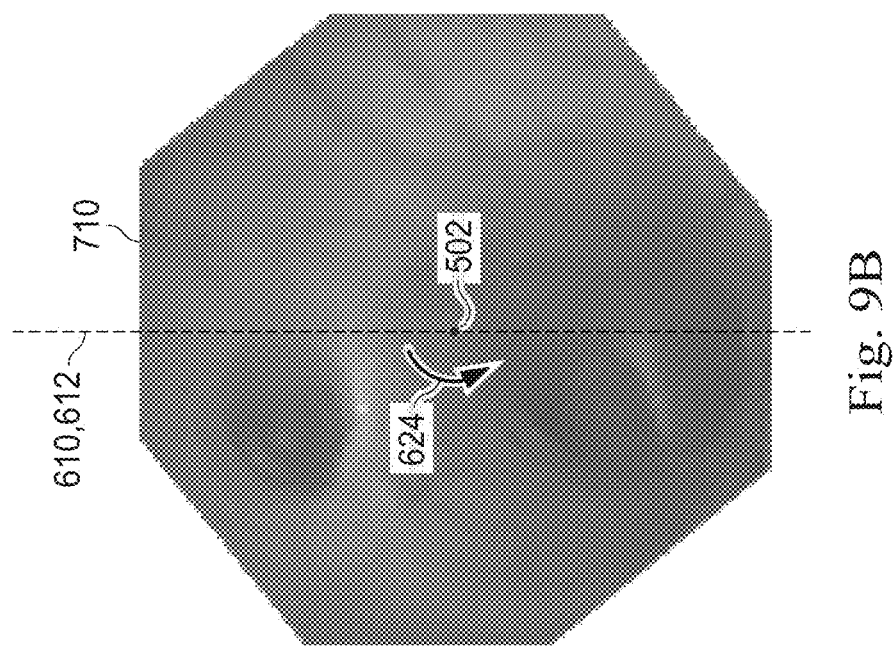
FIG. 9B is a representative image of the image of FIG. 9A with the rotational offset removed according to some embodiments.
Figure 9A:
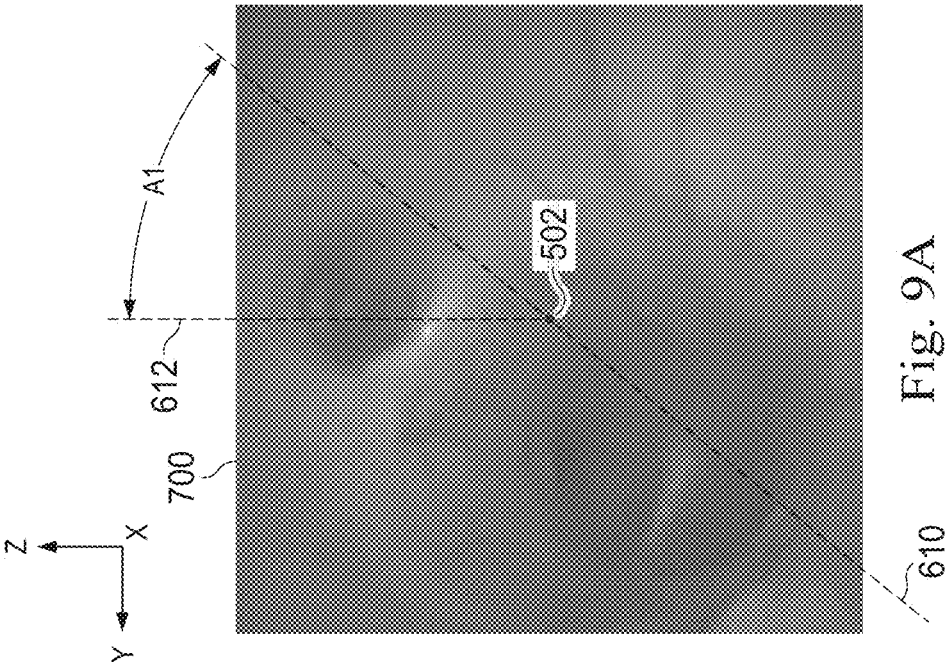
FIG. 9A is a representative image taken by the tool of the catheter assembly of FIG. 8C with the tool rotationally offset from the catheter according to some embodiments.

Referring now to FIG. 9A, a representative image taken by the tool 520 of the catheter assembly 500 of FIG. 8C is shown. The tool 520 is offset from the catheter 522 by a rotational offset A1, which can result in a captured image 700 of a patient's anatomy as shown in FIG. 9A. The image 700 is taken by the imaging sensor 510 that is at a rotational offset A1 relative to the catheter 522. The angular position 610 again indicates the 0 (zero) degree angular position of the catheter 522, with angular position 612 again indicating the 0 (zero) degree angular position of the imaging sensor 510. Since the imaging sensor is rotationally offset, the captured image 700 is not aligned with the control cables, thus leading to inaccurate steering of the catheter 522, if the image is not corrected to produce an aligned image of the anatomy.

Referring now to FIG. 9B, a representative image 710 is shown that represents the image 700 with the rotational offset A1 removed. The control system 112 can receive the captured image 700 and perform a rotation 624 of the image 700 to remove the rotational offset A1. The rotation 624 can rotate the angular position 610 of the image 700 an angular distance of A1, such that the angular position 610 and the angular position 612 are aligned, thereby producing a modified image 710, which can then be displayed on a user display. With properly aligned images, the users can perform procedures using the control cables 630-636 as if the imaging sensor 510 was aligned with the catheter 522.

Figure 10A:
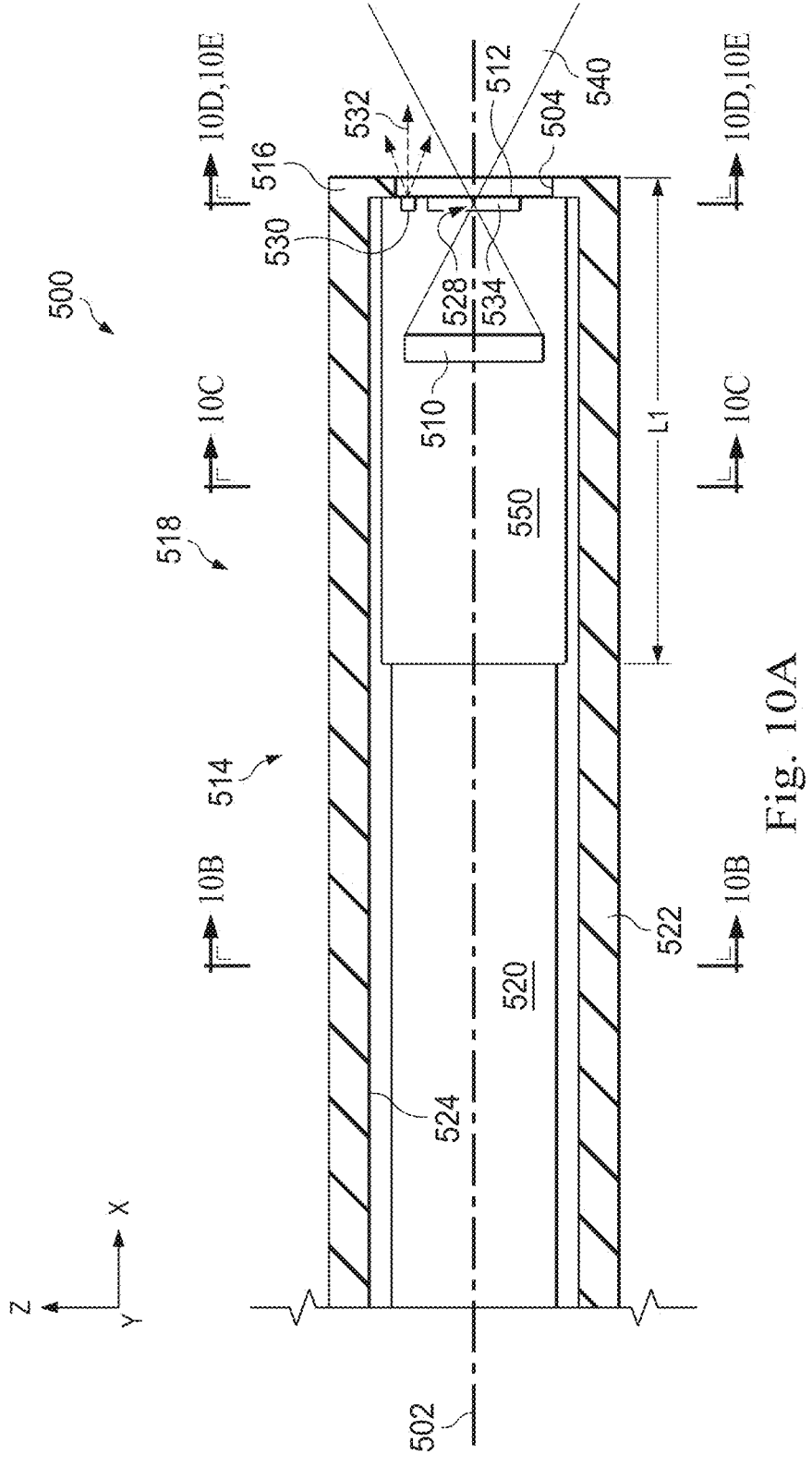
FIG. 10A is a simplified partial cross-sectional view of a distal portion of a catheter assembly with distal portion of a tool having a square cross-section according to some embodiments.

Referring now to FIG. 10A, a simplified partial cross-sectional view of a distal portion 518 of a catheter assembly 500 is shown. This catheter assembly 500 is similar to the catheter assembly in FIG. 8A, except that a distal portion 550 of the tool 520 has a square cross-section where the rest of the tool 520 has a circular cross-section. The square cross-section of the distal portion 550 matches a square cross-section of the lumen 524 of the catheter 522. The square cross-section of the distal portion 550 and the catheter 522 prevent rotation of the tool 520 relative to the catheter 522, when the distal portion 550 is inserted into the matching square cross-section of the lumen 524. Some rotation may be allowed due to clearances between the tool 520 and the catheter 522, but this is minor, and even this minor relative rotation can be compensated for by using the principles of this disclosure. In various embodiments, the square cross section of the distal portion 550 may be bonded to the portion of the tool 520 with the circular cross-section. In one example, the distal portion 550 may be bonded to the circular portion of the tool 520 approximately 30-40 mm proximal of the distal end 516.

Figures 10B, 10C:
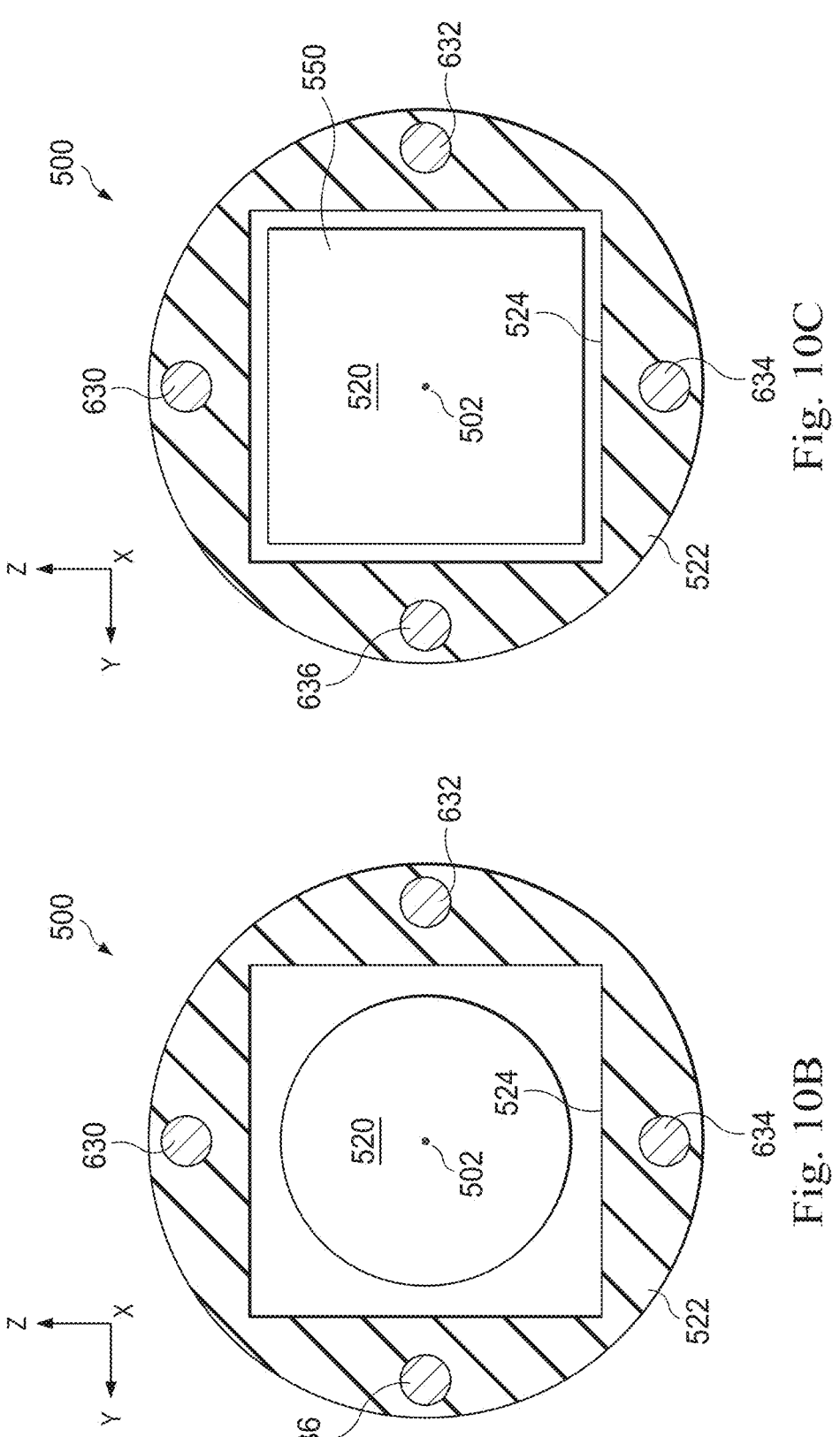
FIG. 10B is a simplified cross-sectional view of the catheter assembly of FIG. 10A according to some embodiments.
FIG. 10C is another simplified cross-sectional view of the catheter assembly of FIG. 10A according to some embodiments.
Figure 10D:
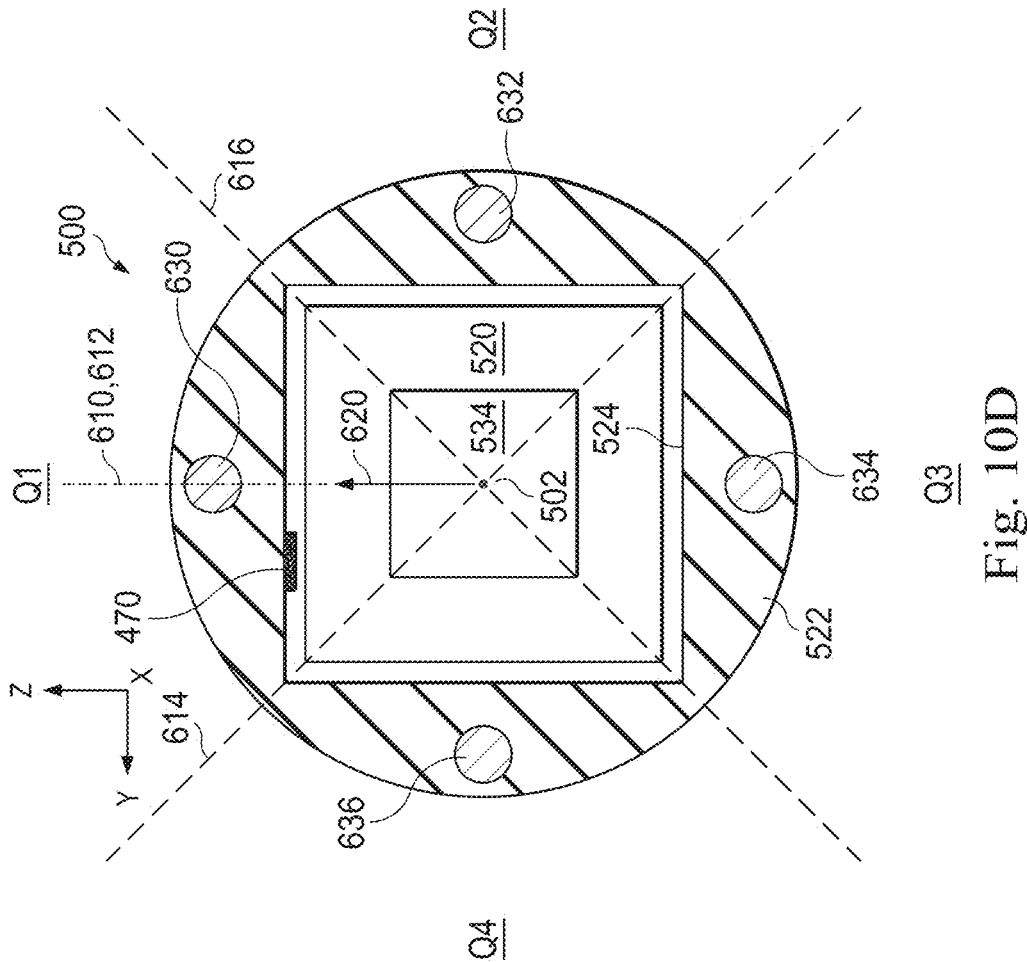
FIG. 10D is a simplified cross-sectional end view of the distal portion of the catheter assembly of FIG. 10A with a tool rotationally aligned with a catheter according to some embodiments.
Figure 10E:
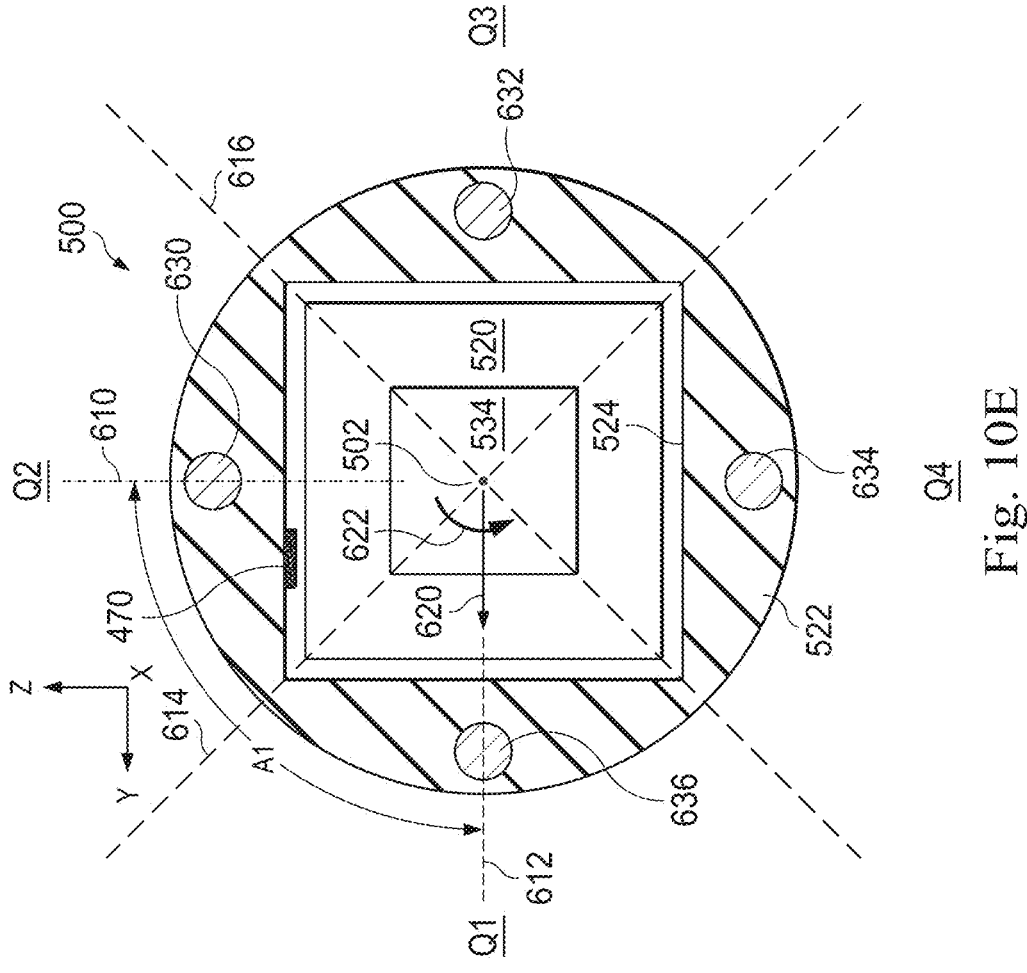
FIG. 10E is a simplified cross-sectional end view of the distal portion of the catheter assembly of FIG. 10A with a tool rotationally offset from a catheter according to some embodiments.

Referring now to FIGS. 10B-10C, a simplified cross-sectional view of the distal portion 518 of the catheter assembly 500 of FIG. 10A is shown. FIG. 10B is a cross-section of a proximal portion of the tool 520 that has a circular cross-section, and the lumen 524 of the catheter 522 has a square cross-section. FIG. 10C is a cross-section of the catheter assembly 500 at the distal portion 550, which shows the distal portion 550 and the lumen 524 with a square cross-section. The cross-sectional views are viewed in the direction of the viewable region 540 (i.e. looking toward the distal end of the catheter 522). FIG. 10D shows a tool 520 rotationally aligned with the catheter 522. The angular position 612 of the tool 520 is aligned with the angular position 610 of the catheter 522. The arrow 620 again indicates the top-middle position of the imaging sensor 510 relative to the central axis 502. FIG. 10E shows the tool 520 offset from the catheter 522 by a rotational offset A1. The angular rotation 622 has rotated the distal portion 550 relative to the catheter 522 by a rotational offset A1.

Because the square cross-section of the distal portion 550 is being inserted into a matching (however, slightly larger) square cross-section of the catheter 522, there are four rotational offset values that are possible, i.e. 0 (zero), 90, 180, and 270 degrees. A first quadrant Q1 of the tool 520 can be defined as the 0 (zero) degree rotational offset. A second quadrant Q2 of the tool 520 can be defined as the 90 degree rotational offset. A third quadrant Q3 of the tool 520 can be defined as the 180 degree rotational offset. A fourth quadrant Q4 of the tool 520 can be defined as the 270 degree rotational offset. The four quadrants can be seen as being divided by lines 614 and 616 as seen in FIGS. 10D and 10E, and can be seen as being quadrants of images captured by the tool 520. Therefore, referring to a quadrant in an image also refers to the same quadrant of the tool 520. The angular rotation 622 indicates that the tool 520 was rotated 90 degrees relative to the catheter 522 when it was inserted into the catheter 522. The catheter 522 can include the viewable feature 470 (as well as additional viewable features such as a longitudinal marking 471 (See FIG. 10G) located 1800 offset from the viewable feature 470), that is viewable by an imaging sensor 510 (not shown) of the tool 520. As the tool 520 is inserted into the catheter 522, captured images from the imaging sensor 510 can indicate which quadrant Q1-Q4 of the captured images that the viewable feature 470 appears in, and the indicated quadrant can be used to determine the rotational offset. The removal of the rotational offset A1 can be performed as described above to produce modified images that are rotationally aligned with the catheter 522. If the viewable feature 471 is also included as shown in FIG. 10G, the captured images can be used to determine the quadrant (Q1-Q4) in which the viewable feature 471 appears, and this additional viewable feature can be used to determine the rotational offset or at least support the determination of the rotational offset A1. However, the viewable features 470, 471 can be positioned at any angular position around the lumen 524 relative to each other, such as positioning the viewable feature 471 at +/−30, 45, 60, 90, 120, 135, 150, and 180 degrees from each other as well as other positions within a range from 10 degrees to 350 degrees relative to each other. One or more additional viewable features (such as more longitudinal markings 470, 471) can also be used and positioned at desired angular positions around the lumen, such as at the angles described above for viewable features 470, 471.

In order to correct the images that have been captured at a rotational offset, the rotational offset A1 must be determined. FIGS. 10G-18B illustrate various embodiments (in addition to the embodiments of FIGS. 7A-7B described herein) for detecting an angular position of tool 520 relative to the catheter 522. The angular position can then be used by the control system 112 to determine the rotational offset A1 at which the images were captured, and the captured images can be corrected by rotating the image in a direction that removes the rotational offset A1. Any of these various embodiments can be used to determine the rotational offset A1. After the rotational offset A1 is determined, the captured images can be corrected as modified images that are rotationally aligned with the catheter 522.

Figure 10F:
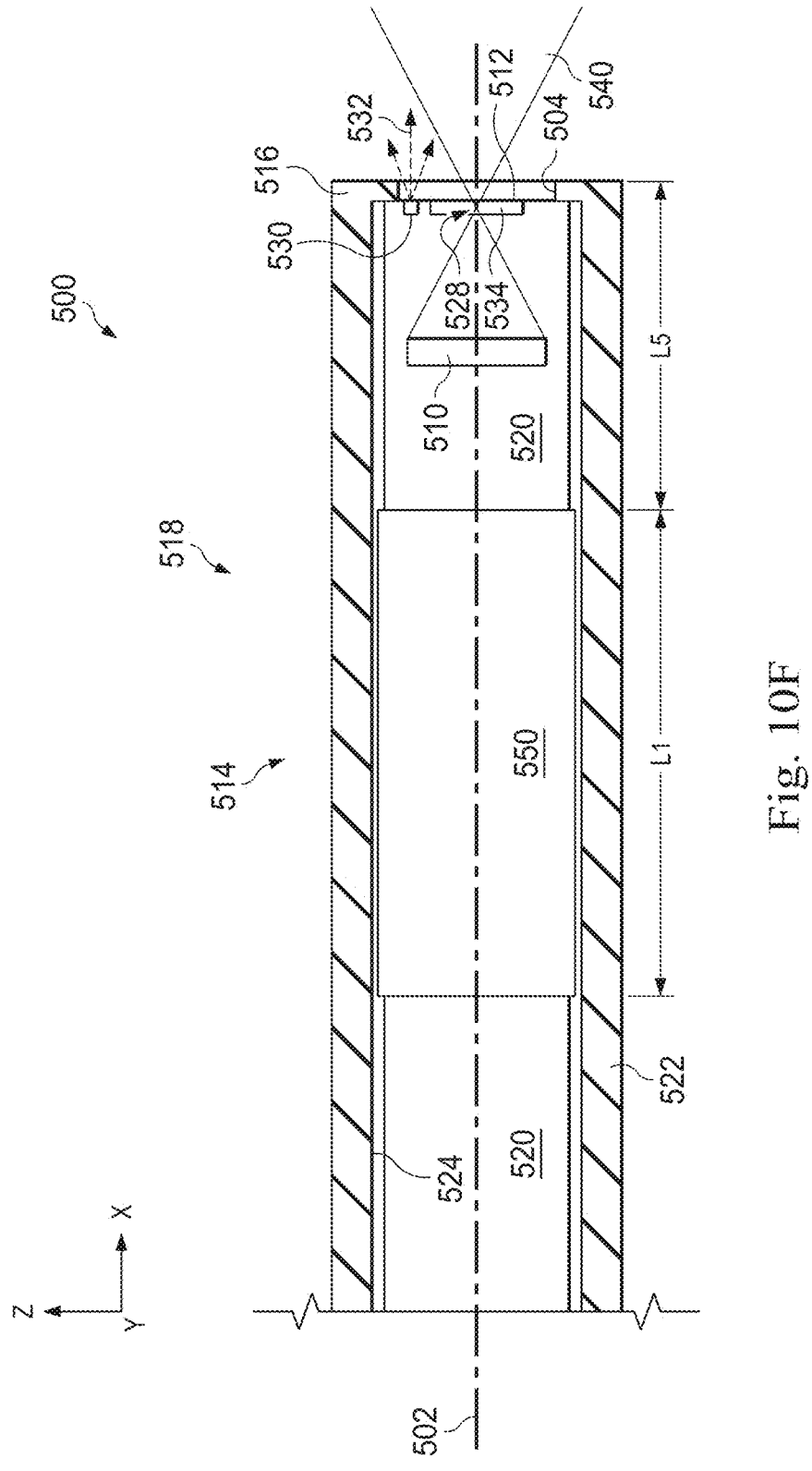
FIG. 10F is a simplified partial cross-sectional view of a distal portion of a catheter assembly with distal portion of a tool having a square cross-section according to some embodiments.
Figure 10G:
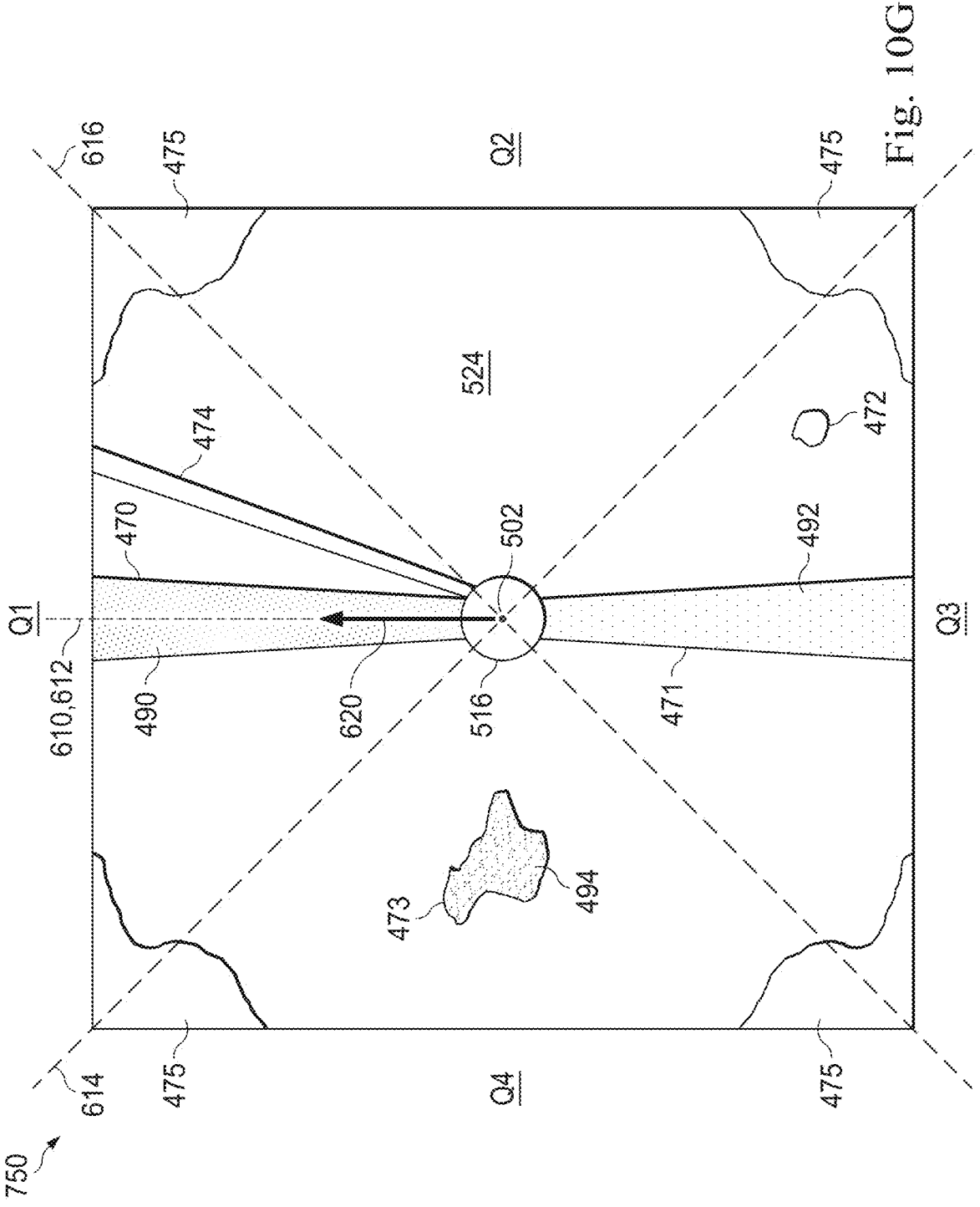
FIG. 10G is a representative image, with one or more longitudinal markings, taken by the tool of the catheter assembly of FIG. 8B having the tool rotationally aligned with a catheter according to some embodiments.

Referring now to FIG. 10F, a simplified partial cross-sectional view of a distal portion 518 of a catheter assembly 500 is shown. This catheter assembly 500 is similar to the catheter assembly in FIG. 10A, except that the distal portion 550 of the tool 520 is spaced away from the distal end of the catheter assembly by a distance L5 and positioned between two other portions of the tool 520 that have a circular cross-section. The distance L5 can range between 50 mm and 200 mm. The distance L5 can be, for example, 50 mm, 60 mm, 70 mm, 80 mm, 90 mm, 100 mm, or 200 mm. The square cross-section of the distal portion 550 matches a square cross-section of the lumen 524 of the catheter 522. The square cross-sections of the distal portion 550 and the catheter 522 prevent rotation of the tool 520 relative to the catheter 522, when the distal portion 550 is inserted into the matching square cross-section of the lumen 524. Some rotation may occur due to clearances between the tool 520 and the catheter 522, but this is minor, and even this minor relative rotation can be compensated for by using the principles of this disclosure. Since the distal portion of the tool 520 can enter the lumen 524 before engaging the square cross section of the distal portion 550, the viewable feature 470 may not be included in a proximal end portion of the catheter 522 to assure the orientation of the viewable feature 470 in the captured images remains consistent with the catheter square lumen.

Referring now to FIG. 10G, a representative image 750 can be captured by the image sensor 510 of FIGS. 10A and/or 10F, and taken with the optical source 530 turned ON. The image 750 indicates that the tool 520 is rotationally aligned with the catheter 522, since angular positions 610 and 612 are aligned. However, if the angular positions are offset by rotational offset A1, the viewable features 470, 471 in the image 750 can be used to determine the offset. In this embodiment, the viewable features 470,471 are longitudinal markings positioned 180° opposite each other on the inside surface of the catheter lumen. The image 750 can also include several viewable objects 472, 473, 474, and 475 in addition to the viewable features 470, 471. The objects can interfere with the offset determination, or at least require additional processing to minimize (or eliminate) the interference. For example, the viewable objects 472, 473 can be blood, other bodily fluids, or tissue located within the lumen 524 or deposited on a surface of the lumen. The viewable object 474 can be a longitudinal marking that can be created by a longitudinal abrasion along the lumen 524 or possibly a longitudinal marking created during manufacturing of the catheter 522. The viewable objects can also be regions of saturated illumination, such as areas 475 at the corners of the image 750. Near the center of the image 750 can be seen the distal end 516 of the catheter 522 at a distal end of the lumen 524. The central axis 502 indicates a central axis of the lumen, but it should be understood that the central axis 502 can be offset from the center of the image 750 due to variations in an imaging direction of the tool 520 as the tool is being inserted into the lumen 524.

To detect and process the viewable features (which in this example are longitudinal markings 470, 471), it may be beneficial to remove (or minimize effects of) the viewable objects 473-475 in the image 750. This can be performed through various techniques, such as filtering, intensity threshold detection, auto-balancing of color distributions, etc. Bright portions in the image 750 that exceed a brightness threshold can be removed by or the brightness may be reduced by alteration of the pixel color and intensity values. Color distributions and saturations of viewable objects in the image 750 can be evened out to form a more uniform color distribution or saturation. Corners of the image 750 (e.g. viewable objects 475) that are saturated with illumination may be filtered out using a mask shaped to remove the corners (e.g. a circular mask, custom form mask, etc.). As described in greater detail below, after removing or at least minimizing, the effects of the viewable objects 472, 473, 474, and 475 on the image processing, the control system can process the modified image(s) to determine orientation of the viewable features 470, 471 with reduced processing time and increased accuracy.

Figure 10H:
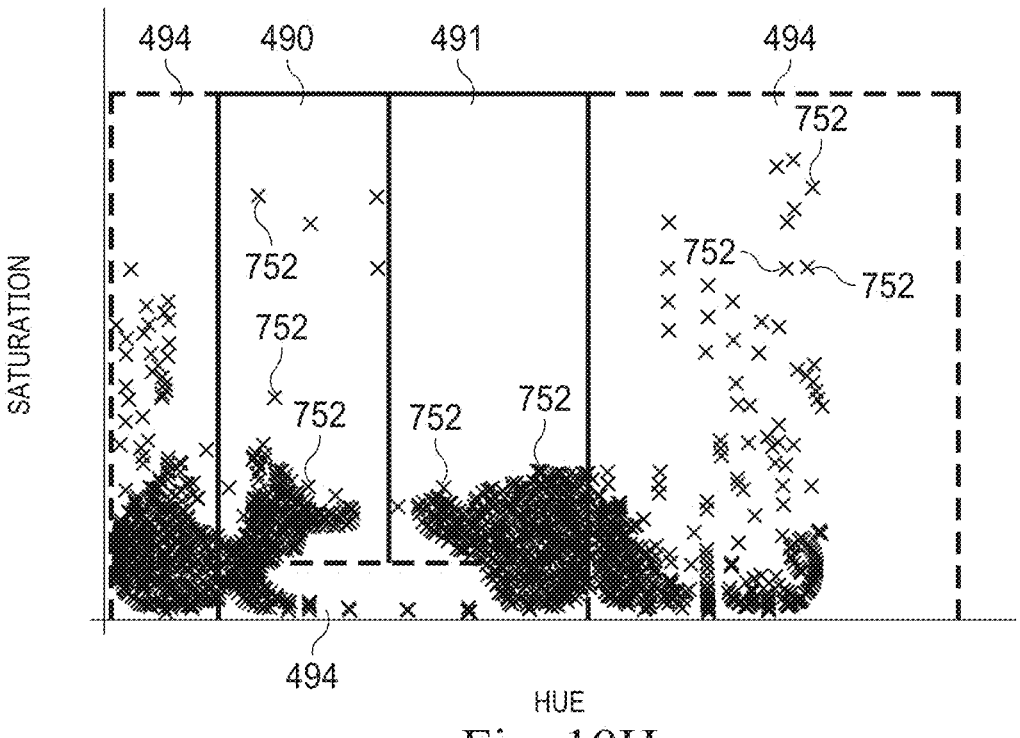
FIG. 10H is a representative plot of saturation vs. hue of pixels in the representative image of FIG. 10G according to some embodiments.

The visibility and detection of the viewable features 470, 471 may be improved using color filtering techniques that remove or minimize colors associated with the natural anatomical environment such as reds so that non-naturally occurring colors (e.g., blues, and yellows) that may be used to form the viewable features are more visible in the modified image. For example, the pixels of the image 750 may be separated into hue saturation values (HSV). FIG. 10H illustrates a representative graph 751 of pixels 752 of the image 750 grouped by hue and measured by saturation. The pixels in area 490 may correspond to yellow pixels (e.g., the color of viewable feature 471) that exceed a predetermined saturation value. The pixels in area 491 may correspond to blue pixels (e.g., the color of viewable feature 470) that exceed a predetermined saturation value. The pixels in areas 494 may correspond to hues and saturation levels outside the hue saturation values associated with the viewable features 470, 471. For example, the pixels in the area 491 may correspond to red pixels or other hues associated with the natural anatomic environment (e.g., the color of blood and other fluid or tissue in the natural environment). To enhance the detection of the yellow viewable feature 471 and the blue viewable feature 470, the pixels in area 494 may be filtered out, neutralized, or otherwise modified so that the processing image removes the color of blood, the allowing the blue and yellow viewable features to be more visible in the processed image.

Figure 10I:
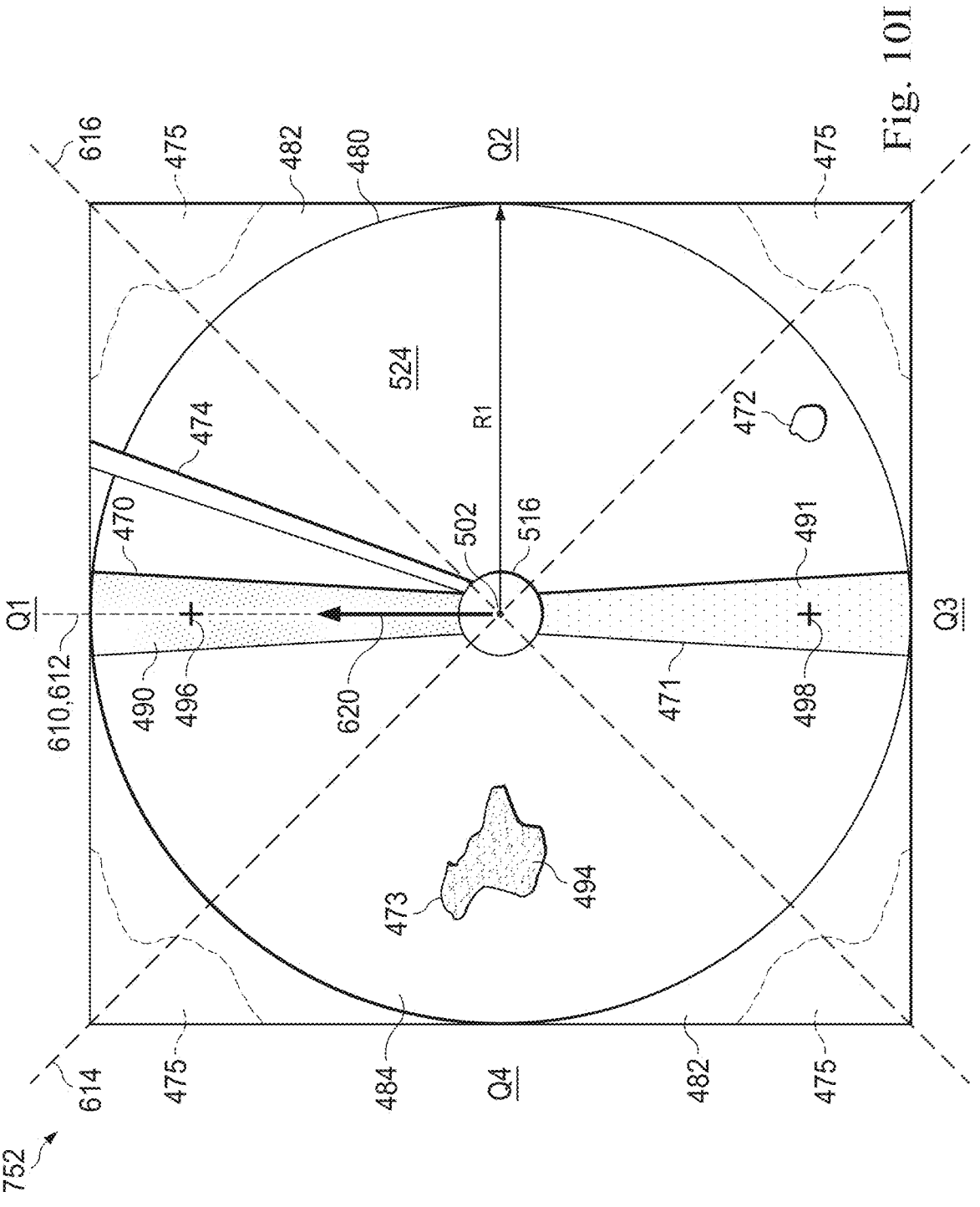
FIG. 10I is the representative image of FIG. 10G with a circular filter applied to the image according to some embodiments.

The visibility and detection of the viewable features 470, 471 may also or alternatively be improved using masking techniques. Referring now to FIG. 10I, a representative image 752 is provided that indicates a modified image 750. A circular filter 480 can be used to filter out the saturated corners 475. The radius R1 of the circular filter can be adjusted as desired to remove the objects 475 as well as remove additional viewable objects (e.g. 472, 473). The viewable objects 472, 473, 474 not filtered by the circular filter 480 may be filtered using other known image processing techniques such as color filtration, thereby leaving the viewable features 470, 471 for determining the rotational offset A1. It should be noted that the rotational offset A1 for image 752 is zero, since the angular positions 610 and 612 are aligned.

After removing (or minimizing effects of) the viewable objects 472, 473, 474, and 475, the control system 112 can determine in which of the quadrants Q1-Q4 each viewable feature 470, 471 is located. In alternative embodiments, the image may be divided into sections other than quadrants. The location of each viewable feature 470, 471 can be determined by detecting the concentration of the HSV of each viewable feature 470, 471 and determining the quadrant in which the HSV concentration is located. The HSV is different for each viewable feature 470, 471 so that each viewable feature 470, 471 can be identified independently from the other. The expected locations of HSV concentrations may also be used to detect the viewable features. For example, in this embodiment the blue visible feature 470 is known to be located directly across the lumen from the yellow visible feature 471 so the hue saturation values for each color would be expected to be concentrated across from each other. The control system 112 can also calculate a centroid of each viewable feature 470, 471 (e.g. centroids 496, 498) and determine the quadrant in which each centroid is located. Determining quadrants Q1-Q4, which are shown separated by lines 616, 614, assumes that the tool 520 and lumen 524 have square cross-sections and that only four possible orientations are possible. However, these techniques can also be used to determine an angular position from 0 to 360 degrees of each viewable feature 470, 471 in the captured image. The rotational offset A1 can be calculated based on the angular positions of the one or more viewable features 470, 471.

Figure 10J:
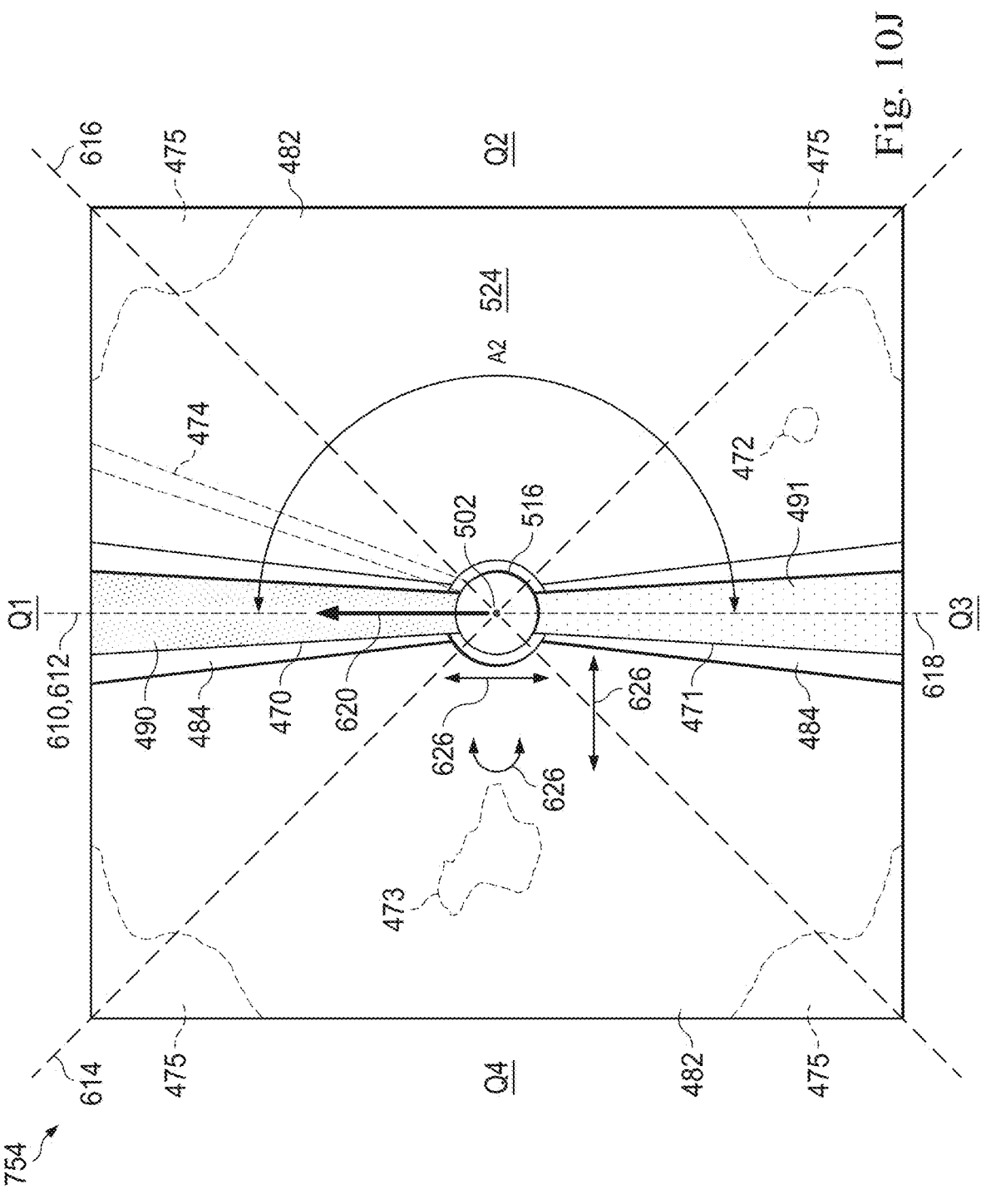
FIG. 10J is the representative image of FIG. 10G with a custom-shaped filter applied to the image according to some embodiments.

Referring now to FIG. 10J, a representative image 754 is provided that indicates a modified image 750. A custom formed filter region 484 is provided to filter out most (if not all) of the viewable objects 472, 473, 474, and 475 from the image 750. The filter region 484 is shown to be slightly larger than the viewable features 470, 471 and the distal end 516. The filter region 484 can be larger or smaller than shown in the figures, and can be of various shapes and sizes as needed to provide a desired filtering effect on the captured images. The shape can be determined by the known shape of the combination of the viewable features 470, 471 and the distal end 516. This filter region 484 can be translated up/down and left/right, and rotated, as indicated by arrows 626, to align with the viewable features 470, 471. The alignment of the filter region 484 with the viewable features 470, 471 can be determined when the HSV of the pixels in the filter region 484 exceed a saturation threshold. Then the angular position of each viewable feature 470, 471 can be determined as described above. It should be understood that more or fewer viewable features 470, 471 can be used to determine the orientation of the tool 520 relative to the catheter 522. Also, as stated above, the angular offset A2 from one viewable feature (e.g. 470) to a second viewable feature (e.g. 471) can be angular offsets other than 180 degrees.

Figure 10K:
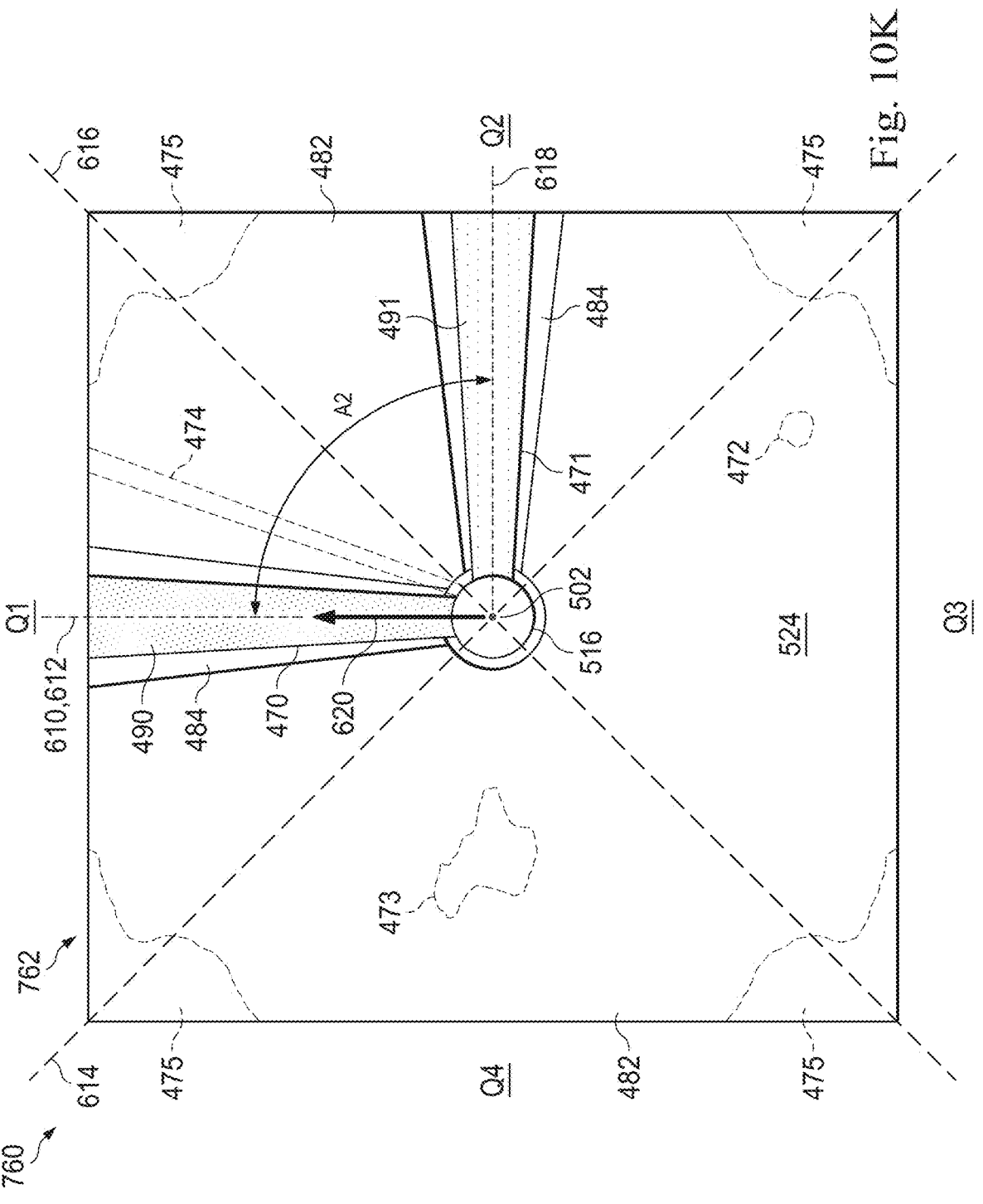
FIGS. 10K and 10L are representative images, with one or more longitudinal markings in each image, taken by the tool of the catheter assembly of FIG. 8B having the tool rotationally aligned with a catheter and a custom-shaped filter applied to each image according to some embodiments.

Referring now to FIG. 10K, a representative image 762 is provided that indicates a modified image 760. The image 760 can be captured by the image sensor 510 of FIGS. 10A and/or 10F, and taken with the optical source 530 turned ON. The image 760 indicates that the tool 520 is rotationally aligned with the catheter 522, since angular positions 610 and 612 are aligned. However, if the angular positions were offset by rotational offset A1, the viewable features 470, 471 in the image 760 can be used to determine the offset. The image 760 can include one or more of the viewable features 470, 471. In this example, the viewable features 470, 471 are offset from each other by an angular offset A2 of 90 degrees. A custom formed filter region 484 is provided to filter out most (if not all) of the viewable objects 472, 473, 474, and 475 from the image 760. The filter region 484 is shown to be slightly larger than the viewable features 470, 471 and the distal end 516. This shape can be determined by the known shape of the combination of the viewable features 470, 471 and the distal end 516. This filter region 484 can be translated up/down and left/right, and rotated, as indicated by arrows 626 (see FIG. 10K), to align with the viewable features 470, 471. The alignment of the filter region 484 with the viewable features 470, 471 can be determined when the HSV of the pixels in the filter region 484 exceed a saturation threshold. Then the angular position of each viewable feature 470, 471 can be determined as described above.

Figure 10L:
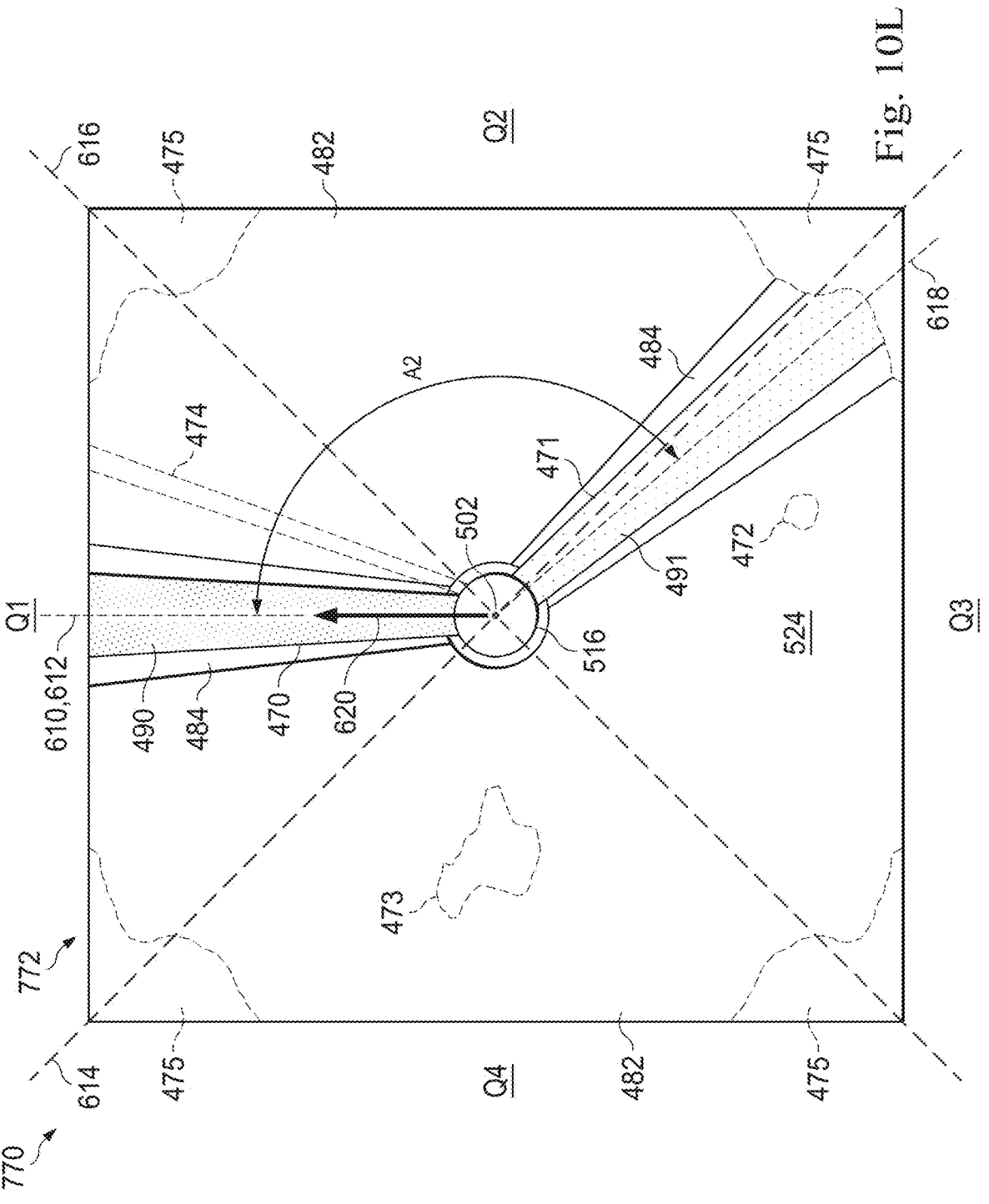
Figure 10M:
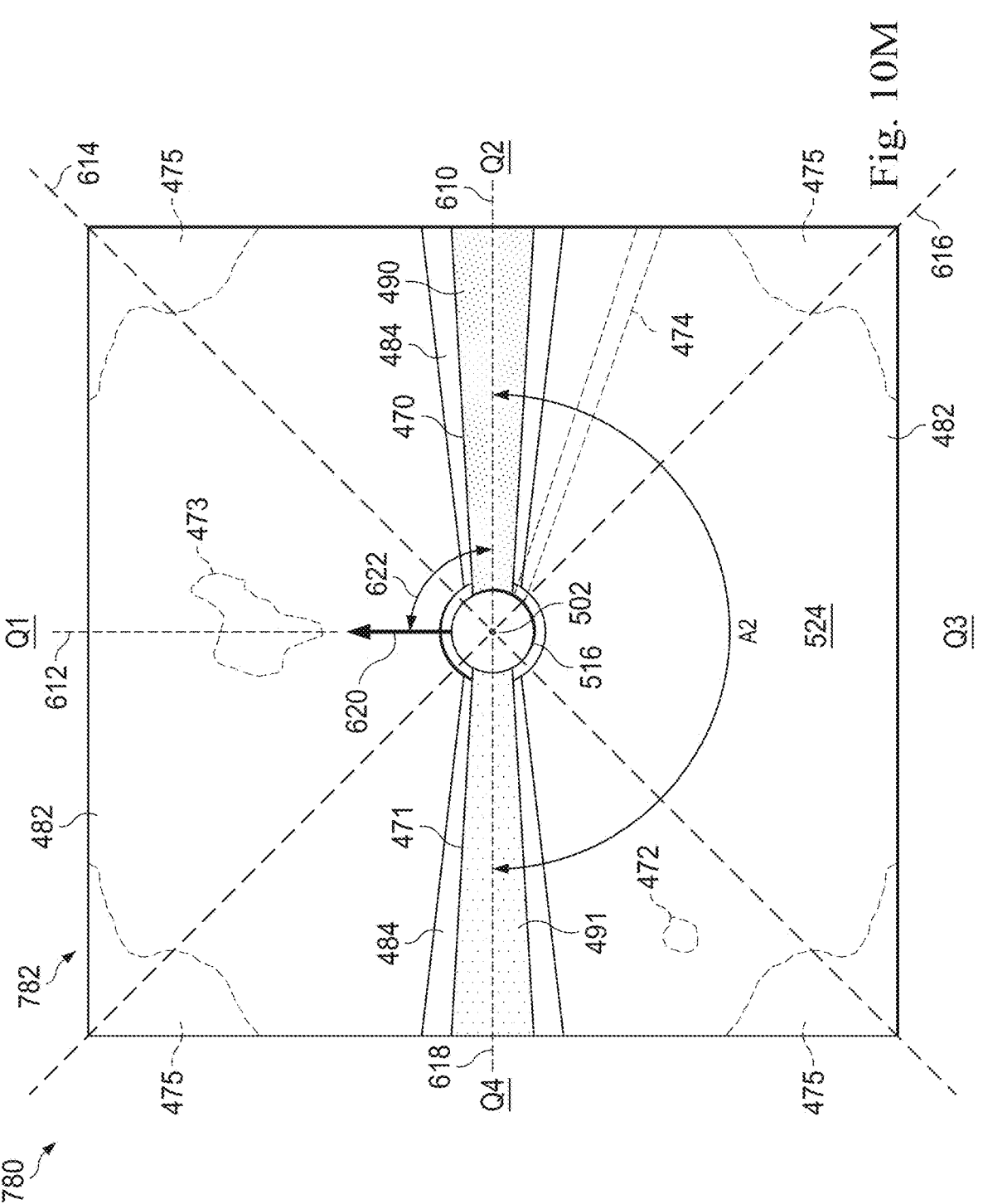
FIG. 10M is a representative image, with one or more longitudinal markings, taken by the tool of the catheter assembly of FIG. 8B having the tool rotationally misaligned with a catheter and a custom-shaped filter applied to the image according to some embodiments.

Referring now to FIG. 10L, a representative image 772 is provided that indicates a modified image 770. The image 770 can be captured by the image sensor 510 of FIGS. 10A and/or 10F, and taken with the optical source 530 turned ON. The image 770 indicates that the tool 520 is rotationally aligned with the catheter 522, since angular positions 610 and 612 are aligned. However, if the angular positions were offset by rotational offset A1, the viewable features 470, 471 in the image 770 can be used to determine the offset. The image 770 can include one or more of the viewable features 470, 471. In this example, the viewable features 470, 471 are offset from each other by an angular offset A2 of greater than 90 degrees but less than 180 degrees. A custom formed filter region 484 is provided to filter out most (if not all) of the viewable objects 472, 473, 474, and 475 from the image 770. The filter region 484 is shown to be slightly larger than the viewable features 470, 471 and the distal end 516. This shape can be determined by the known shape of the combination of the viewable features 470, 471 and the distal end 516. This filter region 484 can be translated up/down and left/right, and rotated, as indicated by arrows 626 (see FIG. 10K), to align with the viewable features 470, 471. The alignment of the filter region 484 with the viewable features 470, 471 can be determined when the HSV of the pixels in the filter region 484 exceed a saturation threshold. Then the angular position of each viewable feature 470, 471 can be determined as described above. FIG. 10M illustrates that the viewable features 470, 471 are not restricted to quadrants of the lumen 524.

Referring now to FIG. 10M, a representative image 782 is provided that indicates a modified image 780. The image 780 can be captured by the image sensor 510 of FIGS. 10A and/or 10F, and taken with the optical source 530 turned ON. The image 780 indicates that the tool 520 is rotationally offset with the catheter 522, since angular positions 610 and 612 are rotationally offset from each other. The image 780 can include one or more of the viewable features 470, 471. In this example, the viewable features 470, 471 are offset from each other by an angular offset A2 of 180 degrees. A custom formed filter region 484 is provided to filter out most (if not all) of the viewable objects 472, 473, 474, and 475 from the image 750. The filter region 484 is shown to be slightly larger than the viewable features 470, 471 and the distal end 516. This shape can be determined by the known shape of the combination of the viewable features 470, 471 and the distal end 516. This filter region 484 can be translated up/down and left/right, and rotated, as indicated by arrows 626 (see FIG. 10K), to align with the viewable features 470, 471. In this example, the tool 520 has been rotated within the catheter 522 by 90 degrees, which can be the case when the lumen 524 and the tool 520 have square cross sections. The alignment of the filter region 484 with the viewable features 470, 471 can be determined when the HSV of the pixels in the filter region 484 exceed a saturation threshold. Then the angular position of each viewable feature 470, 471 can be determined, as well as the rotational offset A1 of the captured image, as described in this disclosure. It should be understood that multiple viewable features can be used in all other embodiments described in this disclosure.

Figure 11:
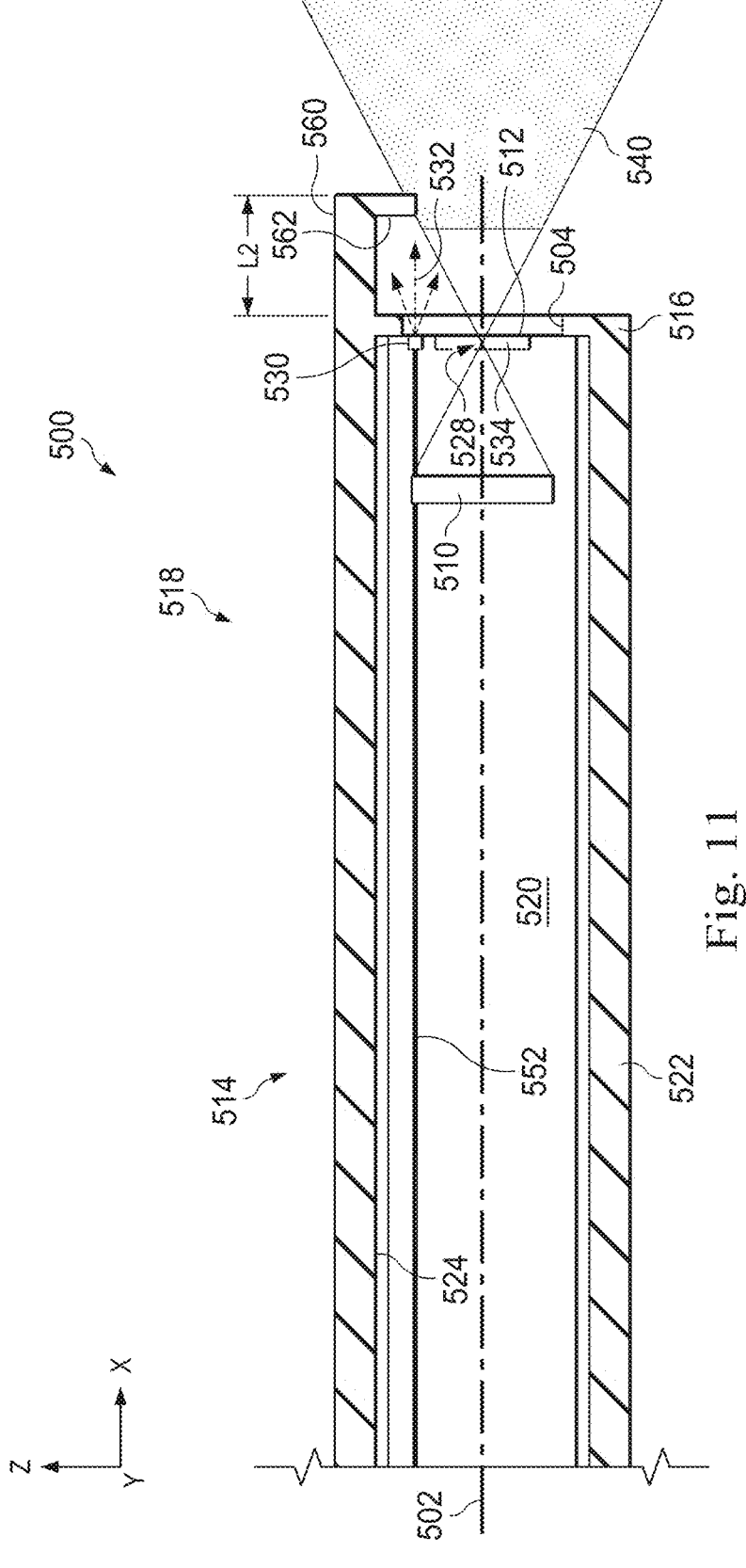
FIG. 11 is a simplified partial cross-sectional view of a distal portion of a catheter assembly with a viewable feature protruding from a distal end of a catheter and a light source at a distal end of a tool within the catheter according to some embodiments.

Referring now to FIG. 11, a simplified partial cross-sectional view of a distal portion 518 of a catheter assembly 500 is shown. A viewable feature 560 protrudes a distance L2 from a distal end 516 of a catheter 522 with a light source 530 at a distal end 512 of a tool 520. An optical waveguide 552 can be used to supply optical energy to the light source 530. The light 532 emitted from the light source 530 can illuminate the viewable feature 560, with at least a portion 562 of the viewable feature 560 being viewed by the image sensor 510. Therefore, an angular position of the viewable feature portion 562 in a captured image can be determined as previously described, and since the angular position of the viewable feature 560 on the catheter 522 is known, then the angular position of the viewable feature 560 in the captured image can be used to determine the rotational offset A1. After the rotational offset A1 is determined, the captured images can be corrected as modified images that are rotationally aligned with the catheter 522.

Figure 12:
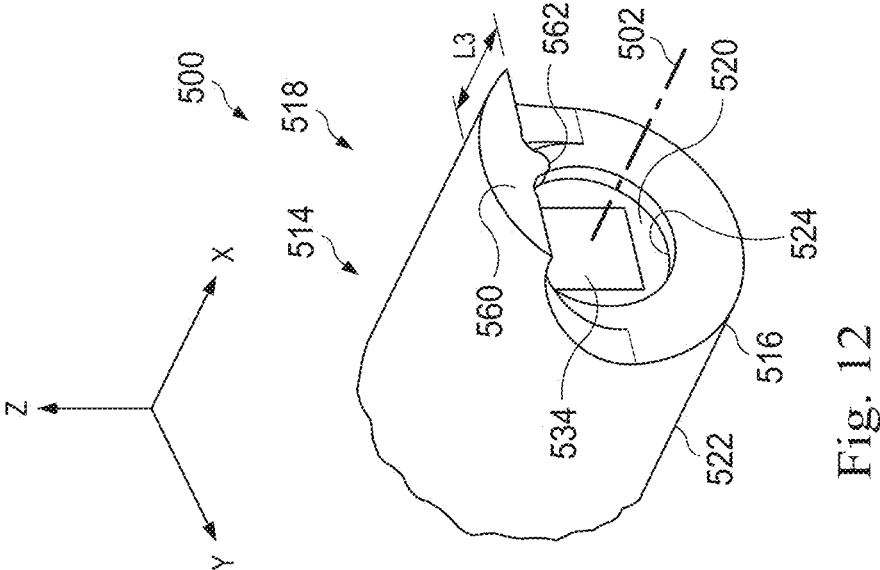
FIG. 12 is a simplified perspective view of a distal portion of a catheter assembly with a viewable feature protruding from a distal end of a catheter according to some embodiments.

Referring now to FIG. 12, a representative perspective view of a catheter assembly 500 is shown. A viewable feature 560 protrudes a distance L3 from a distal end 516 of a catheter 522. At least a portion 562 of the viewable feature 560 can be viewed by the image sensor 510. Therefore, an angular position of the viewable feature portion 562 in a captured image can be determined as previously described, and since the angular position of the viewable feature 560 on the catheter 522 is known, then the angular position of the viewable feature 560 in the captured image can be used to determine the rotational offset A1. After the rotational offset A1 is determined, the captured images can be corrected as modified images that are rotationally aligned with the catheter 522.

Figure 13:
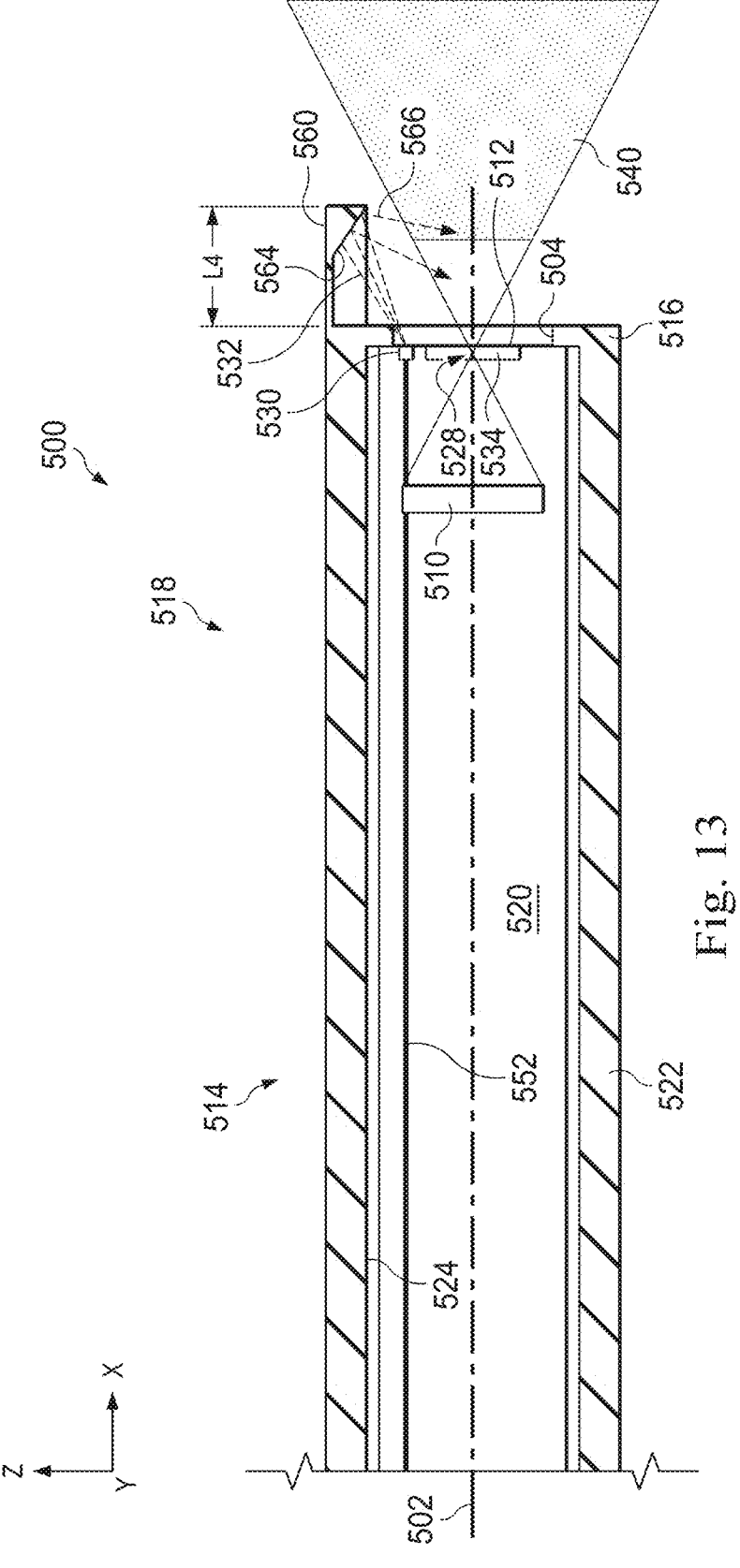
FIG. 13 is a simplified partial cross-sectional view of a distal portion of a catheter assembly with a viewable feature protruding from a distal end of a catheter and a light source at a distal end of the catheter according to some embodiments.

Referring now to FIG. 13, a simplified partial cross-sectional view of a distal portion 518 of a catheter assembly 500 is shown. A viewable feature 560 protrudes a distance L4 from a distal end 516 of a catheter 522 with a light source 530 at the distal end 516. An optical waveguide 552 can be used to supply optical energy to the light source 530. The light 532 emitted from the light source 530 can illuminate the viewable feature 560, with at least a portion of the light 566 being reflected by the reflector 564 (e.g. a mirror) into the viewable region 540, where the reflected light 566 can be captured by the image sensor 510. The reflector 564 can be any surface that reflects both specular and/or diffuse light. Therefore, an angular position of the viewable feature (i.e. the reflected light 566, in this example) in a captured image can be determined, and since the angular position of the viewable feature 560 on the catheter 522 is known, then the angular position of the viewable feature 560 in the captured image can be used to determine the rotational offset A1. After the rotational offset A1 is determined, the captured images can be corrected as modified images that are rotationally aligned with the catheter 522.

Figure 14A:
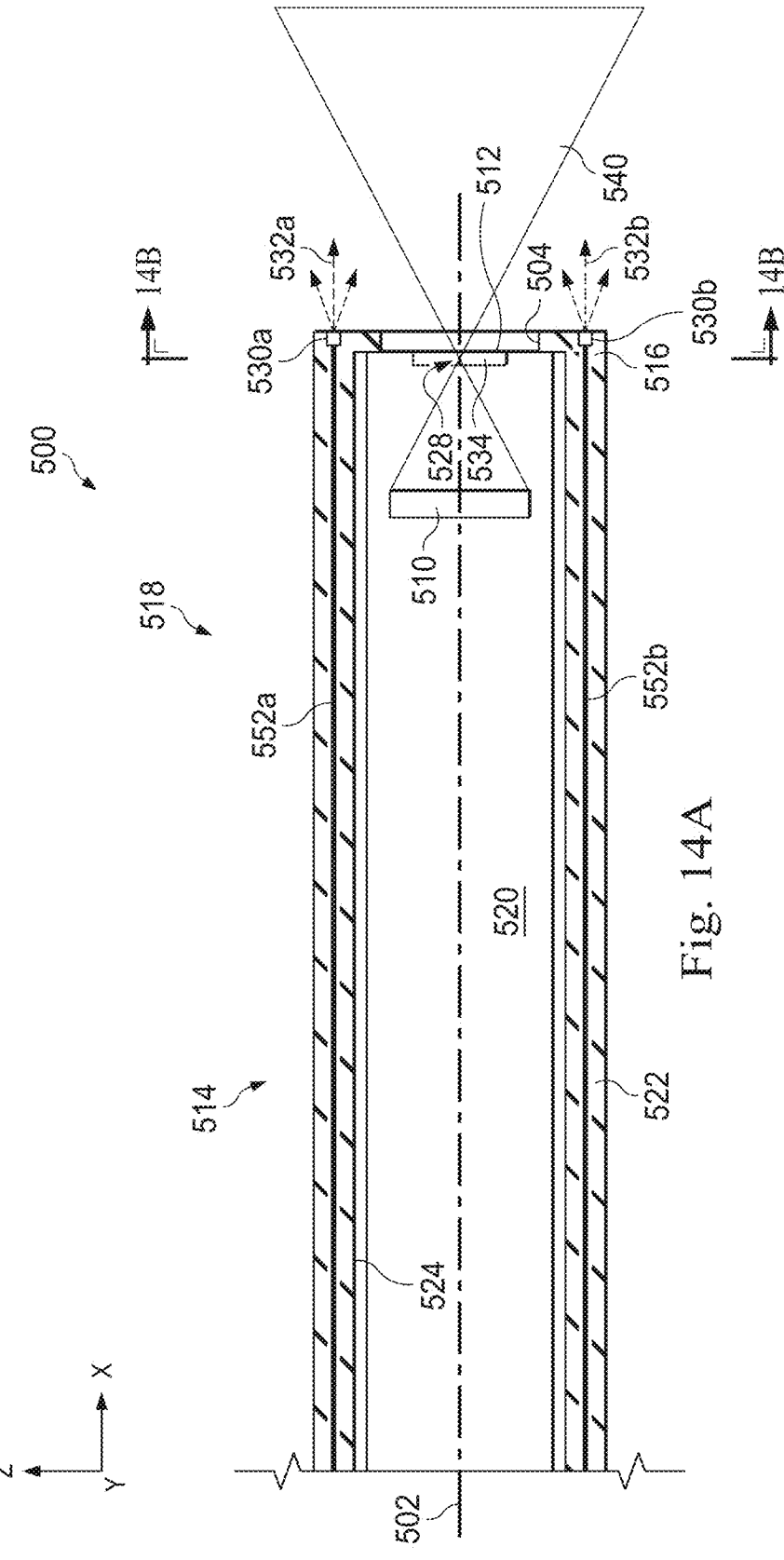
FIG. 14A is a simplified partial cross-sectional view of a distal portion of a catheter assembly with two optical sources oppositely arranged at a distal end of the catheter according to some embodiments.

Referring now to FIG. 14A, a simplified partial cross-sectional view of a distal portion 518 of a catheter assembly 500 is shown. Two optical sources 530a, 530b can be oppositely arranged (i.e. approximately 180 degrees from each other) around the circumference of the catheter 522 at a distal end 516 of the catheter 522. Optical waveguides 552a, 552b can supply optical energy to the optical sources 530a, 530b, respectively. As described below regarding FIGS. 15A-17B, these optical sources 530a, 530b can be used together or separately to determine the rotational offset of the tool 520 relative to the catheter 522.

Figure 14D:
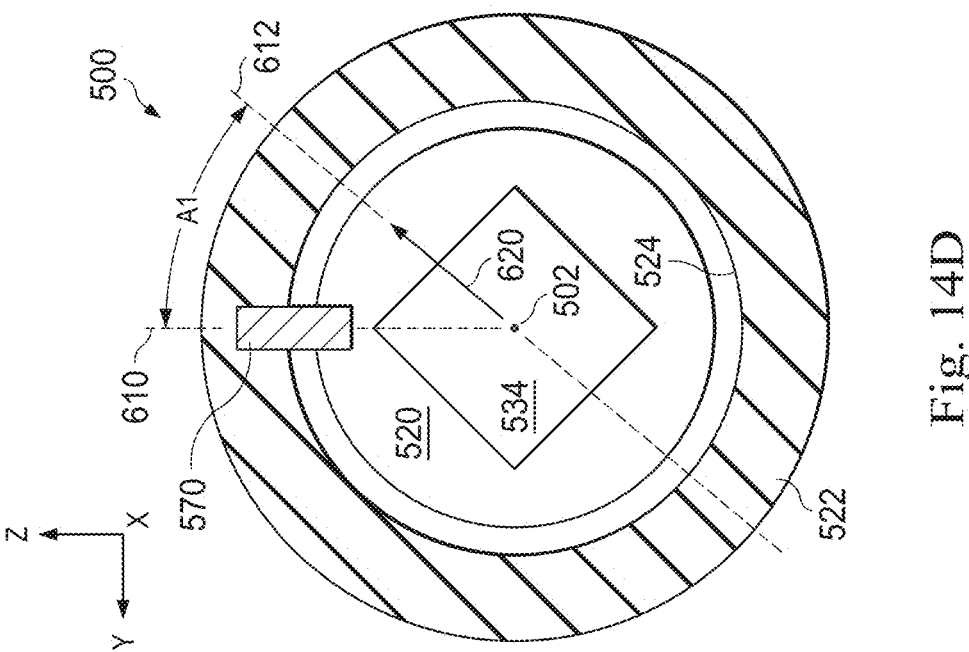
FIG. 14D is a simplified partial cross-sectional end view of a distal portion of a catheter assembly of FIG. 14C with a tool rotationally offset from the catheter according to some embodiments.
Figure 14B:
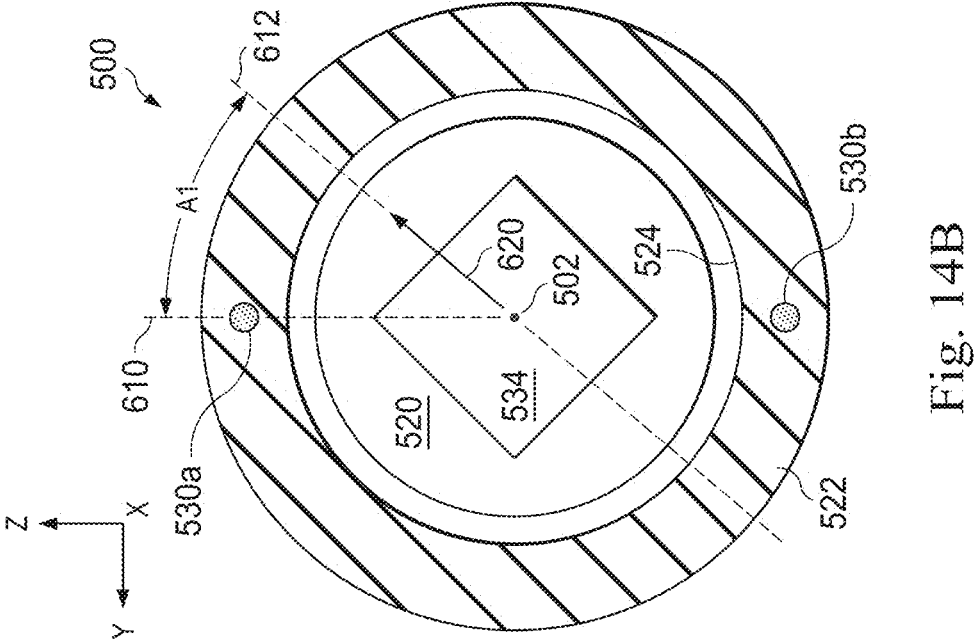
FIG. 14B is a simplified partial cross-sectional end view of a distal portion of a catheter assembly of FIG. 14A with a tool rotationally offset from the catheter according to some embodiments.

Referring now to FIG. 14B, the two optical sources 530a, 530b are oppositely arranged around the distal end 516 of the catheter 522, where the optical source 530a is at the angular position 610 and the optical source 530b is substantially at a 180 degrees angular position around the catheter 522 relative to the optical source 530a. It should be understood that these optical sources 530a, 530b can be arranged at angular positions other than 180 degrees apart. Additional optical sources can also be used to determine the rotational offset A1 between the tool 520 and the catheter 522. The angular position 612 of the tool 520 is shown rotated relative to the angular position 610 by a rotational offset A1. FIGS. 15A-17B are representative images captured by the image sensor 510 of FIG. 14B, which is rotated relative to the catheter 522 by a rotational offset A1. The two optical sources 530a, 530b can be controlled in various ways so as to facilitate determination of the rotational offset A1. The tool 520 can include additional optical sources, for example, to illuminate a region of a patient's anatomy during a procedure. Therefore, the imaging sensor 510 can capture images using the illumination provided by the optical sources on the tool 520, as well as illumination light 532a, 532b provided by the respective optical sources 530a, 530b. The optical sources 530a, 530b are generally used to create a non-uniform distribution of light (which can be seen as a viewable feature) in a viewable region 540, and by processing the images with the non-uniform light distribution using one or more processors in the control system 112, the rotational offset A1 of the tool 520 within the catheter 522 can be determined and future image captures can be corrected to remove the rotational offset.

Figure 14C:
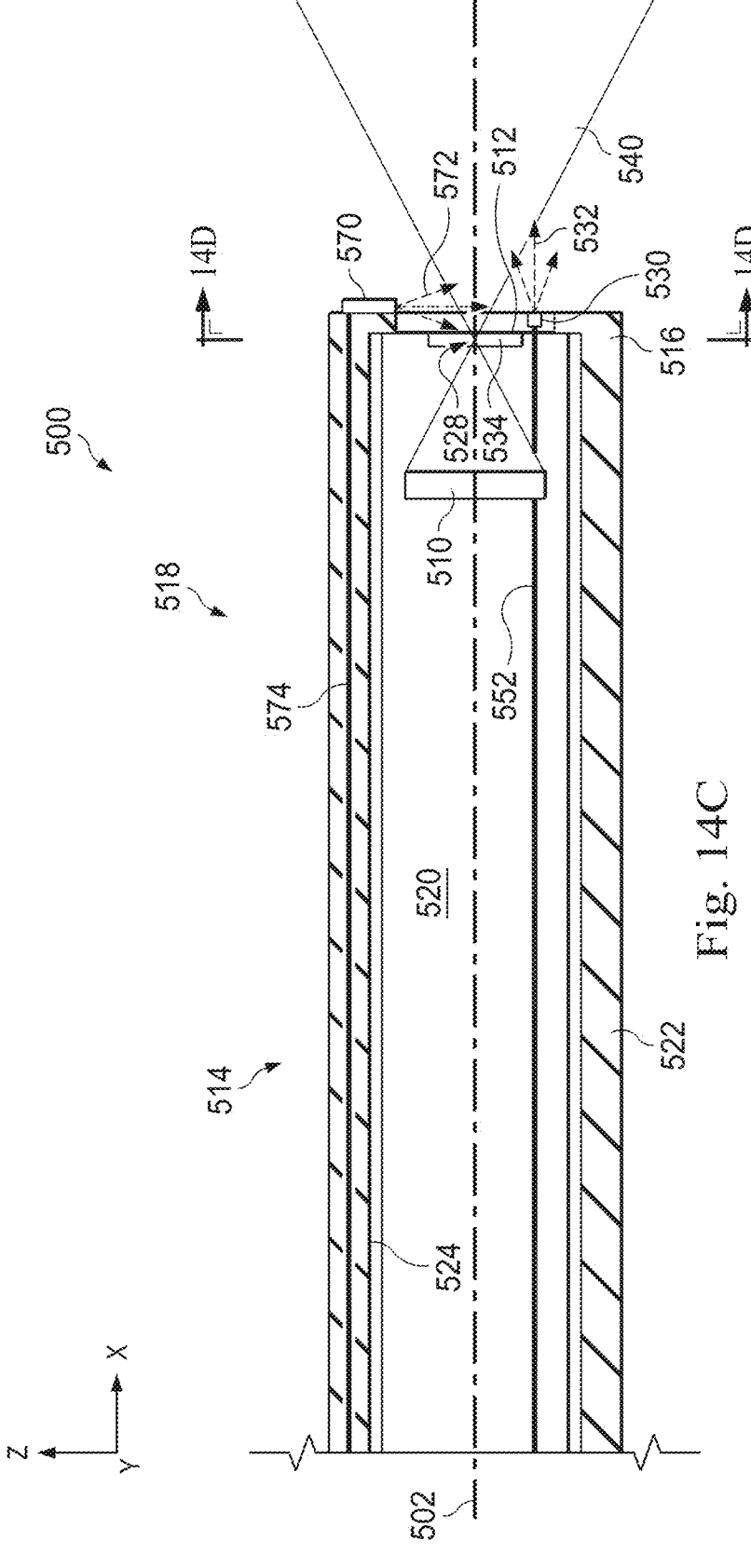
FIG. 14C is a simplified partial cross-sectional view of a distal portion of a catheter assembly with a fluid spray nozzle arranged at a distal end of the catheter according to some embodiments.

Referring now to FIG. 14C, a simplified partial cross-sectional view of a distal portion 518 of a catheter assembly 500 is shown. A fluid spray nozzle 570 can be arranged on the catheter 522 at a distal end 516 of the catheter 522. A fluid flow passage 574 can supply fluid to the fluid spray nozzle 570.

Referring now to FIG. 14D, the fluid spray nozzle 570 is positioned at the angular position 610 on the catheter 522. The angular position 612 of the tool 520 is shown rotated relative to the angular position 610 by a rotational offset A1. Images captured by the image sensor 510 of FIG. 14D, can be rotated relative to the catheter 522 by a rotational offset A1. The fluid spray nozzle 570 can be controlled to facilitate determination of the rotational offset A1 by spraying fluid 572 in front of the imaging sensor 510 at the angular position 610. The tool 520 can include additional fluid sources, if desired. The imaging sensor 510 can capture images using the illumination light 532 provided by an optical source 530 on the tool 520 and/or illumination from other optical sources mounted to the catheter 522. The fluid nozzle can create a fluid spray pattern (which can be seen as a viewable feature) in a viewable region 540, and by processing the images, in which the fluid spray pattern appears, using one or more processors in the control system 112, the rotational offset of the tool 520 within the catheter 522 can be determined and future image captures can be corrected to remove the rotational offset.

Figure 15C:
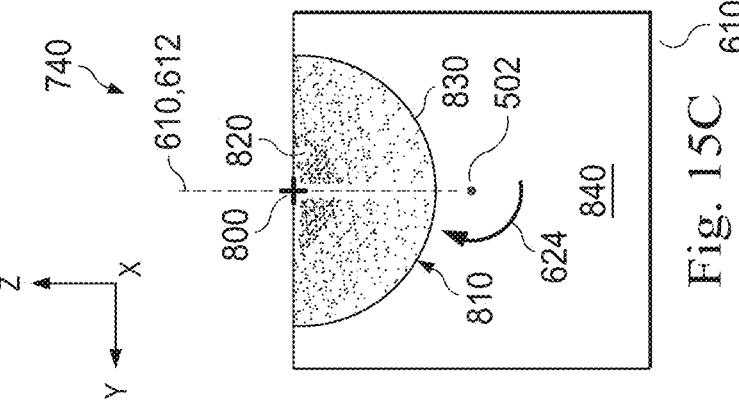
FIG. 15C is a representative image of the image of FIG. 15B with the rotational offset removed according to some embodiments.
Figure 15B:
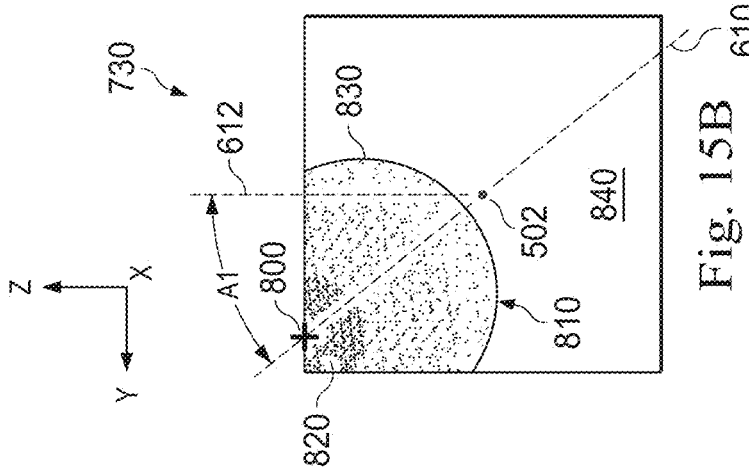
FIGS. 15A-15B are representative images taken as viewed from the distal end of the tool in FIG. 14B using one light source according to some embodiments.
Figure 15A:
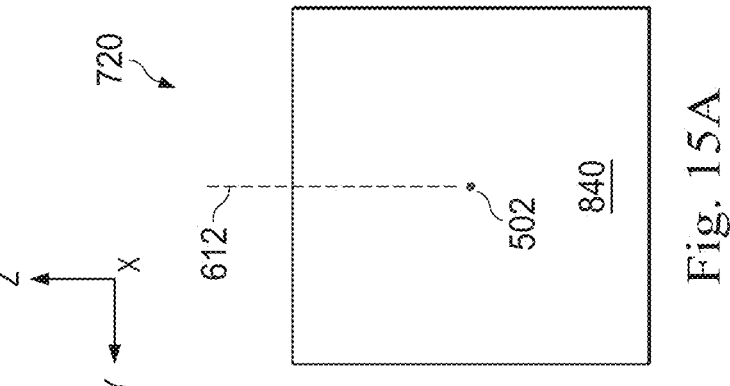

Referring now to FIG. 15A, a representative image 720 is captured by the image sensor 510 of FIG. 14B, and taken without turning on either of the optical sources 530a, 530b. Image 720 can be used as a baseline image to compare to another captured image (e.g. image 730 of FIG. 15B) to determine differences between an image with one or more of the optical sources 530a, 530b turned on and this baseline image that has both optical sources 530a, 530b turned off.

Referring now to FIG. 15B, a representative image 730 can be captured by the image sensor 510 of FIG. 14B, at a rotational offset A1, and taken with the optical source 530a turned on and the optical source 530b turned off. A non-uniform light distribution 810 can result when the optical source 530a is turned on. The non-uniform light distribution 810 can have a boundary 830 between the non-uniform light and the light distribution in image 720 that was not changed by turning on the optical source 530a. The light distribution 810 can display a gradient of light distribution from the boundary 830 to a high intensity area 820. The light distribution 810 can be a varying intensity of light, a color gradient, a pattern of light, etc. The control system 112 can compare the images 720, 730 and adjust to 0 (zero, i.e. red=blue=green=0) a subset of the pixels from an area of the image 730 that was not changed when the optical source 530a was turned on. With the unchanged subset of pixels set to zero, the modified image 730 may show only the subset of pixels associated with the light distribution 810. The visible subset of pixels can be processed to determine the centroid 800 of the light distribution 810, thereby identifying the angular position of the optical source 530a on the catheter, since the highest concentration of light distribution 810 can be at the light source, and thereby can identify the angular position 610 in the modified image 730 of the optical source 530a on the catheter 522. By comparing the angular position 610 in the modified image 730 of the optical source 530a with the expected angular position 612 of the imaging sensor 510, the rotational offset A1 can be determined.

Referring now to FIG. 15C, a representative image 740 is shown and represents the image 730 modified to remove the rotational offset A1. The control system 112 can rotate 624 the image 730 to compensate for the rotational offset A1, and create a modified image 740 that is rotationally aligned with the tool 520 and can be displayed to a user. Future images captured by the imaging sensor 510 at this rotational offset A1 can be automatically adjusted before being displayed to a user. The rotational offset A1 can also be used to adjust manipulations of the control cables for articulating the distal portion 518 of the catheter.

Figures 16A, 16B, 16C:
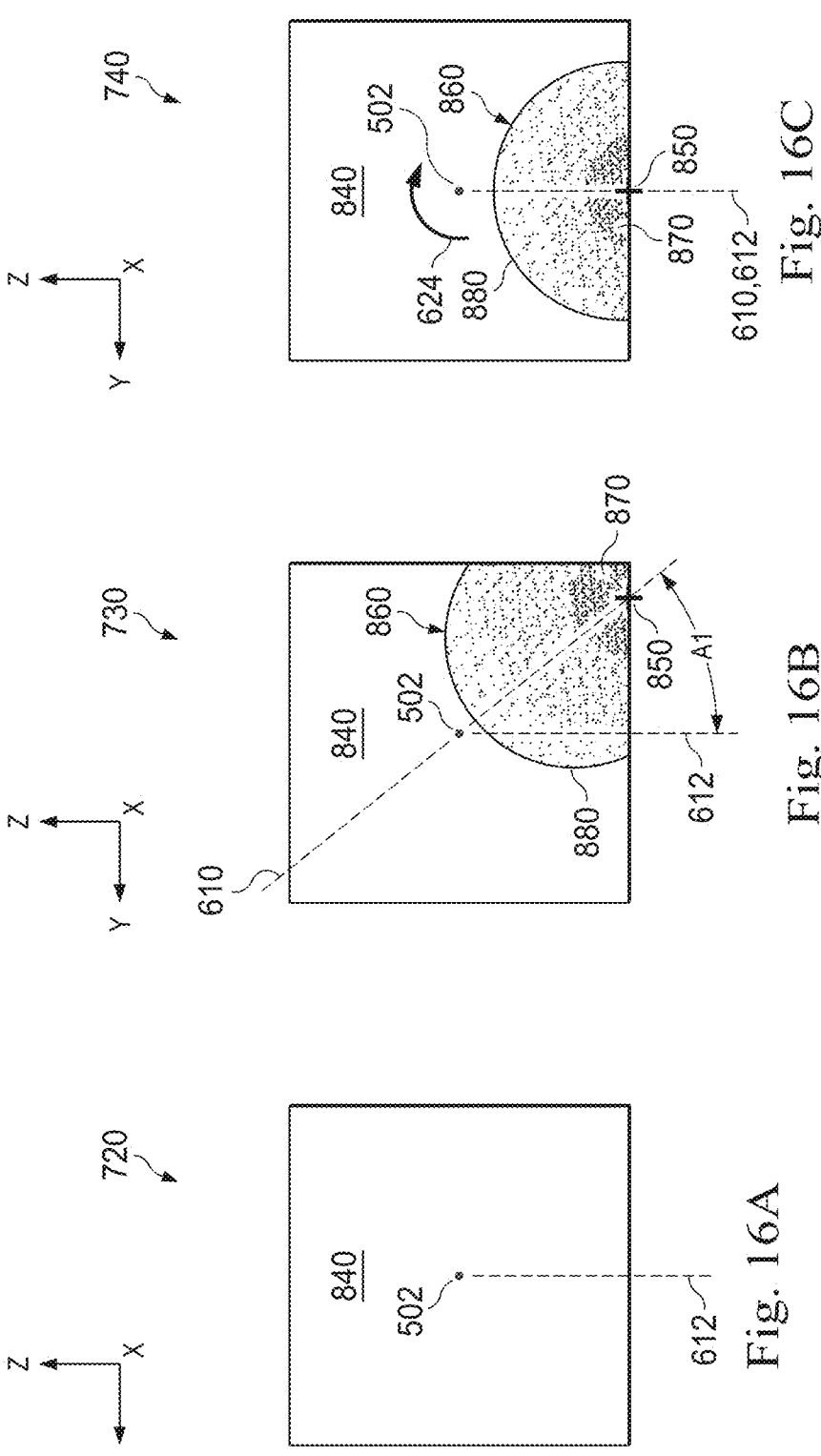
FIGS. 16A-16B are representative images taken as viewed from the distal end of the tool in FIG. 14B using another light source according to some embodiments.
FIG. 16C is a representative image of the image of FIG. 16B with the rotational offset removed according to some embodiments.

Referring now to FIG. 16A, a representative image 720 is captured by the image sensor 510 of FIG. 14B, and taken without turning on either of the optical sources 530a, 530b. Image 720 can be used as a baseline image to compare to another captured image (e.g. image 730 of FIG. 16B) to determine differences between an image with one or more of the optical sources 530a, 530b turned on and this baseline image that has both optical sources 530a, 530b turned off.

Referring now to FIG. 16B, a representative image 730 can be captured by the image sensor 510 of FIG. 14B, at a rotational offset A1, and taken with the optical source 530b turned on and the optical source 530a turned off. A non-uniform light distribution 860 can result when the optical source 530b is turned on. The non-uniform light distribution 860 can have a boundary 880 between the non-uniform light and the light distribution of image 720 that was not changed when the optical source 530b was turned on. The light distribution 860 can display a gradient of light distribution from the boundary 880 to a high intensity area 870. The light distribution 860 can be a varying intensity of light, a color gradient, a pattern of light, etc. The control system 112 can compare the images 720, 730 and adjust a subset of the pixels to zero that was not changed when the optical source 530b was turned on. With the subset of pixels set to zero, the modified image 730 may show only the subset of pixels associated with the light distribution 860. The visible subset of pixels can be processed to determine the centroid 850 of the light distribution 860, thereby identifying the angular position 610 in the modified image 730 of the optical source 530b (and thus the catheter 522) relative to the angular position 612 (i.e. top middle of the image) of the imaging sensor 510, since the highest concentration of light distribution 860 can be at the light source, and thereby can identify the angular position 610 in the modified image 730 of the optical source 530b. By comparing the angular position 610 of the optical source 530b with the angular position 612 of the imaging sensor 510, the rotational offset A1 can be determined.

Referring now to FIG. 16C, a representative image 740 is shown and represents the image 730 modified to remove the rotational offset A1. The control system 112 can rotate 624 the image 730 to compensate for the rotational offset A1 and create a modified image 740 that is rotationally aligned with the tool 520 and can be displayed to a user. Future images captured by the imaging sensor 510 at this rotational offset A1 can be automatically adjusted to remove the rotational offset A1 before being displayed to a user. The rotational offset A1 can also be used to adjust manipulations of the control cables for articulating the distal portion 518 of the catheter.

Figures 17A, 17B, 17C:
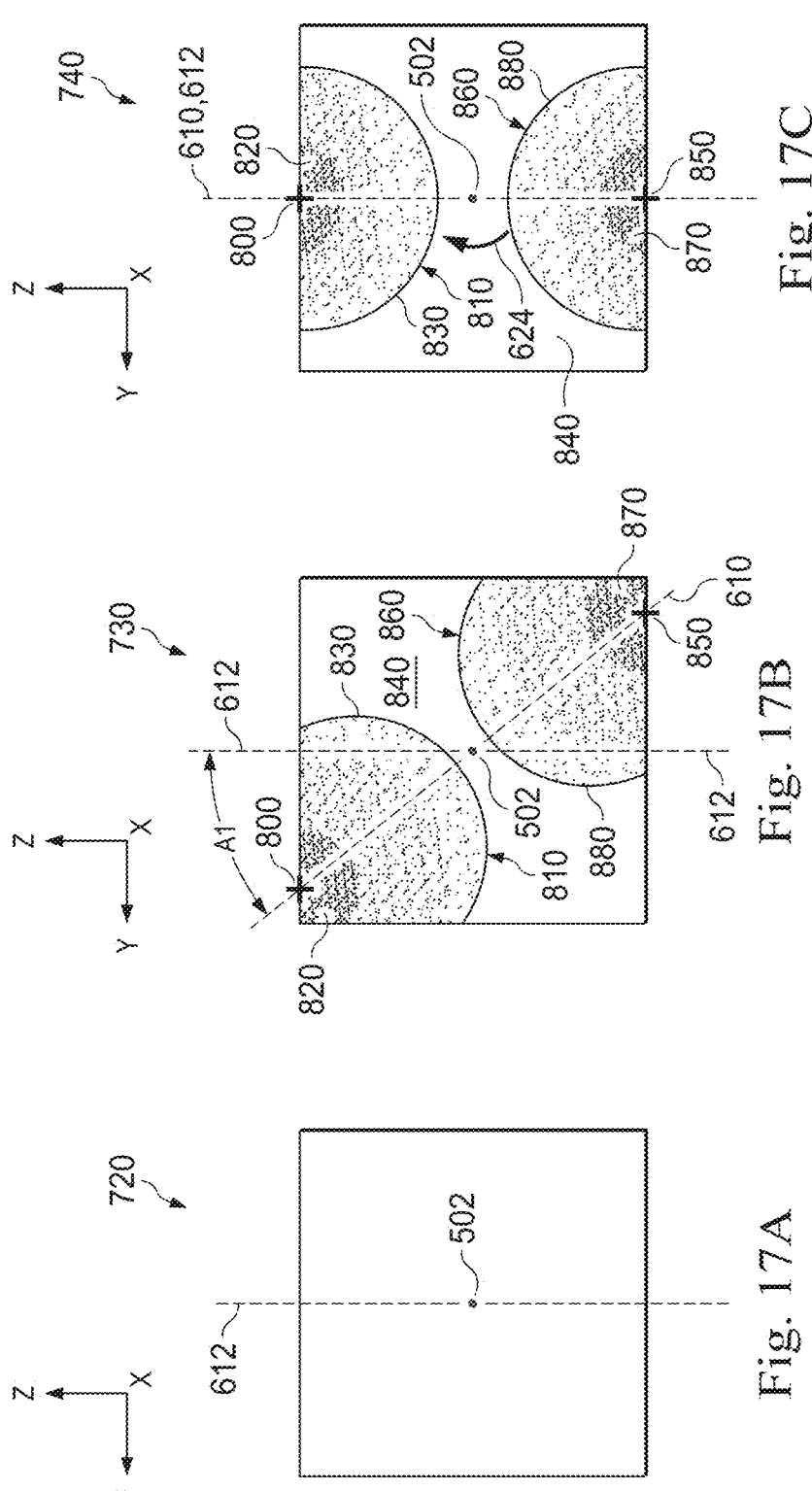
FIGS. 17A-17B are a representative image taken as viewed from the distal end of the tool in FIG. 14B using both light sources according to some embodiments.
FIG. 17C is a representative image of the image of FIG. 17B with the rotational offset removed according to some embodiments.

Referring now to FIG. 17A, a representative image 720 is captured by the image sensor 510 of FIG. 14B and taken without turning on either of the optical sources 530a, 530b. Image 720 can be used as a baseline image to compare to another captured image (e.g. image 730 of FIG. 17B) to determine differences between an image with one or more of the optical sources 530a, 530b turned on and this baseline image that has both optical sources 530a, 530b turned off.

Referring now to FIG. 17B, a representative image 730 can be captured by the image sensor 510 of FIG. 14B, at a rotational offset A1, and taken with the optical sources 530a, 530b turned on. Non-uniform light distributions 810, 860 can result when the optical sources 530a, 530b are turned on. The non-uniform light distributions 810, 860 can have respective boundaries 830, 880 between the non-uniform light distributions 810, 860 and the light distribution of image 720 that was not changed when the optical sources 530a, 530b were turned on. The light distributions 810, 860 can display a gradient of light distribution from the respective boundaries 830, 880 to respective high intensity areas 820, 870. The light distributions 810, 860 can be a varying intensity of light, a color gradient, a pattern of light, etc. The control system 112 can compare the images 720, 730 and adjust a subset of the pixels from an area of the image 730 that were not changed when the optical sources 530a, 530b were turned on. With the unchanged subset of pixels set to zero, the modified image 730 may show only the subset of pixels associated with the light distributions 810, 860. The remaining subset of pixels can be processed to determine the centroids 800, 850 of the respective light distributions 810, 860, thereby identifying the angular position 610 in the image 730 of the optical sources 530a, 530b on the catheter, since the highest concentration of light distributions 810, 860 can be at the respective light sources, and thereby can identify the angular position 610 of the optical sources 530a, 530b on the catheter 522. By comparing the angular position 610 of the optical sources 530a, 530b with the angular position 612 of the imaging sensor 510, the rotational offset A1 can be determined.

Referring now to FIG. 17C, a representative image 740 is shown and represents the image 730 modified to remove the rotational offset A1. The control system 112 can rotate 624 the image 730 to compensate for the rotational offset A1 and create a modified image 740 that that is rotationally aligned with the tool 520 and can be displayed to the user. Future images captured by the imaging sensor 510 at this rotational offset A1 can be automatically adjusted to remove the rotational offset A1. The rotational offset A1 can also be used to adjust manipulations of the control cables for articulating the distal portion 518 of the catheter.

Figure 18B:
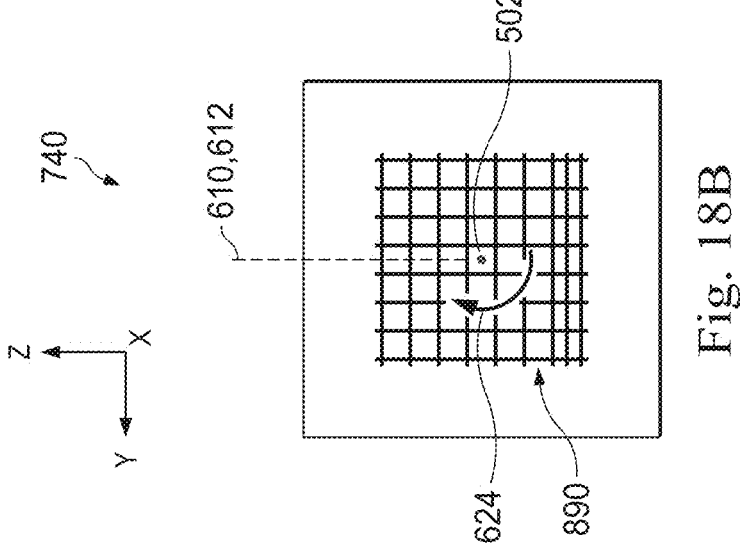
FIG. 18B is a representative image of the image of FIG. 18A with the rotational offset removed according to some embodiments.
Figure 18A:
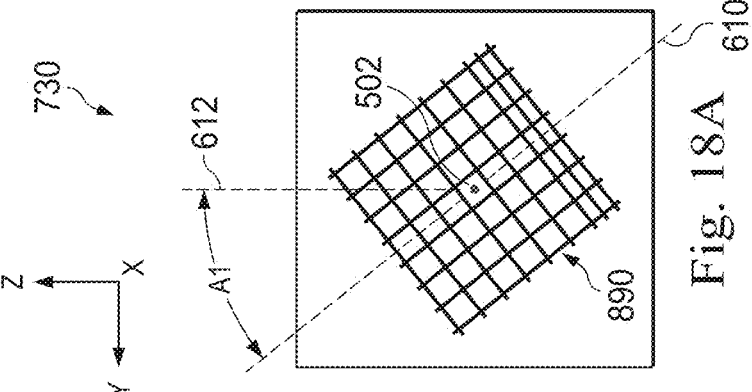
FIG. 18A is a representative image taken as viewed from the distal end of the tool in FIG. 14B using a light source with a structured light pattern according to some embodiments.

Referring now to FIG. 18A, a representative image 730 can be captured by the image sensor 510 of FIG. 14B, at a rotational offset A1, and taken with one or more of the optical sources 530a, 530b turned on. For this example, at least the optical source 530a is turned on and illuminates an object or objects in the viewable region 540 of the imaging sensor 510. The optical source 530a can be a waveguide with manufactured features at its distal portion that project a pattern of light onto the object(s) in the viewable region 540. The pattern 890 can be any pattern of light that can be detected by the imaging sensor 510 and used to determine a rotational offset of the imaging sensor 510. Therefore, the pattern 890 can be a grid pattern as shown, or a unique arrangement of illumination dots (e.g. similar to a star constellation). The dots can be a uniform size, with a unique arrangement, or the dots can be a uniform shape or pattern with the light illuminating the object(s) with a non-uniform color, or combinations thereof. The non-uniform color can be a varied color temperature, a color gradient, a color pattern, or combinations thereof. The optical source 530a (or 530b) can produce light 532a (or 532b) to illuminate the objects with a high frequency light (e.g. IR light) that is not in the human visible spectrum, but can be detected and captured by the imaging sensor 510. With lower frequency light, the optical sources 530a, 530b may be periodically turned on and off to limit the time the user sees the illumination from the optical sources 530a, 530b in the captured images. With the high frequency light, the optical sources 530a, 530b may remain on during the procedure to maintain the offset correction integrity, since the user is not able to see the high frequency light.

One or more of the optical sources 530a, 530b can project a structured light onto object(s) in the viewable region 540. In this example, the structured light 890 is a unique grid pattern. The imaging sensor 510 of the FIG. 14B is at a rotational offset A1 within the catheter 522. The imaging sensor 510 can capture the image 730 shown in FIG. 18A. The control system 112 may process the image 730 to adjust to zero a subset of pixels not associated with the structured light 890, and then process the visible subset of pixels to determine the angular orientation of the structured light 890 in the image 730. The angular orientation of the structured light 890 can be used to determine the angular position 610 of the catheter 522 relative to the tool 520, and thereby determine the orientation of the tool 520 within the catheter 522. The control system 112 can determine the rotational offset A1 by comparing the angular position 610 of the catheter 522 in the image 730 with the angular position 612 of the imaging sensor 510.

Referring now to FIG. 18B, a representative image 740 is shown and represents the image 730 modified to remove the rotational offset A1. The control system 112 can rotate the image 730 (e.g. as shown by arrow 624) to compensate for the rotational offset A1 and create a modified image 740 that can be displayed to the user. Future images captured by the imaging sensor 510 at this rotational offset A1 can be automatically adjusted to remove the rotational offset A1 before being displayed on a user display. The rotational offset A1 can also be used to adjust manipulations of the control cables for articulating the distal portion 518 of the catheter.

Therefore, the viewable feature can include the longitudinal marking 470, the protruding viewable feature 560, the non-uniform light distributions 810, 860, and the structured light pattern 890. The rotational offset A1 can be continually and/or periodically updated and the correction of rotated images can be updated with the new offset A1, throughout the procedure, if desired.

Figure 19A:
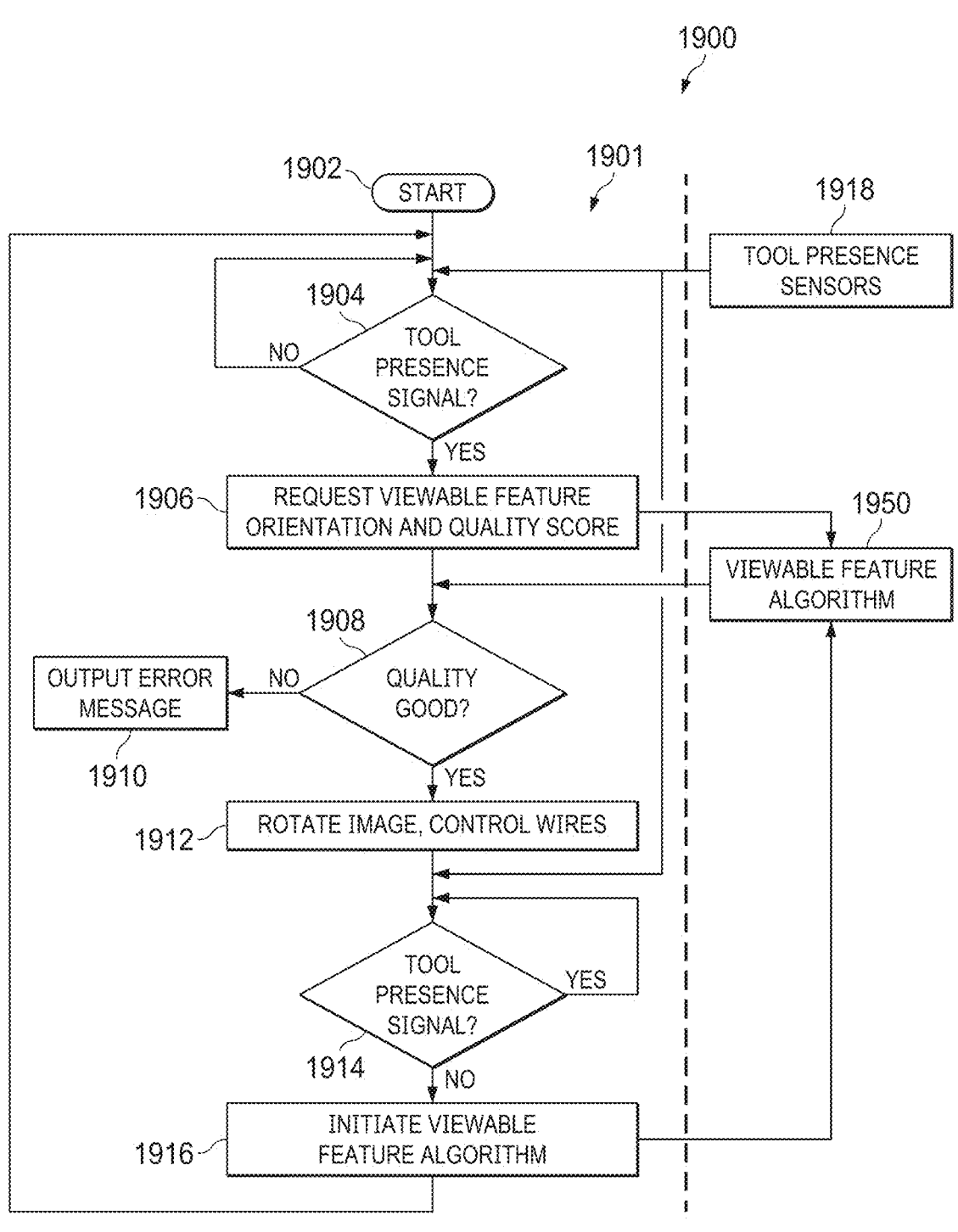
FIG. 19A is a representative flow chart for controlling collection and adjustments of images during a procedure according to some embodiments.
Figure 19B:
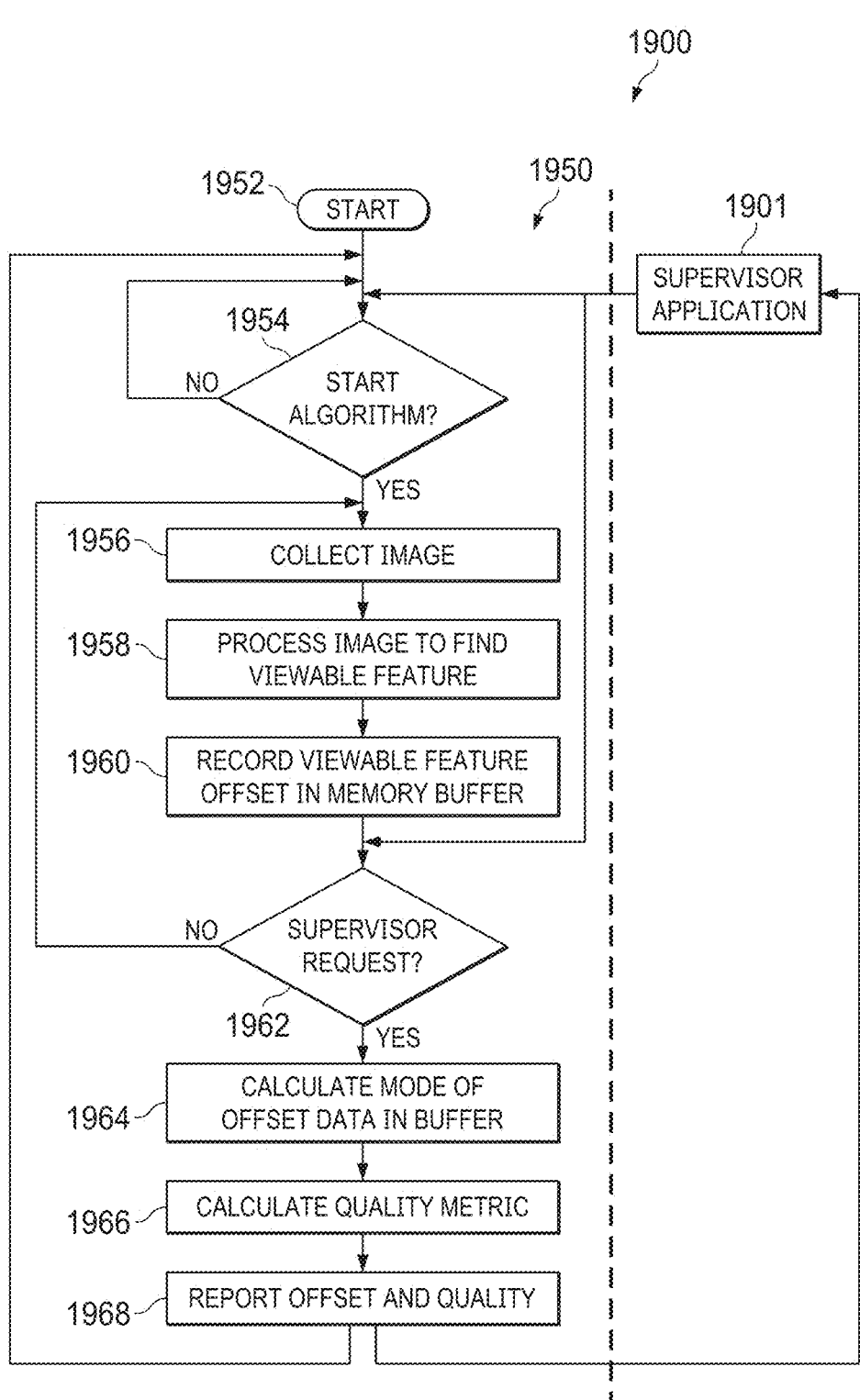
FIG. 19B is a representative flow chart for controlling when a rotational offsets of images are collected during a procedure and reported to the control system according to some embodiments.
Figure 19C:
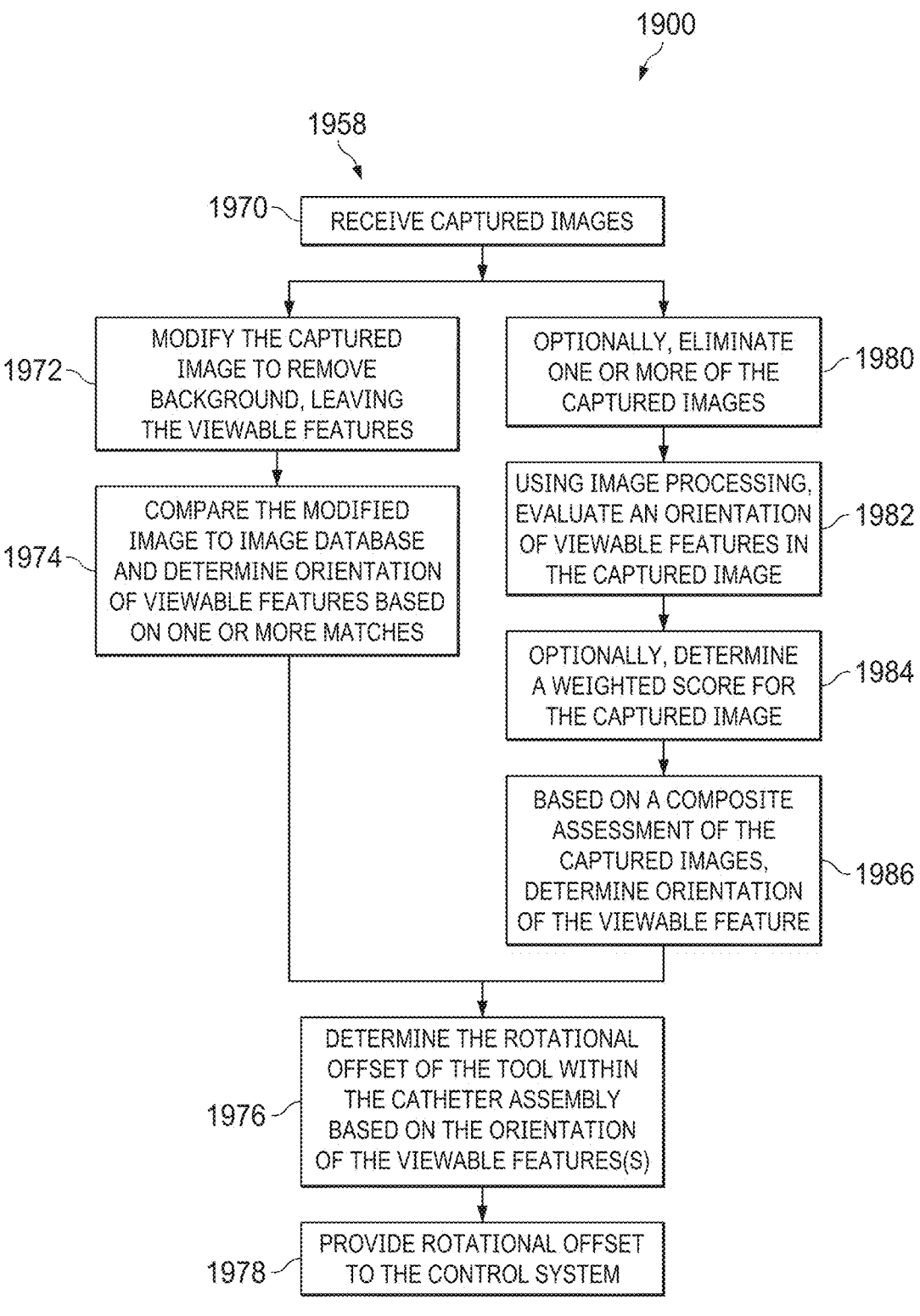
FIG. 19C is a representative flow chart for detecting a viewable feature in a captured image and determining a rotational offset of the viewable feature according to some embodiments.

The method 1900 is illustrated in FIGS. 19A-19C as a set of operations or processes 1902 through 1978. Not all of the illustrated processes 1902 through 1978 may be performed in all embodiments of method 1900. Additionally, one or more processes that are not expressly illustrated in FIGS. 19A-19C may be included before, after, in between, or as part of the processes 1902 through 1978. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

Referring now to FIGS. 19A-19C, representative flow charts for the method 1900 of controlling the collection of images during a procedure, determining a rotational offset of an imaging sensor, and correcting captured images by removing the rotational offset prior to displaying the captured images to a user. Each of the illustrated methods comprise a set of operations or processes. Not all of the illustrated processes may be performed in all embodiments of the methods. Additionally, one or more processes that are not expressly illustrated may be included before, after, in between, or as part of the illustrated processes. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

FIG. 19A is a representative flow chart of a supervisor process 1901 that can control the collection and correction of images during a procedure. The process 1901 can initiate and control a process 1950 (see FIG. 19B) to determine a rotational offset of the tool 520 in a catheter 522 and receive the rotational offset and quality metrics of collected and calculated data. The process 1950 can initiate a process 1958

(see FIG. 19C) to analyze a captured image to determine the rotational offset. The following paragraphs describe these processes in more detail.

The supervisor process 1901 starts at operation 1902. In some implementations, an indication of the start of the process can be received from the user at 1902. Once the process 1901 is started at operation 1902, an operation 1904 determines whether a tool 520 is present in the catheter 522. A presence indicator can be provided by operation 1918, which monitors presence sensors to determine whether the tool 520 is partially or fully inserted into the catheter 522 based on insertion signatures detected by one or more target readers (or sensors) or not inserted at all. When it is determined that the tool 520 is partially inserted, the supervisor process 1901 can detect a longitudinal marking within the lumen 524 of the catheter 522 to determine a rotational offset A1 of the tool 520 in the catheter 522. However, when it is determined that the tool 520 is fully inserted in the catheter 522, the longitudinal marking within the lumen 524 may not be viewable. Therefore, when the tool 520 is fully inserted in the catheter 522, the control system 112 may disable image collection that would be used for purposes of determining the rotational offset A1 if only longitudinal marking(s) 470, 471 are being used.

The supervisor process 1901 can also detect viewable features (e.g. 560, 810, 860, and 890) other than the longitudinal marking that can be used to determine the rotational offset A1 of the tool 520 in the catheter 522. When the other viewable features (e.g. 560, 810, 860, and 890) are being used, then the image capture may be disabled during insertion of the tool 520 and enabled when the tool 520 is fully inserted. If the longitudinal marking(s) 470, 471 and one or more of the other viewable features (e.g. 560, 810, 860, and 890) are being used, then an image collection rate can be slower before the tool 520 enters the catheter 522, and then increase the image collection rate when the tool 520 is partially or fully inserted. The control system 112 may enable image collection after the tool 520 enters the catheter 522 for capturing images with one or more of the longitudinal marking(s) 470, 471 in the images. After the tool 520 is fully inserted, the control system 112 may continue image collection to capture images with one or more of the viewable features 560, 810, 860, and 890 in the images (or stop image collection, if none of the other viewable features 560, 810, 860, and 890 are used). When it is determined that the tool 520 is not inserted into the catheter 522, then the supervisor process 1901 can hold in operation 1904 waiting on a positive indication that the tool is at least partially inserted into the catheter.

When the positive indication is received, the supervisor process 1901 can proceed to operation 1906, which can request an orientation (or angular position) of a viewable feature 470, 471, 560, 810, 860, 890 captured in an image, and a quality scoring of the collected and calculated information (such as the angular position of the viewable feature). The process 1950 collects images and determines the rotational offset A1 of a viewable feature 470, 471, 560, 810, 860, 890 in the image(s), as well as a quality metric that can provide a weighting as to the confidence in the information provided back to the supervisor process 1901. If the supervisor process 1901 determines that the quality of the information from the operation 1950 is below a threshold level, then operation 1910 can output an error message to the control system 112, which can alert the user and/or log the error message for later review.

If the quality of the information from the operation 1950 is above a threshold level, then operation 1912 can use the information to rotate operational images to remove the rotational offset A1 (such as illustrated by the images in FIGS. 9A, 9B) and/or adjust the manipulations of the control cables 630, 632, 634, 636. Operation 1912 can continue while operation 1914 continues to monitor the tool presence signal supplied by the operation 1918. If the tool presence signal remains active, indicating no change, then the operation 1912 can continue. If the tool presence signal is no longer active (i.e. if the tool 520 has been moved from fully inserted, or removed all together from the catheter 522), then the process 1901 may proceed to operation 1916 that can request initiation of the viewable feature process 1950, again. This may be desirable if the tool 520 remains partially inserted in the catheter 522, and the viewable feature process 1950 can again determine an orientation of the tool 520 in the catheter by detecting the viewable feature, which in this case, can be a longitudinal marking(s) 470, 471. The process 1901 can also proceed from operation 1916 to operation 1902 to restart the process and proceed to operation 1904 to again wait on a positive tool presence indicator before continuing with operations in the process 1901.

Referring to FIG. 19B, the process 1950 can start at operation 1952 and proceed to operation 1954 which can wait on an indication from the supervisor process 1901. When the rotational offset of the tool 520 within a catheter 522 is desired, the supervisor process 1901 can send a positive signal to the process 1950 to proceed to the next operation. In operation 1956, an image (or images) can be captured by the imaging sensor, where the captured image(s) can include the viewable feature(s) 470, 471, 560, 810, 860, 890.

In operation 1958, the image(s) are processed to identify the viewable feature(s) 470, 471, 560, 810, 860, 890 and its rotational offset A1 relative to an expected position in the image (e.g. angular position 612 that is the top middle position in the image).

In operation 1960, the information determined in operation 1958 can be stored in a memory buffer for later analysis and calculations. Operation 1962 checks to see if the supervisor process 1901 has requested data. If a data request is not indicated, the process 1950 continues to repeat processes 1956, 1958, 1960 and 1962 until a data request is indicated. Since process 1950 can be started while the tool 520 is being installed in the catheter 522, the memory buffer can store multiple images captured within the catheter 522 and/or the calculated rotational offset(s) A1. In one embodiment, the memory buffer can continue to store the last 50 images, pushing out the oldest image and inputting the newest image.

A data request may occur when a positive tool presence signal is received by the supervisor process 1901, which can mean that multiple images have already been stored in the memory buffer, since the images were being collected during the installation of the tool 520. If a data request is indicated, then the process 1950 may proceed to operation 1964, which can analyze the data in the memory buffer, calculate a rotational offset for each image, and calculate a statistical mode across the multiple images that best describe the rotational position of the tool 520 within the catheter 522. Operation 1966 can calculate a quality metric to indicate the confidence of the calculated rotational offset of the tool 520. The quality metric can include a determination for each processed image as to the confidence that the image contained the viewable feature (e.g. the longitudinal marking) and the confidence of the angular position of the viewable feature in the image. Operation 1968 reports the rotational offset and quality metric to the supervisor process

1901 and returns the process 1950 back to operation 1954 to again wait for a start algorithm indication from the supervisor process 1901.

In general, the supervisor process 1901 may start the algorithm when the tool presence indication is negative, but not request data. When the tool presence indication is positive, the start algorithm indication can be negated, with the data request indication being positive, causing the calculated data to be transmitted to the supervisor process 1901. The supervisor process 1901 can be directed at the system that detects a rotational offset for a tool 520 in a catheter as the tool is being inserted in the catheter 522. However, the process 1901 can also support the embodiments where the tool 520 is fully installed (i.e. inserted) in the catheter 522 and images captured by the imaging sensor 510 include a viewable feature 560, 810, 860, 890. The start algorithm indications and data request indications can be supplied to the process 1950 at times other than those mentioned above and can cause multiple images to be collected when the tool 520 is fully installed, and data requests to be indicated at various times during the procedure, as long as the tool 520 remains fully installed in the catheter 522, in some embodiments. The process 1950 can provide analysis of a number (e.g. 20, 30, 40, 50, 60, 70, 80, 100, etc.) of the last captured images when a data request (e.g. requesting orientation of the tool) is received, such as when the tool 520 is fully inserted. Additionally, the process 1950 can continuously analyze a number of images (e.g. 20, 30, 40, 50, 60, 70, 80, 100, etc.) as they are captured and stored in the buffer. Then when a data request (e.g. requesting orientation of the tool) is received, then the process can immediately respond with the requested data for the number of images without requiring further analysis. Alternatively, or in addition to, the process 1950 can provide analysis of a number (e.g. 20, 30, 40, 50, 60, 70, 80, 100, etc.) of the captured images after the tool 520 is fully inserted into the catheter 522. For viewable features 560, 810, 860, and 890, these features may not be visible when the tool 520 is not fully inserted. Therefore, the process 1950 may wait for an indication that the tool is fully inserted before sending a data request, causing data to be supplied to the control system 112 for images captured after the tool 520 is fully inserted, whether the analysis of the number of images was performed before or after receiving the data request.

Referring now to FIG. 19C, operation 1958 can include multiple operations as shown. Operation 1970 can receive the captured images, where the captured images may include a viewable feature 470, 471, 560, 810, 860, 890. The captured images may be processes through one or more operations to determine the orientation of the viewable feature. The processes may include removing subsets of pixels associated with background or obstructive objects (e.g., processes 1972, 1974) and/or evaluating a set of multiple images (e.g., processes 1980-1986).

Operation 1972 can modify the captured images to remove the background and leave the subset of pixels associated with the viewable feature in the image. Removing the background can be done by comparing a baseline image to a captured image with a viewable feature 470, 471, 560, 810, 860, 890. The differences between the two images should be largely due to the viewable feature 470, 471, 560, 810, 860, 890. Therefore, removing the subset of pixels that are basically the same between the two images, will leave the viewable feature still viewable in the modified image. It should be understood, that removing the subset of pixels may not necessarily mean that the pixels are deleted from the image, but merely changed to a value that renders the pixels in the subset to be Red=Blue=Green which is "0 (zero)."

Another way to remove (or set to zero) the pixels associated with a background can be to perform a "white balance correction" by identifying a background color and setting the background pixels to a neutral color and leave the contrast of the viewable feature(s) 470, 471, 560, 810, 860, 890. The viewable feature(s) 470, 471, 560, 810, 860, 890 can then be extracted into another image without the background. Once the viewable feature(s) 470, 471, 560, 810, 860, 890 has been isolated in operation 1972, operation 1974 can compare the modified image containing the viewable feature(s) 470, 471, 560, 810, 860, 890 (or a centroid of the viewable features), to a plurality of model images and an angular position of the viewable feature can be determined based on one or more matches to the model images.

The processes 1980-1986 may use multiple images, captured over a period of time, to determine the orientation of a viewable feature. At a process 1980, one or more of the captured images may, optionally, be eliminated from further analysis. The elimination of the captured images may be based on a temporal value associated with the captured image, such as when the images were captured compared to when the tool was fully seated in the catheter. For example, as the tool 520 is seated at the distal end of the catheter 522, the captured image may become more obstructed as mucus and other anatomical debris fill the image. In some embodiments if the last six seconds of captured images (e.g., at approximately 20 captured images per second) prior to tool seating constitute the set of received captured images, the last two seconds of captured images may be eliminated from further analysis due to a likelihood that they will be heavily obstructed.

At a process 1982, image processing techniques may be used to evaluate a likely orientation of viewable features (e.g., 470, 471, 560, 810, 860, 890) in the captured images. For each captured image in the set of captured images (or in the remaining subset if images have been eliminated at process 1980), a pixel analysis may be performed. Based on the pixel analysis, each captured image may be assigned a likely orientation value associated with a determined orientation of the viewable feature or may be assigned an indeterminate value associated with a determination that the pixel analysis cannot establish, with sufficient likelihood, an orientation of the viewable feature. For example, if the viewable feature is a longitudinal stripe 470, the pixel analysis may determine which pixels are associated with the color, size or other characteristic of the stripe 470 and may determine the quadrant (Q1-Q4) of the tool in which the pixels associated with stripe 470 are located. Thus, each captured image may be associated with a likely quadrant in which the stripe 470 is located. If the pixel analysis of a captured image cannot identify pixels associated with the stripe 470 or finds pixels associated with the stripe 470 in multiple quadrants (e.g., due to color distortions), an indeterminate value may be assigned.

At a process 1984, the likely determined orientation of the viewable feature may be weighted with a confidence score based on criteria including, for example, the number of pixels in the captured image associated with the likely determined orientation, the number of pixels in the captured image associated with a different orientation from the likely determined orientation, the time order of the captured image (e.g., images captured six seconds prior to full seating may be more valuable than images captured two seconds prior to full seating). In one example, a captured image with 8,000 pixels associated with the likely determined orientation may receive a higher confidence score than a captured image with 4,000 pixels associated with the likely determined orientation.

At a process 1986, a composite assessment of the likely determined orientations of the viewable feature in the multiple captured images may be performed to determine a final orientation of the viewable feature. In some embodiments, the composite assessment may include developing an average of the likely orientation values to determine a final composite orientation of the viewable feature. In some embodiments, the composite assessment may include developing a combination of the likely orientation values, such as a weighted average (i.e., weighted by the confidence score) of the likely orientation values, to determine a final composite orientation of the viewable feature.

At a process 1976 the rotational offset A1 of the tool within the catheter maybe determined based on the determined final orientation (e.g., angular position) of the viewable feature 470, 471, 560, 810, 860, 890. Operation 1978 can provide the rotational offset to the process 1958.

One or more elements in the embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Various aspects of the subject matter described herein are set forth in the following numbered examples:

Example 1: A system comprising a tool, a catheter sized to receive the tool, an image sensor carried by the tool, a processor and a memory having computer readable instructions stored thereon, the computer readable instructions, when executed by the processor, cause the system to capture with the image sensor, a first image within a lumen of the catheter, the first image comprising a plurality of pixels; identify a first subset of the plurality of pixels comprising a viewable feature and a second subset of the plurality of pixels comprising a background color; adjust the second subset of the plurality of pixels to a neutral color; create a modified image by filtering the plurality of pixels to remove the second subset; determine an angular orientation of the viewable feature in the modified image; and determine a rotational offset of the tool relative to the catheter based on the angular orientation of the viewable feature.

Example 2: The system of Example 1, wherein a distal portion of the tool has a square cross-section and the lumen has a complimentary square cross-section, and wherein the rotational offset is 0 (zero), 90, 180, or 270 degrees.

Example 3: The system of Example 1, wherein the tool has a circular cross-section and the lumen has a complimentary circular cross-section, and wherein the rotational offset is within a range of 0 to 360 degrees.

Example 4: The system of Example 1, wherein the computer readable instructions, when executed by the processor, further cause the system to capture operational images during a procedure; rotate the operational images by the rotational offset; and display the rotated operational images on a display unit.

Example 5: The system of Example 4, wherein the computer readable instructions, when executed by the processor, further cause the system to repeat the capturing the first image, the identifying, the adjusting, the determining the angular orientation, and the determining the rotational offset periodically during the procedure.

Example 6: The system of Example 1, wherein the computer readable instructions, when executed by the processor, further cause the system to initiate control movement of a distal portion of the catheter based on the rotational offset.

Example 7: The system of Example 1, wherein the computer readable instructions, when executed by the processor, further cause the system to capture the first image that includes the viewable feature indicative of a longitudinal marking that extends longitudinally along an interior wall of the catheter.

Example 8: The system of Example 1, wherein the computer readable instructions, when executed by the processor, further cause the system to identify the viewable feature including a structure that protrudes from a distal portion of the catheter.

Example 9: The system of Example 1, wherein the computer readable instructions, when executed by the processor, further cause the system to identify the viewable feature including a fluid spray pattern of a fluid that is sprayed from a distal portion of the catheter.

Example 10: The system of Example 1, wherein the computer readable instructions, when executed by the processor, further cause the system to identify the viewable feature including a light source that emits light from a distal portion of the catheter.

Example 11: The system of Example 1, further comprising a structured light source that emits a structured light from a distal portion of the catheter.

Example 12: The system of Example 11, wherein the structured light is a colored illumination light.

Example 13: The system of Example 11, wherein the viewable feature is illuminated by the structured light and wherein the determining the angular orientation of the viewable feature further comprises comparing the first image to a plurality of model images, and determining the angular orientation is based on one or more matches with the model images.

Example 14: The system of Example 1, wherein the computer readable instructions, when executed by the processor, further cause the system to illuminate a distal portion of the catheter with at least one of two optical light sources arranged around the distal portion of the catheter; and wherein identifying the viewable feature includes identifying an object illuminated by the at least one of the optical light sources.

Example 15: The system of Example 14, wherein the computer readable instructions, when executed by the processor, further cause the system to illuminate the object with the two optical light sources; capture the first image that includes the object illuminated by the two optical light sources; illuminate the object with a first one of the two optical light sources while keeping a second one of the two optical light sources off; capture a second image that includes the object illuminated by the first one of the two optical light sources; illuminate the object with the second one of the two optical light sources while keeping the first one of the two optical light sources off; and capture a third image that includes the object illuminated by the second one of the two optical light sources.

Example 16: The system of Example 15, wherein the computer readable instructions, when executed by the processor, further cause the system to compare the first image to the second image; compare the first image to the third image; and determine the rotational offset of the tool relative to the catheter based on the comparing the first and second images, comparing the first and third images, or a combination thereof.

Example 17: The system of Example 14, wherein the computer readable instructions, when executed by the processor, further cause the system to illuminate the object with the two optical light sources, having different correlated color temperatures respectively; capture the first image that includes the object illuminated by the two optical light sources; analyze a non-uniform shading of the object in the first image; and determine the rotational offset of the tool relative to the catheter based on the analyzing the non-uniform shading of the object in the first image.

Example 18: The system of Example 1, wherein the first image is an image of an anatomy of a patient and a second image is created by one or more CT scans of the anatomy of the patient and is the image of the anatomy at a 0 (zero) degree angular orientation, wherein the determining the angular orientation further comprises comparing the first image to the second image and determining the angular orientation of the first image based on the comparing.

Example 19: The system of Example 1, wherein the computer readable instructions, when executed by the processor, further cause the system to rotate and scale the first image to create a third image that matches a second image, thereby determining the rotational offset needed to rotate the first image to match the second image.

Example 20: A method for determining an orientation of a tool installed at least partially within a catheter, the method comprising: capturing, via an image sensor of the tool, a first image within a lumen of the catheter, the first image comprising a plurality of pixels; identifying a first subset of the plurality of pixels comprising a viewable feature and a second subset of the plurality of pixels comprising a background color; adjusting the second subset of the plurality of pixels to a neutral color; creating a modified image by filtering the plurality of pixels to remove the second subset; determining an angular orientation of the viewable feature in the modified image; and determining a rotational offset of the tool relative to the catheter based on the angular orientation of the viewable feature.

Example 21: The method of Example 20, further comprising: capturing operational images during a procedure; automatically rotating the operational images by the rotational offset; and displaying the rotated operational images on a display unit.

Example 22: The method of Example 21, repeating the capturing the first image, the identifying, the adjusting, determining the angular orientation and the determining the rotational offset periodically during the procedure.

Example 23: The method of Example 20, further comprising initiating control movement of a distal portion of the catheter based on the rotational offset.

Example 24: The method of Example 20, further comprising capturing the first image that includes the viewable feature indicative of a longitudinal marking that extends longitudinally along an interior wall of the catheter.

Example 25: The method of Example 20, wherein identifying the viewable feature includes identifying a structure that protrudes from a distal portion of the catheter.

Example 26: The method of Example 20, wherein identifying the viewable feature includes identifying a fluid spray pattern of a fluid that is sprayed from a distal portion of the catheter.

Example 27: The method of Example 20, wherein identifying the viewable feature includes identifying a light source that emits light from a distal portion of the catheter.

Example 28: The method of Example 20, wherein identifying the viewable feature includes identifying an object illuminated by a structured light source that emits a structured light from a distal portion of the catheter.

Example 29: The method of Example 28, further comprising: capturing the first image that includes the object illuminated by the structured light, wherein the determining the angular orientation of the viewable feature further comprises comparing the first image to a plurality of model images, and determining the angular orientation based on one or more matches with the model images.

Example 30: The method of Example 20, further comprising illuminating a distal portion of the catheter with at least one of two optical light sources arranged around the distal portion of the catheter; and wherein identifying the viewable feature includes identifying an object illuminated by the at least one of the optical light sources.

Example 31: The method of Example 30, further comprising: illuminating the object with the two optical light sources; capturing the first image that includes the object illuminated by the two optical light sources; illuminating the object with a first one of the two optical light sources while keeping a second one of the two optical light sources off; capturing a second image that includes the object illuminated by the first one of the two optical light sources; illuminating the object with the second one of the two optical light sources while keeping the first one of the two optical light sources off; and capturing a third image that includes the object illuminated by the second one of the two optical light sources.

Example 32: The method of Example 31, further comprising: comparing the first image to the second image; comparing the first image to the third image; and determining the rotational offset of the tool relative to the catheter based on the comparing the first and second images, comparing the first and third images, or a combination thereof.

Example 33: The method of Example 30, further comprising: illuminating the object with the two optical light sources, having different correlated color temperatures respectively; capturing the first image that includes the object illuminated by the two optical light sources; analyzing a non-uniform shading of the object in the first image; and determining the rotational offset of the tool relative to the catheter based on the analyzing the non-uniform shading of the object in the first image.

Example 34: The method of Example 20, wherein the first image is an image of an anatomy of a patient and a second image is created by one or more CT scans of the anatomy of the patient and is the image of the anatomy at a 0 (zero) degree angular orientation, wherein the determining the angular orientation further comprises comparing the first image to the second image and determining the angular orientation of the first image based on the comparing.

Example 35: The method of Example 20, further comprising: rotating and scaling the first image to create a third image that matches a second image, thereby determining the rotational offset needed to rotate the first image to match the second image.

Example 36: A system comprising: a catheter including a lumen; a tool shaped to be positioned in the lumen; an imaging sensor positioned in the tool; and a viewable feature on the catheter within a field of view of the imaging sensor, wherein the imaging sensor is configured to capture a plurality of images of the field of view, the plurality of images including a first image that includes the viewable feature, and wherein a position of the viewable feature in the first image indicates a rotational offset of the tool relative to the catheter.

Example 37: The system of Example 36, further comprising: a processor configured to collect the plurality of images from the imaging sensor during a procedure, rotationally adjust at least one of the plurality of images to remove the rotational offset, and transmit the adjusted at least one of the plurality of images to a display.

Example 38: The system of Example 37, wherein the processor is further configured to adjust manipulations of control cables in the catheter based on the rotational offset.

Example 39: The system of Example 36, wherein a distal portion of the tool has a square cross-section and the lumen has a complimentary square cross-section, and wherein the rotational offset is 0 (zero), 90, 180, or 270 degrees.

Example 40: The system of Example 36, wherein the tool has a circular cross-section and the lumen has a complimentary circular cross-section, and wherein the rotational offset is within a range of 0 (zero) to 360 degrees.

Example 41: The system of Example 36, wherein the viewable feature includes a longitudinal marking that longitudinally extends along an interior wall of the catheter.

Example 42: The system of Example 36, wherein the viewable feature includes a structure that protrudes from a distal portion of the catheter.

Example 43: The system of Example 36, wherein the viewable feature includes a fluid spray pattern of a fluid that is sprayed from a distal portion of the catheter.

Example 44: The system of Example 36, wherein the viewable feature includes a light source that emits light from a distal portion of the catheter.

Example 45: The system of Example 36, further comprising a structured light source configured to emit a structured light from a distal portion of the catheter to illuminate the viewable feature.

Example 46: The system of Example 36, further comprising a structured light source including first and second optical sources oppositely arranged around a distal portion of the catheter, wherein the first optical source is configured to emit a first structured light at a different time than the second optical source emits a second structured light, wherein the first image is captured when the first optical source emits the first structured light and a second image is captured when the second optical source emits the second structured light, and wherein the rotational offset is determined by differences between the first and second images.

Example 47: A non-transitory machine-readable medium comprising a plurality of machine-readable instructions which when executed by one or more processors associated with a computer-assisted medical system device are adapted to cause the one or more processors to perform a method comprising: receiving, via an image sensor carried by a tool, a first image from within a lumen of the catheter, the first image comprising a plurality of pixels; identifying a first subset of the plurality of pixels comprising a viewable feature and a second subset of the plurality of pixels comprising a background color; adjusting the second subset of the plurality of pixels to a neutral color; generating a modified image by filtering the plurality of pixels to remove the second subset; determining an angular orientation of the viewable feature in the modified image; and determining a rotational offset of the tool relative to the catheter based on the angular orientation of the viewable feature.

Example 48: The non-transitory machine-readable medium of Example 47 wherein the plurality of machine-readable instructions, when executed by the one or more processors are adapted to cause the one or more processors to perform a method further comprising: capturing operational images during a procedure; rotate the operational images by the rotational offset; and display the rotated operational images on a display unit.

Example 49: The non-transitory machine-readable medium of Example 47 wherein the plurality of machine-readable instructions, when executed by the one or more processors are adapted to cause the one or more processors to perform a method further comprising: repeating the capturing the first image, the identifying, the adjusting, the determining the angular orientation, and the determining the rotational offset periodically during the procedure.

Example 50: The non-transitory machine-readable medium of Example 47 wherein the plurality of machine-readable instructions, when executed by the one or more processors are adapted to cause the one or more processors to perform a method further comprising: initiating control movement of a distal portion of the catheter based on the rotational offset.

Example 51: The non-transitory machine-readable medium of Example 47 wherein the plurality of machine-readable instructions, when executed by the one or more processors are adapted to cause the one or more processors to perform a method further comprising: capturing the first image that includes the viewable feature indicative of a longitudinal marking that extends longitudinally along an interior wall of the catheter.

Example 52: The non-transitory machine-readable medium of Example 47 wherein the plurality of machine-readable instructions, when executed by the one or more processors are adapted to cause the one or more processors to perform a method further comprising: identifying the viewable feature including a structure that protrudes from a distal portion of the catheter.

Example 53: The non-transitory machine-readable medium of Example 47 wherein the plurality of machine-readable instructions, when executed by the one or more processors are adapted to cause the one or more processors to perform a method further comprising: identifying the viewable feature including a fluid spray pattern of a fluid that is sprayed from a distal portion of the catheter.

Example 53: The non-transitory machine-readable medium of Example 47 wherein the plurality of machine-readable instructions, when executed by the one or more processors are adapted to cause the one or more processors to perform a method further comprising: identifying the viewable feature including a light source that emits light from a distal portion of the catheter.

Example 54: The non-transitory machine-readable medium of Example 47 wherein the plurality of machine-readable instructions, when executed by the one or more processors are adapted to cause the one or more processors to perform a method further comprising: illuminating a distal portion of the catheter with at least one of two optical light sources arranged around the distal portion of the catheter; and wherein identifying the viewable feature includes identifying an object illuminated by the at least one of the optical light sources.

Example 55: The non-transitory machine-readable medium of Example 54 wherein the plurality of machine-readable instructions, when executed by the one or more processors are adapted to cause the one or more processors to perform a method further comprising: illuminating the object with the two optical light sources; capturing the first image that includes the object illuminated by the two optical light sources; illuminating the object with a first one of the two optical light sources while keeping a second one of the two optical light sources off; capturing a second image that includes the object illuminated by the first one of the two optical light sources; illuminating the object with the second one of the two optical light sources while keeping the first one of the two optical light sources off; and capturing a third image that includes the object illuminated by the second one of the two optical light sources.

Example 56: The non-transitory machine-readable medium of Example 55 wherein the plurality of machine-readable instructions, when executed by the one or more processors are adapted to cause the one or more processors to perform a method further comprising: comparing the first image to the second image; compare the first image to the third image; and determining the rotational offset of the tool relative to the catheter based on the comparing the first and second images, comparing the first and third images, or a combination thereof.

Example 57: The non-transitory machine-readable medium of Example 47 wherein the plurality of machine-readable instructions, when executed by the one or more processors are adapted to cause the one or more processors to perform a method further comprising: illuminating the object with the two optical light sources, having different correlated color temperatures respectively; capturing the first image that includes the object illuminated by the two optical light sources; analyzing a non-uniform shading of the object in the first image; and determining the rotational offset of the tool relative to the catheter based on the analyzing the non-uniform shading of the object in the first image.

Example 58: The non-transitory machine-readable medium of Example 47 wherein the first image is an image of an anatomy of a patient and a second image is created by one or more CT scans of the anatomy of the patient and is the image of the anatomy at a 0 (zero) degree angular orientation, wherein the determining the angular orientation further comprises comparing the first image to the second image and determining the angular orientation of the first image based on the comparing.

Example 59: The non-transitory machine-readable medium of Example 47 wherein the plurality of machine-readable instructions, when executed by the one or more processors are adapted to cause the one or more processors to perform a method further comprising: rotating and scaling the first image to create a third image that matches a second image, thereby determining the rotational offset needed to rotate the first image to match the second image.

The invention claimed is:

1. An apparatus comprising:

a processor; and a memory having computer readable instructions stored thereon, the computer readable instructions, when executed by the processor, cause the apparatus to:

capture, via an image sensor of a tool installed at least partially within a catheter, a first image within a lumen of the catheter, the first image comprising a plurality of pixels;

identify a first subset of the plurality of pixels comprising a viewable feature, and a second subset of the plurality of pixels comprising a background color;

adjust the second subset to a neutral color;

create a modified image by filtering the plurality of pixels to remove the second subset;

determine an angular orientation of the viewable feature in the modified image;

determine a rotational offset of the tool relative to the catheter based on the angular orientation of the viewable feature; and based on the rotational offset: (1) adjust manipulation of a control cable of the catheter; or (2) rotate one or more images captured by the image sensor.

2. The apparatus of claim 1, wherein the viewable feature is a longitudinal marking that extends longitudinally along an interior wall of the catheter.

3. The apparatus of claim 2, wherein the longitudinal marking is blue, and wherein the computer readable instructions, when executed by the processor, further cause the apparatus to:

assign a hue saturation value (HSV) to each of the plurality of pixels;

determine the first subset of the plurality of pixels by grouping each of the pixels with an HSV of blue together; and determine the second subset of the plurality of pixels by grouping each of the pixels not included in the first subset.

4. The apparatus of claim 1, wherein filtering the plurality of pixels comprises adjusting pixels that are outside of a circularly shaped filter to zero.

5. The apparatus of claim 1, wherein filtering the plurality of pixels comprises adjusting pixels that are outside of a custom shaped filter to zero, and wherein the custom shaped filter is proportionately larger than a shape formed by the viewable feature.

6. The apparatus of claim 1, wherein the computer readable instructions, when executed by the processor, further cause the apparatus to:

determine a first centroid of the first subset; and determine the angular orientation of the viewable feature in the modified image based on the first centroid.

7. The apparatus of claim 1, wherein a portion of the plurality of pixels that have an intensity above a threshold are set to zero.

8. The apparatus of claim 1, wherein the first image is divided into multiple sections, and wherein the angular orientation indicates which one of the multiple sections the viewable feature is positioned.

9. The apparatus of claim 8, wherein the multiple sections comprise four equal quadrants.

10. The apparatus of claim 1, wherein the computer readable instructions, when executed by the processor further cause the apparatus to:

identify a third subset of the plurality of pixels comprising a second viewable feature; and determine an angular orientation of the second viewable feature.

11. The apparatus of claim 10, wherein determining the rotational offset of the tool relative to the catheter is further based on the angular orientation of the second viewable feature.

12. The apparatus of claim 10, wherein the viewable feature is a first longitudinal marking that extends longitudinally along an interior wall of the catheter and the second viewable feature is a second longitudinal marking that extends longitudinally along the interior wall of the catheter, and wherein the first and second longitudinal markings are spaced away from each other around the interior wall by a first angle.

13. The apparatus of claim 12, wherein the first angle is selected from a range from 30 to 180 degrees.

14. The apparatus of claim 12, wherein the first angle is 180 degrees.

15. The apparatus of claim 12, wherein the first longitudinal marking is blue and the second longitudinal marking is yellow, and wherein the computer readable instructions, when executed by the processor, further cause the apparatus to:

assign a hue saturation value (HSV) to each of the plurality of pixels;

determine the first subset of the plurality of pixels by grouping each of the pixels with an HSV of blue together;

determine the third subset of the plurality of pixels by grouping each of the pixels with an HSV of yellow together; and determine the second subset of the plurality of pixels by grouping each of the pixels not included in the first and third subsets.

16. The apparatus of claim 10, wherein the computer readable instructions, when executed by the processor, further cause the apparatus to:

determine a first centroid of the first subset;

determine a second centroid of the third subset; and determine the angular orientation of each of the viewable feature and the second viewable feature in the modified image based on the first and second centroids.

17. The apparatus of claim 10, wherein the first image is divided into multiple sections, and wherein the angular orientations indicate which one of the multiple sections each of the viewable feature and the second viewable feature is positioned.

18. A method, comprising:

capturing, via an image sensor of a tool installed at least partially within a catheter, a first image within a lumen of the catheter, the first image comprising a plurality of pixels;

identifying a first subset of the plurality of pixels comprising a viewable feature, and a second subset of the plurality of pixels comprising a background color;

adjusting the second subset to a neutral color;

creating a modified image by filtering the plurality of pixels to remove the second subset;

determining an angular orientation of the viewable feature in the modified image;

determining a rotational offset of the tool relative to the catheter based on the angular orientation of the viewable feature; and based on the rotational offset: (1) adjusting manipulation of a control cable of the catheter; or (2) rotating one or more images captured by the image sensor.

19. The method of claim 18, wherein the viewable feature is a blue longitudinal marking that extends longitudinally along an interior wall of the catheter, and wherein the method further comprises:

assigning a hue saturation value (HSV) to each of the plurality of pixels;

determining the first subset of the plurality of pixels by grouping each of the pixels with an HSV of blue together; and determining the second subset of the plurality of pixels by grouping each of the pixels not included in the first subset.

20. The method of claim 18, further comprising:

identifying a third subset of the plurality of pixels comprising a second viewable feature; and determining an angular orientation of the second viewable feature, wherein determining the rotational offset of the tool relative to the catheter is further based on the angular orientation of the second viewable feature.

\* \* \* \* \*